US009624295B2

(12) United States Patent
Medich et al.

(10) Patent No.: US 9,624,295 B2
(45) Date of Patent: Apr. 18, 2017

(54) USES AND COMPOSITIONS FOR TREATMENT OF PSORIATIC ARTHRITIS

(75) Inventors: John R. Medich, East Hanover, NJ (US); Robert L. Wong, Basking Ridge, NJ (US); Renee J. Perdok, Gurnee, IL (US); Eric H. Sasso, Evanston, IL (US); Rebecca S. Hoffman, Wilmette, IL (US); Phillip Mease, Seattle, WA (US); Christopher T. Ritchlin, Canandaigua, NY (US)

(73) Assignee: Abbvie Biotechnology Ltd., Hamilton (BM)

( * ) Notice: Subject to any disclaimer, the term of this patent is extended or adjusted under 35 U.S.C. 154(b) by 1451 days.

(21) Appl. No.: 11/786,459

(22) Filed: Apr. 10, 2007

(65) Prior Publication Data
US 2009/0028794 A1 Jan. 29, 2009

Related U.S. Application Data

(60) Provisional application No. 60/790,909, filed on Apr. 10, 2006, provisional application No. 60/809,770, filed on May 30, 2006, provisional application No. 60/815,489, filed on Jun. 20, 2006, provisional application No. 60/858,376, filed on Nov. 10, 2006, provisional application No. 60/899,262, filed on Feb. 2, 2007, provisional application No. 60/909,683, filed on Apr. 2, 2007.

(51) Int. Cl.
A61K 39/00 (2006.01)
A61K 39/395 (2006.01)
C07K 16/24 (2006.01)

(52) U.S. Cl.
CPC ...... *C07K 16/241* (2013.01); *A61K 2039/505* (2013.01); *A61K 2039/545* (2013.01); *A61K 2039/55* (2013.01); *C07K 2317/21* (2013.01); *C07K 2317/565* (2013.01); *C07K 2317/76* (2013.01); *G01N 2800/102* (2013.01)

(58) Field of Classification Search
CPC ............ A61K 2039/505; A61K 9/0019; A61K 39/00; A61K 47/48546; A61K 39/395; A61K 38/19; A61K 2039/6056; A61K 38/191; C07K 16/241; C07K 2317/92; C07K 2316/96; C07K 16/00; C07K 14/70575; C07K 2316/95; C07K 14/70578; C07K 2317/76
See application file for complete search history.

(56) References Cited

U.S. PATENT DOCUMENTS

| | | | |
|---|---|---|---|
| 5,231,024 A | 7/1993 | Moeller et al. | |
| 5,654,407 A | 8/1997 | Boyle et al. | |
| 5,656,272 A | 8/1997 | Le et al. | |
| 5,705,389 A | 1/1998 | Braham et al. | |
| 5,795,967 A | 8/1998 | Aggarwal et al. | |
| 5,859,205 A | 1/1999 | Adair et al. | |
| 5,877,293 A | 3/1999 | Adair et al. | |
| 5,929,212 A | 7/1999 | Jolliffe et al. | |
| 5,958,953 A | 9/1999 | Marfat | |
| 5,994,510 A | 11/1999 | Adair et al. | |
| 6,090,382 A * | 7/2000 | Salfeld et al. ............. | 424/133.1 |
| 6,177,077 B1 | 1/2001 | Tobinick | |
| 6,214,870 B1 | 4/2001 | McClure et al. | |
| 6,235,281 B1 | 5/2001 | Stenzel et al. | |
| 6,258,562 B1 | 7/2001 | Salfeld et al. | |
| 6,270,766 B1 | 8/2001 | Feldman et al. | |
| 6,379,666 B1 | 4/2002 | Tobinick | |
| 6,419,944 B2 | 7/2002 | Tobinick | |
| 6,423,321 B2 | 7/2002 | Tobinick | |
| 6,448,380 B2 | 9/2002 | Rathjen et al. | |
| 6,451,983 B2 | 9/2002 | Rathjen et al. | |
| 6,498,237 B2 | 12/2002 | Rathjen et al. | |
| 6,509,015 B1 | 1/2003 | Salfeld et al. | |
| 6,537,549 B2 | 3/2003 | Tobinick | |
| 6,562,006 B1 | 5/2003 | Hjertman et al. | |
| 6,593,458 B1 | 7/2003 | Rathjen et al. | |
| 6,844,365 B2 * | 1/2005 | Di Napoli ..................... | 514/569 |
| 7,012,135 B2 | 3/2006 | Athwal et al. | |
| 7,070,775 B2 | 7/2006 | Le et al. | |
| 7,192,584 B2 | 3/2007 | Le et al. | |
| 7,206,301 B2 * | 4/2007 | Wu et al. ..................... | 370/338 |
| 7,214,376 B2 | 5/2007 | Le et al. | |
| 7,223,394 B2 | 5/2007 | Salfeld et al. | |
| 7,250,165 B2 | 7/2007 | Heavner et al. | |
| 7,276,239 B2 | 10/2007 | Le et al. | |

(Continued)

FOREIGN PATENT DOCUMENTS

EP 0101681 3/1984
EP 0186833 7/1986

(Continued)

OTHER PUBLICATIONS

Van der Kerkhof P. Br J Dermatol 1997; 137:661-662.*
Mease et al., Lancet 356:385-390, Jul. 29, 2000.*
MedicineNet.com (http://www.medterms.com/script/main/art.asp?articlekey=17659#), accessed Nov. 1, 2010.*
Kvien et al., British Journal or Rheumatology 35:359-363, 1996.*
Oglivie et al. 2001. Br. J. Dermat. 144:587-589.*
Keystone et al. (a) 2001. Prague Congress, eular 2001. abstract OP0086.*
Keystone et al (b) 2003. Ann. Rheum Dis. 62(Suppl1) 64-65, Abstract OP0003.*
Mease 2005. Expert Opin. Biol. Ther 5:1491-1504.*
Mease et al. 2005. Arth. and Rheum. 52:3279-3289.*
Jantti et al. 2002. Clin Rheumatol. 21:353-356.*
Tikly et al. 2009. SA Fam Pract. 51:188-193.*
U.S. Appl. No. 10/622,683.
U.S. Appl. No. 11/786,053.
U.S. Appl. No. 11/786,444.
U.S. Appl. No. 11/786,445.
U.S. Appl. No. 11/786,461.
U.S. Appl. No. 11/788,312.

(Continued)

*Primary Examiner* — Shulamith H Shafer
(74) *Attorney, Agent, or Firm* — Foley Hoag LLP

(57) ABSTRACT

The invention provides methods, uses and compositions for the treatment of psoriatic arthritis. The invention describes methods and uses for treating psoriatic arthritis, wherein a TNFα inhibitor, such as a human TNFα antibody, or antigen-binding portion thereof, is used to psoriatic arthritis in a subject. Also described are methods for determining the efficacy of a TNFα inhibitor for treatment of psoriatic arthritis in a subject.

6 Claims, 8 Drawing Sheets

(56) References Cited

U.S. PATENT DOCUMENTS

| | | |
|---|---|---|
| 7,438,907 B2 | 10/2008 | Schuurman et al. |
| 7,521,206 B2 | 4/2009 | Heavner et al. |
| 7,541,031 B2 | 6/2009 | Salfeld et al. |
| 7,588,761 B2 | 9/2009 | Salfeld et al. |
| 7,674,769 B2 | 3/2010 | Creasey |
| 7,691,378 B2 | 4/2010 | Heavner et al. |
| 7,754,206 B2 | 7/2010 | Clarke et al. |
| 7,807,389 B2 | 10/2010 | Ritchlin et al. |
| 7,833,525 B2 | 11/2010 | Shenoy et al. |
| 7,842,709 B2 | 11/2010 | Tartaglia et al. |
| 7,863,426 B2 | 1/2011 | Wan et al. |
| 7,919,264 B2 | 4/2011 | Maksymowych et al. |
| 8,034,906 B2 | 10/2011 | Borhani et al. |
| 8,092,998 B2 | 1/2012 | Stuhlmuller et al. |
| 8,093,045 B2 | 1/2012 | Pla et al. |
| 8,187,836 B2 | 5/2012 | Hsieh |
| 8,197,813 B2 | 6/2012 | Salfeld et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,372,400 B2 | 2/2013 | Salfeld et al. |
| 8,420,081 B2 | 4/2013 | Fraunhofer et al. |
| 8,636,704 B2 | 1/2014 | Shang et al. |
| 8,679,061 B2 | 3/2014 | Julian et al. |
| 8,753,839 B2 | 6/2014 | Fraunhofer et al. |
| 8,808,700 B1 | 8/2014 | Hoffman et al. |
| 8,846,046 B2 | 9/2014 | Kaymakcalan et al. |
| 8,889,135 B2 | 11/2014 | Fischkoff et al. |
| 8,889,136 B2 | 11/2014 | Hoffman et al. |
| 8,906,373 B2 | 12/2014 | Banerjee et al. |
| 9,067,992 B2 * | 6/2015 | Hoffman et al. |
| 2001/0021380 A1 | 9/2001 | Pluenneke |
| 2002/0136723 A1 | 9/2002 | Feldmann et al. |
| 2003/0012786 A1 | 1/2003 | Teoh et al. |
| 2003/0113318 A1* | 6/2003 | Tobinick .......... 424/134.1 |
| 2003/0161828 A1 | 8/2003 | Abdelghany et al. |
| 2003/0204066 A1 | 10/2003 | Le et al. |
| 2003/0206898 A1 | 11/2003 | Fischkoff et al. |
| 2003/0219438 A1 | 11/2003 | Salfeld et al. |
| 2004/0009172 A1 | 1/2004 | Fischkoff et al. |
| 2004/0033228 A1 | 2/2004 | Krause et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0219142 A1 | 11/2004 | Banerjee et al. |
| 2005/0249735 A1 | 11/2005 | Le et al. |
| 2006/0018907 A1 | 1/2006 | Le et al. |
| 2006/0083741 A1 | 4/2006 | Hoffman et al. |
| 2006/0246073 A1 | 11/2006 | Knight et al. |
| 2007/0041905 A1 | 2/2007 | Hoffman et al. |
| 2007/0081996 A1 | 4/2007 | Hoffman et al. |
| 2007/0196373 A1 | 8/2007 | Le et al. |
| 2007/0202104 A1 | 8/2007 | Banerjee et al. |
| 2007/0298040 A1 | 12/2007 | Le et al. |
| 2008/0025976 A1 | 1/2008 | Le et al. |
| 2008/0118496 A1 | 5/2008 | Medich et al. |
| 2008/0131374 A1 | 6/2008 | Medich et al. |
| 2008/0166348 A1 | 7/2008 | Kupper et al. |
| 2008/0193466 A1 | 8/2008 | Banerjee et al. |
| 2009/0028794 A1 | 1/2009 | Medich et al. |
| 2009/0110679 A1 | 4/2009 | Li et al. |
| 2009/0123378 A1 | 5/2009 | Wong et al. |
| 2009/0226530 A1 | 9/2009 | Lassner et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0021451 A1 | 1/2010 | Wong |
| 2010/0040630 A1 | 2/2010 | Elden et al. |
| 2010/0278822 A1 | 11/2010 | Fraunhofer et al. |
| 2011/0171227 A1 | 7/2011 | Okun et al. |
| 2012/0014956 A1 | 1/2012 | Kupper et al. |
| 2013/0122011 A1 | 5/2013 | Hoffman et al. |
| 2013/0243786 A1 | 9/2013 | Banerjee et al. |

FOREIGN PATENT DOCUMENTS

| | | |
|---|---|---|
| EP | 0212489 | 3/1987 |
| EP | 0351789 | 1/1990 |
| EP | 0366043 | 5/1990 |
| EP | 0492448 | 7/1992 |
| EP | 260 610 | 9/1993 |
| EP | 0614984 | 9/1994 |
| JP | 11127882 | 5/1999 |
| JP | 2001-302542 | 10/2001 |
| WO | WO-91/02078 | 2/1991 |
| WO | WO-91/03553 A1 | 3/1991 |
| WO | WO-91/09967 A1 | 7/1991 |
| WO | WO-92/11383 | 7/1992 |
| WO | WO-92/16553 | 10/1992 |
| WO | WO-93/06213 | 4/1993 |
| WO | WO-93/11793 | 6/1993 |
| WO | WO-94/29347 | 12/1994 |
| WO | WO-95/23813 | 9/1995 |
| WO | WO-97/29131 | 8/1997 |
| WO | WO-98/05357 | 2/1998 |
| WO | WO-98/22460 | 5/1998 |
| WO | WO-01/00229 | 1/2001 |
| WO | WO-01/37874 | 5/2001 |
| WO | WO-01/43773 | 6/2001 |
| WO | WO-01/62272 | 8/2001 |
| WO | WO-02/12502 | 2/2002 |
| WO | WO-02/096461 | 12/2002 |
| WO | WO-02/100330 | 12/2002 |
| WO | WO-2004/009776 A2 | 1/2004 |
| WO | WO-2004/037205 A2 | 5/2004 |
| WO | WO-2004/092448 | 10/2004 |
| WO | WO-2006/041970 | 4/2006 |

OTHER PUBLICATIONS

U.S. Appl. No. 11/788,740.
U.S. Appl. No. 11/804,587.
U.S. Appl. No. 11/818,510.
U.S. Appl. No. 11/824,516.
U.S. Appl. No. 11/880,433.
U.S. Appl. No. 12/130,831.
U.S. Appl. No. 12/306,513.
U.S. Appl. No. 12/646,891.
[online] Statement on a Nonproprietary Name Adopted by the USAN Council: Adalimumab, [retrieved on May 19, 2011] Retrieved from: www.ama-assn.org/resources/doc/usan/adalimumab.doc, p. 1.
Abbott Laboratories, Earnings Conference Call transcript (Apr. 9, 2002).
Abbott Laboratories, Earnings Conference Call transcript (Jul. 11, 2002).
Aboulafia, "Etanercept for the treatment of human immunodeficiency virus-associated D psoriatic arthritis," Mayo Clinic Proceedings, 75(10):1093-1098 (2000).
Abraham et al., "Efficacy and Safety of Monoclonal Antibody to Human Tumor Necrosis Factor a in Patients with Sepsis Syndrome," JAMA, 273(12): 934-941 (1995).
Advisory Committee Briefing Document Humira (Adalimumab), Abbott Laboratories, Briefing document dated Feb. 4, 2003.
Alexander et al., "Elevated Levels of Proinflammatory Cytokines in the Semen of Patients With Chronic Prostatitis/Chronic Pelvic Pain Syndrome," Urology, 52:744 (1998).
Antoni et al., "Infliximab for psoriasis and psoriatic arthritis," Clin. Exp. Rheum., 20:S122-S125 (2002).
Antoni et al., "Open-label study of infliximab treatment for psoriatic arthritis: clinical and C2 magnetic resonance imaging measurements of reduction of inflammation," Arthritis & Rheumatism, 47(5):506-512 (2002).

(56) References Cited

OTHER PUBLICATIONS

Antoni et al., "Successful treatment of severe psoriatic arthritis with infliximab," Arthr. Rheum. 42(Suppl.):5371 (Abstract #1801) (1999).

Antoni, C., et al., "Successful Treatment of Psoriatic Arthritis with Infliximab in a MRI Controlled Study," Abstract OP 6.1, J. of Rheumatology, 27 (Supp. 59):24 (2000).

Asadullah et al., "A high prevalence of cytomegalovirus antigenaemia in patients with moderate to severe chronic plaque psoriasis: an association with systemic tumor necrosis factor α overexpression," Br. J. Dermatol, 141(1):94-102 (1999).

Asakawa et al., "Effects of Cernitin Pollen-Extract (Cernilton) on Inflammatory Cytokines in Sex-Hormone Induced Nonbacterial Prostatitis Rats," Hinyokika Kiyo, 47:459-465 (2001).

Asli et al., "Inhibition of tumor necrosis factor alpha and ankylosing spondylitis," N Engl J Med, 348(4):359-61 (2003).

Awni et al., "Steady-State Pharmacokinetics (PK) of Adalimumab (Humira1M, Abbott) Following 40 mg Subcutaneous (sc) Injection Every Other Week (eow) in Rheumatoid Arthritis (RA) Patients with and without Methotrexate (MTX) Background Therapy," Arthritis Rheum, 48(9):S140 (2003).

Baeten et al., "Immunomodulatory effects of anti-tumor necrosis factor alpha therapy on synovium in spondylarthropathy: histologic findings in eight patients from an open-label pilot study," Arthritis & Rheumatism, 44(1):186-195 (2001).

Bansback et al., "The Cost Effectiveness of Adalimumab (Humira™, Abbott) in the Treatment of Patients with Moderate to Severe Rheumatoid Arthritis (RA)," Arthritis Rheum, 48(9):5611 (2003).

Barbuto et al., "Production of Neutralizing Antibodies to Tumor Necrosis Factor by Human Tumor-Infiltrating B Lymphocytes," Proc. Am. Assoc. Cancer Res, 34(487) Abstr. 2904 (1993).

Barrera et al., "Drug survival, efficacy and toxicity of monotherapy with a fully human anti-tumour necrosis factor-a antibody compared with methotrexate in long-standing rheumatoid arthritis," Rheumatology, 41:430-439 (2002).

Barrera et al., "Effect of a Fully Human Anti-TNFa Monoclonal Antibody on the Local and Systemic Expression of TNFa and IL-113," Arthritis Rheum, 42(9):S75 (1999).

Bathon et al., "A Comparison of Etanercept and Methotrexate in Patients with early Rheumatoid Arthritis," N Engl J Med., 343(22):1586-93 (2000).

Baugh et al., "Mechanisms for modulating TNFa in immune and inflammatory disease," Current Opinion in Drug Discovery & Development, 4(5):635-650 (2001).

Beers et al., "Juvenile rheumatoid arthritis," The Merck Manual of Diagnosis and Therapy, 17(270):2402-2403 (1999).

Bendtzen et al., "Auto-antibodies to IL-1a and TNFa in Normal Individuals and in Infectious and Immunoinflammatory Disorders," The Physiological and Pathological Effects of Cytokines, 447-452 (1990).

Bhole et al., "Differences in body mass index among individuals with PsA, psoriasis, RA and the general population," Rhem., 51:552-556 (2012).

Billiau et al., "Infliximab for systemic onset juvenile idiopathic arthritis: experience in 3 children," Journal of Rheumatology, 29(5):1111-1114 (2002).

Biotech Week, "Cambridge Antibody Technology; Cambridge Antibody reports interim results on several trials" (Jun. 19, 2002).

Bodmer et al., "Preclinical review of anti-tumor necrosis factor monoclonal antibodies," Critical Care Medicine, 21(10):S441-S446 (1993).

Boeger et al., "Treatment of ankylosing spondylitis with infliximab," Ann Rheum Dis., 60(12):1159-1160 (2001).

Boeksteger et al., "Repeated administration of a F(ab')2 fragment of an anti-tumor necrosis factor alpha monoclonal antibody in patients with severe sepsis: effects on the cardiovascular system and cytokine levels," Shock, 1(4):237-245 (1994).

Bombardier et al., "Pattern of DMARD use in a North American Cohort of Patients with Early Rheumatoid Arthritis (RA) (SONORA)," Arthritis Rheum, 46(9):S344 (2002).

Boyle et al., "A Novel Monoclonal Human IgM Autoantibody which Binds Recombinant Human and Mouse Tumor Necrosis Factor-a," Cell. Immunol, 152:556-68 (1993).

Boyle et al., "The B5 Monoclonal Human Autoantibody Binds to Cell Surface TNFa on Human Lymphoid Cells and Cell Lines and Appears to Recognize a Novel Epitope," Cell. Immunol., 152:569-81 (1993).

Brandt et al., "Successful short term treatment of severe undifferentiated spondyloarthropathy with the anti-tumor necrosis factor-alpha monoclonal antibody infliximab," J Rheumatol, 29(1):118-122 (2002).

Brandt et al., "Successful treatment of active ankylosing spondylitis with the anti-tumor necrosis factor alpha monoclonal antibody infliximab," Arthritis Rheum, 43(6):1346-1352 (2000).

Braun et al., "Anti-TNFalpha: a new dimension in the pharmacotherapy of the spondyloarthropathies!?" Ann Rheum Dis, 59(6):404-6 (2000).

Braun et al., "Anti-tumour necrosis factor alpha therapy for ankylosing spondylitis: international experience," Ann Rheum Dis, 61(3):iii51-iii60 (2002).

Braun et al., "Biologic therapies in the spondyloarthritis: new opportunities, new challenges," Curr Opin Rheumatol, 15(4):394-407 (2003).

Braun et al., "International ASAS consensus statement for the use of anti-tumour necrosis factor agents in patients with ankylosing spondylitis," Ann Rheum Dis, 62(9):817-24 (2003).

Braun et al., "New treatment options in spondyloarthropathies: increasing evidence for significant efficacy of anti-tumor necrosis factor therapy," Curr Opin Rheumatol, 13(4):245-9 (2001).

Braun et al., "Novel approaches in the treatment of ankylosing spondylitis and other spondyloarthritides," Expert Opin Investig Drugs, 12(7):1097-109 (2003).

Braun et al., "Role of Novel Biological Therapies in Psoriatic Arthritis," BioDrugs 17(3):187-199 (2003).

Braun et al., "Therapy of ankylosing spondylitis and other spondyloarthritides: established medical; treatment anti-TNF-a therapy and other novel approaches," Arthritis Research, 4:307-321 (2002).

Braun et al., "Treatment of active ankylosing spondylitis with infliximab: a randomized controlled multicentre trial," Lancet, 659(9313):1187-93 (2002).

Breban et al., "Efficacy of infliximab in refractory ankylosing spondylitis: results of a six-month open-label study," Rheumatology, 41(11):1280-1285 (2002).

Breedveld et al., "Sustained Efficacy Over 4 Years with Adalimumab in Patients with Active Rheumatoid Arthritis," Ann. Rheum. Dis, 62(1):169 (2003).

Breedveld et al., "Sustained Efficacy over 5 Years with Adalimumab (Humira®) in Patients with Active Rheumatoid Arthritis," Arthritis Rheum, 48(9):S118 (2003).

Breedveld et al., "The Fully Human Anti-TNF Antibody Adalimumab (D2E7) in Combination with Methotrexate (MTX) in the Treatment of Active Rheumatoid Arthritis: Results of a 2-Year Study," EULAR, Prague, Czech Republic (2001).

Breedveld et al., "The Long-term Efficacy and Safety of Adalimumab (D2E7), the Fully Human Anti-TNF Monoclonal Antibody, in Combination with Methotrexate in the Treatment of Rheumatoid Arthritis: Results of a 2-Year Study," JCR, 8(3):S46 (2002).

Brekke et al., "Therapeutic Antibodies for Human Diseases at the Dawn of the Twenty-first Century," Nat Rev Drug Discov., 2(3):240 (2003).

Brisby et al., "Proinflammatory cytokines in cerebrospinal fluid and serum in patients with disc herniation and sciatica", Eur Spine J., 11:62-66 (2002).

Burmester et al., "Effect of Dose Interruptions on the Efficacy and Safety of Adalimumab in Patients with RA," Ann. Rheum. Dis., 62(1):192 (2003).

(56) References Cited

OTHER PUBLICATIONS

Burmester et al., "Long-Term Efficacy and Safety of Adalimumab (D2E7) Monotherapy in Patients With DMARD-Refractory Rheumatoid Arthritis—Results From a 2-Year Study," Arthritis Rheum, 46(9):S537 (2002).

Burmester et al., "Sustained Efficacy of Adalimumab Monotherapy for More than Four Years in DMARD-Refractory RA," Ann. Rheum. Dis., 62(1):192-3 (2003).

Calabrese, "Human immunodeficiency virus (HIV) infection and arthritis," Rheum Dis Clin North Am., 19(2):477-88 (1993).

Canadian Coordinating Office for Health Technology Assessment, "Emerging Drug List: Adalimumab and Rheumatoid Arthritis," No. 42, available at https://www.cadth.ca/media/pdf/108_No42_adalimumab_edrug_e.pdf (2003).

Carlin et al., "A 50% reduction in the psoriasis area and severity index (PASI.50) is a clinically significant endpoint in the assessment of psoriasis," Journal of the American Academy of Dermatology, 50(6): 859-866 (2003).

Case, "Old and New Drugs Used in Rheumatoid Arthritis: A Historical Perspective," American Journal of Therapeutics, 8:163-179 (2001).

Casset et al., "A peptide mimetic of an anti-CD4 monoclonal antibody by rational design," Biochemical and Biophysical Research Communications, 307:198-205 (2003).

Cauza et al., "Treatment of psoriatic arthritis and psoriasis vulgaris with the tumor necrosis factor inhibitor infliximab," Rheumatol Int. 22:227-232 (2002).

Cavagna et al., "Infliximab in the treatment of adult Still's disease refractory to conventional therapy," Clin Exp Rheumatol, 19(3):329-332 (2001).

Challener, Cynthia, "Biotechnology drugs offer fertile ground for API producers," Chemical Market Reporter 260(13):FR3-FR12 (2001).

Chartash et al., "Adalimumab Improves Fatigue in Patients with Active Rheumatoid Arthritis," Ann. Rheum. Dis., 62(1):349 (2003).

Chaudhari et al., "Efficacy and safety of infliximab monotherapy for plaque-type psoriasis: a randomized trial," Lancet, 357(9271):1842-7 (2001).

Chew et al., "Successful treatment of severe psoriasis and psoriatic arthritis with adalimumab," Brit J Derm, 151(2):492-496 (2004).

Chikanza, "Juvenile rheumatoid arthritis: therapeutic perspectives," Pediatric Drugs 4(5):335-348 (2002).

Chow et al., "Effect of monoclonal antibody on human tumor necrosis factor (TNF MAb) on NFa, IL-113. and IL-6 levels in patients with sepsis syndrome," Clinical Research, 42(2): 299A (1994).

Clinical Trial NCT00195507, "Study Evaluating Etanercept in the Treatment of Subjects With Psoriasis" Sep. 13, 2005 Wyeth ClinicaiTrials.Qov Identifier: NCT00195507.

Clinical Trial NCT00659412, "A Placebo-Controlled Study With an Extension Examining the Safety and Efficacy of Alefacept in Psoriatic Arthritis," Apr. 14, 2008 Astellas Pharma Inc. ClinicalTrials.gov Identifier: NCT00659412.

Cohen et al., "Intersept: An international, multicenter, placebo-controlled trial of monoclonal antibody to human tumor necrosis factor-a in patients with sepsis," Crit Care Med., 24(9):1431-1440 (1996).

Colman, "Effects of amino acid sequence changes on antibody-antigen interactions," Research in Immunology, 145(1):33-36 (1994).

Corluy, "Clinical Response Compared to DAS28 and ACR-Response Criteria in Rheumatoid Arthritis Patients on lnfliximab," EULAR, abstract (2002).

Cox et al., "A directory of human germ-line V segments reveals a strong bias in their usage," Eur. J. Immunol., 24(2):827-36 (1994).

Davison et al., "Etanercept for severe psoriasis and psoriatic arthritis: observations on combination therapy," British Journal of Dermatology, 147(4):831-2 (2002).

Dayer et al., "Anti-TNF-alpha therapy for ankylosing spondylitis-a specific or nonspecific treatment?" N Engl J Med, 346(18):1399-400 (2002).

Decision Resources website, "The Highest Proportions of Surveyed Rheumatologists and Surveyed MCO Pharmacy Directors Selected Humira as the Most Efficacious Therapy for Moderate to Severe Psoriatic Arthritis, When Compared to Other Available Therapies," Web. Mar. 28, 2011.

den Broeder et al., "A Single Dose, Placebo Controlled Study of the Fully Human Anti-Tumor Necrosis Factor-a Antibody Adalimumab (D2E7) in Patients with Rheumatoid Arthritis," The Journal of Rheumatology, 29(11): 2288-2298 (2002).

den Broeder et al., "Long term anti-tumour necrosis factor a monotherapy in rheumatoid arthritis: effect on radiological course and prognostic value of markers of cartilage turnover and endothelial activation," Ann. Rheum. Dis., 61:311-318 (2002).

den Broeder et al., "The Effect of D2E7, a new human anti-TNFa monoclonal antibody, on the oxidative burst of PMN in patients with RA," Arthritis and Rheumatism, 41(9):S57 (1998).

Department of Surgery, University of Toronto, Annual Report (1998-1999) found online at http://www.surQ.med.utoronto.ca/AnnRep/AR98 99/index.html.

Dernis et al., "Infliximab in spondylarthropathy-Influence on bone density," Clin Exp Rheumatol, 20(6 Suppl 28):S185-6 (2002).

Eckelbecker, Lisa, "Cranking out doses," Worcester, Mass. Telegram & Gazette, p. E1 (Jan. 3, 2003).

Eckelbecker, Lisa, "D2E7 Placed Before FDA; Approval Sought for Local Drug," Worcester, Mass. Telegram & Gazette, p. E1 (Apr. 10, 2002).

Egan et al., "A randomized, single-blind, pharmacokinetic and dose response study of subcutaneous methotrexate, 15 and 25 MG/week, for refractory ulcerative colitis and Crohn's Disease," Gastroenterology, 114(4):G3978 (1998).

Eisermann et al., "Tumor necrosis factor in peritoneal fluid of women undergoing laparoscopic surgery," Fertility and Sterility, 50:573 (1988).

Elewski, "Infliximab for the treatment of severe pustular psoriasis," J. Am. Acad. Dermatol, 47(5):796-7 (2002).

Elkayam et al., "From wheels to feet: a dramatic response of severe chronic psoriatic arthritis to etanercept," Ann. Rheumatic Diseases, 59:839 (2000).

Elliott et al., "Suppression of fever and the acute-phase response in a patient with juvenile chronic arthritis treated with monoclonal antibody to tumour necrosis factor-alpha (cA2)," British Journal of Rheumatology, 36(5): 589-593 (1997).

Elliott et al., "Treatment of rheumatoid arthritis with chimeric monoclonal antibodies to tumor necrosis factor a," Arthritis & Rheumatism, 36(12):1681-90 (1993).

Emerald BioSystems Wizard I & II Instructions [online], Jan. 22, 2011 [retrieved Jan. 6, 2015]. Retrieved from Internet Archive wayback machine: <https://web.archive.org/web/20010122011100/http://www.emeraldbiostructures.com/wiz_instructions.htm>, 4 pages.

Emerald BioSystems Wizard II Formulations [online], Dec. 17, 2000 [retrieved Jan. 6, 2015]. Retrieved from Internet Archive wayback machine: <https://web.archive.org/web/20001217030900/http://www.emeraldbiostructures.com/wiz2_for mulations.htm>, 3 pages.

Emery et al., "Changes in PRO-MMP-1 in Relation to Standard Measures of Disease Activity Over a 6 Month Treatment Period with Adalimumab (D2E7) in Rheumatoid Arthritis," Arthritis & Rheumatism, 44(9):S215 (2001).

Emery et al., "Improvement in HAQ Disability in Rheumatoid Arthritis (RA) with Adalimumab (Humira™) Based on Duration of Disease," Arthritis Rheum, 48(9):S313 (2003).

Enbrel (etanercept) Label, 2007.

Enbrel® (etanercept) Nov. 1998 Label.

Ettehadi et al., "Elevated tumor necrosis factor-alpha (TNF-a) biological activity in psoriatic skin lesions," Clin. Exp. Immunol, 96:146-151 (1994).

Farhi et al., "Global Assessment of Psoriasis Severity and Change from Photographs: A Valid and Consistent Method," Journal of Investigative Dermatology, 128: 2198-2203 (2008).

(56) References Cited

OTHER PUBLICATIONS

FDA approval of Humira (adalimumab): Prescribing information for Humira (adalimumab), Abbott Laboratories, North Chicago, IL, USA, Dec. 20, 2002, pp. 1-16.
Feldman et al., "Psoriasis assessment tools in clinical trials," Ann Rheum Dis, 64(2):ii65-ii68 (2005).
Feldmann et al., "Anti-TNFa Therapy of Rheumatoid Arthritis: What Have We Learned," Annu. Rev. Immunol., 19:163-196 (2001).
Figini et al., "In Vitro Assembly of Repertoires of Antibody Chains on the Surface of Phage by Renaturation," J. Mol. Biol., 239:68-78 (1994).
Flendrie et al., "Survival during treatment with tumor necrosis factor blocking agents in rheumatoid arthritis," Ann. Rheum. Dis., 62(2): ii30-ii33 (2003).
Fomsgaard et al., "Auto-antibodies to Tumour Necrosis Factor a in Healthy Humans and Patients with Inflammatory Diseases and Gram-Negative Bacterial Infections," Scand. J. Immunol, 30:219-23 (1989).
Foote et al., "Antibody Framework Residues Affecting the Conformation of the Hypervariable Loops," J. Mol. Biol., 224:487-499 (1992).
Foster et al., "Secondary glaucoma in patients with juvenile rheumatoid arthritis-associated iridocyclitis," Acta Opthalamol. Scand, 78(5):576-579 (2000).
Fox et al., "Sjogren's Syndrome," Arthritis and Rheumatism, 29:577-85 (1986).
Furst et al., "Adalimumab, a Fully Human Anti-Tumor Necrosis Factor-a Monoclonal Antibody, and Concomitant Standard Antirheumatic Therapy for the Treatment of Rheumatoid Arthritis: Results of STAR (Safety Trial of Adalimumab in Rheumatoid Arthritis)," The Journal of Rheumatology, 30(12):2563-2571 (2003).
Furst et al., "Improvement of the Individual ACR Components in ACR20 Responders in an Adalimumab (Humira™) RA Clinical Trial," Arthritis Rheum, 48(9):S106 (2003).
Furst et al., "Safety and Efficacy of Adalimumab (D2E7), a Fully Human Anti-TNF-a Monoclonal Antibody, Given in Combination with Standard Antirheumatic Therapy: Safety Trial of Adalimumab in Rheumatoid Arthritis," Arthritis Rheum., 46(9):S572 (2002).
Furst et al., "TNF Blockade by the Fully Human Monoclonal Antibody Adalimumab (D2E7), in the Armada Trial Results in Decreases in Serum Matrix Metalloproteinase (MMP) Levels Along with Impressive Clinical Improvement in Refractory RA Patients," Arthritis Rheum., 44(9):S215 (2001).
Genetic Engineering & Biotechnology News, "Top 20 Best-Selling Drugs of 2012," Mar. 5, 2013.
Genovese et al., "Adalimumab efficacy in patients with psoriatic arthritis who failed prior DMARD therapy," Ann Rheum Dis., 64(3):313 (2005).
Gerloni et al., "Infliximab in the treatment of persistently active refractory juvenile idiopathic (chronic) arthritis: A short-term pilot study," Arthritis & Rheumatism 43(9): S256, abstract #1139 (2000).
Giannini et al., "Preliminary definition of improvement in juvenile arthritis," Arthritis & Rheumatism, 40:1202 (1997).
Goodman, "Novel EGFR Inhibitor Added to Radiotherapy Fails to Improve Outcomes in Head and Neck Cancer," ASCO Post 4(19):1-2 (2013).
Gordon et al., "Clinical Response to Adalimumab Treatment in Patients with Moderate to Severe psoriasis: Double-Blind, Randomized Controlled Trial and Open-Label Extension Study," J. Am. Acad. Derm., 55(1):598-606 (2006).
Gorman et al., "Treatment of ankylosing spondylitis by inhibition of tumor necrosis factor alpha," N Engl J Med., 346(18):1349-56 (2002).
Goto et al., "Adalimumab," Medline AC NLM12510366 (2002).
Goto et al., "Adalimumab," Nippon Rinsho (Japanese Journal of Clinical Medicine ), 60(12): 2384-2389 (2002).
Gottlieb, A., "Infliximab for psoriasis," J. Am. Acad. Dermatol. 49(2):S112-117 (2003).
Gottlieb, A., et al., "Infliximab monotherapy provides rapid and sustained benefit for plaquetype psoriasis," J. Am. Acad. Dermatol., 48(6):829-835 (2003).
Granneman et al., "Pharmacokinetic/Pharmacodynamic (PKIPD) Relationships of Adalimumab (Humira™, Abbott) in Rheumatoid Arthritis (RA) Patients during Phase II/III Clinical Trials," Arthritis. Rheum., 48(9):S140 (2003).
Griffiths et al., "Human anti-self antibodies with high specificity from phage display libraries," The EMBO J., 12(2):725-34 (1993).
Grom et al., "Patterns of Expression of Tumor Necrosis Factor a, Tumor Necrosis Factor a, and Their Receptors in Synovia of Patients with Juvenile Rheumatoid Arthritis and Juvenile Spondylarthropathy," Arthritis & Rheumatism, 39(10):1703-1710 (1996).
Halme, "Release of tumor necrosis factor-a by human peritoneal macrophages in vivo and in vitro," Am J Obstet Gynecol, 161:1718 (1989).
Harris et al., "Expression of proinflammatory Genes During Estrogen-Induced Inflammation of the Rat Prostate," Prostate, 44:19-25 (2000).
Hawkins et al., "Selection of Phage Antibodies by Binding Affinity Mimicking Affinity Maturation," J. Mol. Biol., 226:889-896 (1992).
Helfrich et al., "Topical becocalcidiol for the treatment of psoriasis vulgaris: a randomized, placebo-controlled, double-blind, multicentre study," British Journal of Dermatology, 157: 369-374 (2007).
Highlights of Humira Prescribing Information, Abbott Laboratories, North Chicago, IL, USA, pp. 1-53, updated Mar. 2009.
Highlights of Humira Prescribing Information, Abbott Laboratories, North Chicago, IL, USA, pp. 1-70, updated Mar. 2011.
Ho et al., "Genetic epidemiology of psoriatic arthritis," Modern Rheumatology 14(2):91-100, (2004) Abstract only.
Holler et al., "Modulation of Acute Graft-Versus-Host Disease After Allogeneic Bone Marrow Transplantation by Tumor Necrosis Factor a (TNFa) Release in the Course of Pretransplant Conditioning: Role of Conditioning Regimens and Prophylactic Application of a Monoclonal Antibody Neutralizing Human TNFa (MAK 195F)," Blood, 86(3):890-899 (1995).
Holliger et al., "Engineered antibody fragments and the rise of single domains," Nature Biotechnology, 23(9): 1126-1136 (2005).
Holt et al., "Domain Antibodies: Proteins for Therapy," Trends in Biotech, 21(11): 484-490 (2003).
Honkanen et al., "Infliximab Treatment in the refractory chronic uveitis of juvenile idiopathic arthritis (JRA)," Arthritis & Rheumatism, 44:277-390, (2001) abstract #1438.
Hoogenboom et al., "Converting rodent into human antibodies by guided selection," Antibody Engineering, 8:169-185 (1996).
Horneff et al., "TNF-alpha antagonists for the treatment of juvenile-onset spondyloarthritides," Clin Exp Rheumatol, 20(6 Supp 28):S137-42 (2002).
http://www.marketwatch.com/story/biogen-slumps-cdp-571-studyresults-miss-endpoint (Jul. 30, 2002).
Humira (adalimumab) Patient Information Label (Dec. 2002).
Humira (adalimumab). Data Sheet [online]. Abbott Laboratories, Dec. 20, 2002 [retrieved on Jun. 7, 2013]. Retrieved from the Internet: URL: www.fda.gov/downloads/Drugs/DevelopmentApprovalProcess/HowDrugsareDevelopedandApproved/ApprovalApplications/TherapeuticBiologicApplications/ucm092762.pdf.
Humira, Highlights of Prescribing Information, Abbott Laboratories, North Chicago, IL, USA, pp. 1-56, Nov. 2009.
Humira FDA approval letter for PsA, Oct. 3, 2005.
Humira Prescribing Information, Abbott Laboratories, North Chicago, IL, USA, pp. 1-13, Jan. 2003.
Humira Prescribing Information, Abbott Laboratories, North Chicago, IL, USA, pp. 1-33, Sep. 27, 2005.
Humira Prescribing Information, Abbott Laboratories, North Chicago, IL, USA, pp. 1-24, Jul. 30, 2004.
Humira product monograph (Jul. 10, 2012).
Huse et al., "Generation of a large combinatorial library of the immunoglobulin repertoire in phage lambda," Science, 246:1275-81 (1989).

(56) References Cited

OTHER PUBLICATIONS

Immunex Press Release, "First Therapy Approved for Treatment of psoriatic Arthritis," http://www.psoriasis-netz.de/medikamente/etanercept/pm-enbrel.html Jan. (2002).
International Preliminary Examination Report for PCT/US2003/022566 (WO 04/009776).
Iyer et al., "Etanercept for severe psoriasis and psoriatic arthritis: observations on combination therapy," Br. J. Dermatol, 146(1):118-21 (2002).
Jackson, "Immunomodulating drugs in the management of psoriatic arthritis," Am J Clin Dermatol, 2(6):367-75 (2001).
Janeway, "The protein products of MHC class I and class II genes are highly polymorphic," Immunobiology (3rd Edition) 4:24-4:30 (1997).
Janeway, "The structure of a typical antibody molecule," Immunobiology, 5 (2001).
Jespers et al., "Guiding the Selection of Human Antibodies from Phage Display Repertoires to a Single Epitope of an Antigen," Bio/Technology, 12:899-903 (1994).
Jones et al., "Psoriatic arthritis: outcome of disease subsets and relationship of joint disease to nail and skin disease," Br. J. Rheumatol., 33(9):834-839 (1994).
Kaiser et al., "Efficacy of infliximab (Remicade) in the treatment of spondyloarthropathies two case reports," Joint Bone Spine, 68(6):525-7 (2001).
Kalden et al., "Emerging role of anti-tumor necrosis factor therapy in rheumatic diseases," Arthritis Research, 4(2): S34-40 (2002).
Kamarashev et al., "Generalised pustular psoriasis induced by cyclosporin a withdrawal responding to the tumour necrosis factor alpha inhibitor etanercept," Dermatology, 205(2):213-6 (2002).
Kanakoudi-Tsakalidou et al., "Influenza vaccination in children with chronic rheumatic diseases and long-term immunosuppressive therapy," Clinical and Experimental Rheumatology, 19:589-594 (2001).
Katsanos, et al., "Axillary hidradenitis suppurativa successfully treated with infliximab in a Crohn's disease patient," AJG 97:2155-2156 (2002).
Kavanaugh et al., "Adalimumab treatment with and without methotrexate in patients with moderate to severe psoriatic arthritis: results from ADEPT," Ann Rheum Dis., 64(3):325 [FRI0227] (2005).
Kavanaugh et al., "Immune Response is Not Affected by Adalimumab Therapy," Ann. Rheum. Dis., 62(1): 169 (2003).
Kavanaugh et al., "The Armada Trial: 12-Month Efficacy and Safety of Combination Therapy with Adalimumab (D2E7), the First Fully Human Anti-TNF Monoclonal Antibody, and Methotrexate (MTX) in Patients with Active Rheumatoid Arthritis," Ann. Rheum. Dis., 61(1):S168 (2002).
Kavanaugh et al., "Treatment with Adalimumab (D2E7) does not Affect Normal Immune Responsiveness," Arthritis Rheum., 46(9):S132 (2002).
Kaymakcalan et al., "Comparison of Adalimumab (D2E7), Infliximab, and Etanercept in the Prevention of Polyarthritis in the Transgenic Murine Model of Rheumatoid Arthritis," Arthritis Rheum., 46(9):S304 (2002).
Kaymakcalan et al., "Murine Model for Assessing Adalimumab, Inflixmab, and Etanercept to Prevent Polyarthritis," Ann. Rheum. Dis., 62(1):136-7 (2003).
Keffer et al., "Transgenic Mice 1 Expressing Human Tumour Necrosis Factor: A Predictive Genetic Model of Arthritis," EMBO (European Molecular Biology Organization) Journal, 10(13):4025-4031 (1991).
Kempeni, "Preliminary Results of early clinical trials with the fully human anti-TNFα monoclonal antibody D2E7," Ann. Rheum. Dis., 58(1):170-172 (1999).
Kempeni, "Update on D2E7: a fully human anti-tumour necrosis factor a monoclonal antibody," Ann. Rheum. Dis., 59(1):144-145 (2000).
Keystone et al, "Radiographic, clinical and functional outcomes with adalimumab (a human anti-TNF monoclonal antibody) in the treatment of patients with active rheumatoid arthritis on concomitant methotrexate therapy: A randomized, placebo-controlled, 52-week trial," Arthritis Rheum;50(5):1400-1411 (2004).
Keystone et al., "Developing an effective treatment algorithm for rheumatoid arthritis," Rheumatol. 51:v48-v54 (2012).
Keystone et al., "Efficacy and Safety of Adalimumab (D2E7), the Fully Human Anti-TNF Monoclonal Antibody, in MTX Partial Responders: Results of the 24-week Armada Trial," JCR: Journal of Clinical Rheumatology, 8(3):S69 (2002).
Keystone et al., "Subgroup Analysis of Radiographic Progression in RA Patients with Moderate Disease Treated with Adalimumab (Humira®)," Ann. Rheum. Dis., 62(1):169 (2003).
Keystone et al., "Sustained Radiographic Inhibition with Adalimumab (Humira®) over 2 years in Patients with Long Standing Rheumatoid Arthritis (RA)," Arthritis Rheum., 48(9):S315 (2003).
Keystone et al., "The Armada Trial: A Double-Blind Placebo Controlled Trial of the Fully Human Anti-TNF Monoclonal Antibody, Adalimumab (D2E7), in Patients with Active RA on Methotrexate (MTX)," Arthritis & Rheumatism, 44(9):S213 (2001).
Keystone, E., et al., "Radiographic Inhibition of Structural Damage Sustained in Patients with Long-standing Rheumatoid Arthritis Following 3 Years of Treatment with Adalimumab (Humira®) Plus Methotrexate," Abstract 370, Arthritis & Rheumatism, 50 (Suppl. 9):S189 (2004).
Keystone, E., et al., "Subgroup Analysis of Radiographic Progression in RA Patients with Moderate Disease Treated With Adalimumab (Humira®)," Abstract FRI0064, Ann. Rheum. Dis., 63 (2004).
Keystone, et al., "Response to Adalimumab in Patients with Early Versus Late Rheumatoid Arthritis (RA)," Ann. Rheum. Dis., 62(1):170 (2003).
Kietz et al., "Clinical response to etanercept in polyarticular course juvenile rheumatoid arthritis," J. Rheumatology, 28(2):360-362 (2001).
Kirby et al., "Successful treatment of severe recalcitrant psoriasis with combination infliximab and methotrexate," Clin. Exp. Dermatol, 26(1):27-9 (2001).
Kirson, et al., "Matching-adjusted indirect comparison of adalimumab vs etanercept and infliximab for the treatment of psoriatic arthritis," J Med. Econ., 16(4):479-89 (2013).
Klippel et al., "A. Epidemiology, Pathology, and Pathogenesis," Primer on Rheumatic Diseases, 11:155 (1997).
Klippel et al., "A. Juvenile Rheumatoid Arthritis and Juvenile Spondyloarthropathies," Primer on Rheumatic Diseases, 11:393 (1997).
Klippel, et al., "Juvenile Idiopathic Arthritis C. Treatment and Assessment," Primer on Rheumatic Diseases, 13:154-162 (2008).
Koski et al., "Tumor necrosis factor-alpha and receptors for it in labial salivary glands in Sjogren's syndrome," Clin Exp Rheumatol., 19:131 (2001).
Kraetsch et al., "Successful treatment of a small cohort of patients with adult onset of Still's disease with infliximab: first experiences," Annals of the Rheumatic Diseases, 60(3):iii55-iii57 (2001).
Krause, Carey, "Abbott bets on adalimumab in biologics RA market," Chemical Market Reporter, 261(25):12 (Jun. 24, 2002).
Kremer, "Rational Use of New and Existing Disease-Modifying Agents in Rheumatoid Arthritis," Ann. Intern. Med., 134:695-706 (2001).
Kress, Scheldon, "Clinical Review: Abbott, Biologic Licensing Application STN 125057, Adalimumab—For Use in the Treatment of Rheumatoid Arthritis," Center for Biologics Evaluation and Research, available at http://www.fda.gov/ohrms/dockets/ac/03/briefing/3930B1_01_C--Humira.Med.Review.pdf (2002).
Kurschat et al., "Treatment of psoriatic arthritis with etanercept," JAM Acad Dermatology, 44(6): 1052 (2001).
Landenne et al., "Infliximab or etanercept in the treatment of children with refractory juvenile idiopathic arthritis: an open label study," Ann. Rhem. Dis., 62(3):245-247 (2003).
Lahdenne et al., "*Infliximab vs Etanercept in the treatment of severe juvenile chronic arthritis*," Arthritis & Rheumatism, 43(1): S381 abstract #1888 (2001).

(56) References Cited

OTHER PUBLICATIONS

Langley et al., "Evaluating psoriasis with Psoriasis Area and Severity Index, Psoriasis Global Assessment, and Lattice System Physician's Global Assessment," J. Am. Acad. Dermatol., 51(4):563-9 (2004).
Lerner et al., "Antibodies without immunization," Science, 258:1313-14 (1992).
Leusch et al., "Failure to demonstrate TNFa-specific autoantibodies in human sera by ElISA and Western blot," J. Immunol Methods, 139:145-47 (1991).
Lewis et al., "Use of alanine scanning mutagenesis to improve the affinity of an anti gp120 (HIV) antibody," J. Cell. Biochem., 18D:215 (1994).
Lipsky et al., "Infliximab and Methotrexate in the Treatment of Rheumatoid Arthritis," The New England Journal of Medicine, 343(22):1594-1602 (2000).
Lipsy, "Etanercept and its implications for managed care," Am J of Managed Care, 8(6):S194-S200 (2002).
Lorenz et al., "Perspectives for TNF-alpha-targeting therapies," Arthritis Research, 4(3):S17-S24 (2002).
Lorenz et al., "Technology evaluation: Adalimumab, Abbott Laboratories," Current Opinions in Molecular Therapeutics, 4(2): 185-190 (2002).
Low et al., "Mimicking Somatic Hypermutation: Affinity Maturation of Antibodies Displayed on Bacteriophage Using a Bacterial Mutator Strain," J. Mol. Biol., 260:359-368 (1996).
Low, thesis extract, Cambridge University (1996).
MacCallum et al., "Antibody-antigen Interactions: Contact Analysis and Binding Site Topography," J. Mol. Biol., 262:732-745 (1996).
MacDonald et al., "Tumor necrosis factor-alpha and interferon-gamma production measured at the single cell level in normal and inflamed human intestine," Clin. Exp. Immunol., 81:301-305 (1990).
Machold et al., "Adalimumab—a new TNF-a antibody for treatment of inflammatory joint disease," Expert Opin. Biol. Ther., 3(2):351-360 (2003).
Mackiewicz et al., "Dual effects caspase-1, interleukin-1beta, tumour necrosis factor-alpha and nerve growth factor receptor in inflammatory myopathies." Clin. Exp. Rheumatol, 21(1):41-8 (2003).
Mader et al., "Does injectable gold retard radiologic evidence of joint damage in psoriatic arthritis?" Clin. Invest. Med., 18(2):139-143 (1995) [abstract].
Maini et al., "How does infliximab work in rheumatoid arthritis?" Arthrit. Res, 4(2):S22-S28 (2002).
Maksymowych et al., "Canadian Rheumatology Association Consensus on the use of anti-tumor necrosis factor-alpha directed therapies in the treatment of spondyloarthritis," J Rheumatol, 30(6):1356-63 (2003).
Mang et al., "Response of severe psoriasis to infliximab," Dermatology, 204(2):156-7 (2002).
Mangge et al., "Serum cytokines in juvenile rheumatoid arthritis," Arthritis Rheum. 8:211 (1995).
Mangge et al., "Therapeutic experience with infliximab in a patient with polyarticular juvenile idiopathic arthritis and uveitis," Rheumatol Int., 5:258-261 (2003).
Markenson., "Psoriatic Arthritis," In Manual of Rheumatology and Outpatient Orthopedic Disorders: Diagnosis and Therapy, 4(35):279-283 (2000).
Marks et al., "By-Passing Immunization: Building High Affinity Human Antibodies by Chain Shuffling," Nature Biotechnology, 10:779-783 (1992).
Marks et al., "By-passing immunization: Human antibodies from V-gene libraries displayed on phage," J. Mol. Biol., 222:581-97 (1991).
Martinez et al., "Hidradenitis Suppurativa and Crohn's disease: Response to Treatment with Infliximab," Inflammatory Bowel Diseases, 7(4):323-326 (2001).
Marzi et al., "Effect of anti-tumor necrosis factor a on leukocyte adhesion in the liver after hemorrhagic shock: An intravital microscopic study in the rat," Shock, 3(1): 27-33 (1995).
Marzo-Ortega et al., "Early oligoarthritis," Rheum. Dis. Clin. N. Amer., 31(4):627-639 (2005).
Marzo-Ortega et al., "Infliximab is Effective in the Treatment of Resistant Psoriatic Arthritis and Skin Psoriasis: A Clinical and MRI Study," Rheumatology, 41(2):5 (2002).
Marzo-Ortega et al., "Inhibition of tumor necrosis factor alpha and ankylosing spondylitis," N Engl J Med., 348(4):359-61 (2003).
Massarotti et al., "Treatment Patterns in Early-onset Rheumatoid Arthritis (RA): Results from the Sonora Study," Ann. Rheum. Dis., 61(1):S93 (2002).
Mease et al., "Adalimumab therapy in patients with psoriatic arthritis: 24-week results of a phase III study," Arthritis & Rheumatism, 50(12):4097 (2004).
Mease et al., "Psoriatic Arthritis Treatment: Biological Response Modifiers," Annals of the Rheumatic Diseases, 64(2):ii78-ii82 (2005).
Mease, "Cytokine blockers in psoriatic arthritis," Ann Rheum Dis, 60:iii37-iii40 (2001).
Mease, "Etanercept: A new era in the treatment of psoriatic arthritis," Am J of Managed Care, 8(6):S181-S193 (2002).
Mease, "Psoriatic arthritis therapy advances," Current Opinion in Rheumatology, 17(4):426-432 (2005).
Mease, "Targeting therapy in psoriatic arthritis," Drug Discovery Today: Therapeutics Strategies, 1(3):389-396 (2004).
Mease, "Tumour necrosis factor (TNF) in psoriatic arthritis: pathophysiology and treatment with TNF inhibitors," Ann Rheum Dis., 61:298-304 (2002).
Mease, P., et al., "24-Week Efficacy and Safety Results From the Adalimumab Effectiveness in Psoriatic Arthritis Trial (ADEPT)," Rheumatology, 44:OP5 (2005).
Mease, P., et al., "Clinical Efficacy and Safety of Adalimumab for Psoriatic Arthritis: 48-Week Results of ADEPT," Abstract 500, Arthritis & Rheumatism, 52(9) (Suppl.):S215 (2005).
Mease, P., et al., "Enbrel® (Etanercept) in Patients with Psoriatic Arthritis and Psoriasis," Abstract 1835, Arthritis Rheum., 42 (suppl.):S377 (1999).
Mease, P., et al., "Inhibition of Joint Destruction in PsA with Adalimumab: 48-Week Results of ADEPT," Abstract 1699, Arthritis & Rheumatism, 52(9) (Suppl.):S631 (2005).
Medynski, "Phage Display: All Dressed Up and Ready to Role," Bio/Technology, 12:1134-1136 (1994).
Mishra et al., "Histone deacetylase inhibitors modulate renal disease in the MRL-Ipr/lpr mouse," J Clin Invest., 111(4):539-552 (2003).
Moller et al., "Monoclonal antibodies to human tumor necrosis factor a: in vitro and vivo application," Cytokine, 2(3):162-69 (1990).
Moretti et al., "New insights in the pathogenesis of vitiligo: Imbalance of epidermal cytokines at sites of lesions," Pigment Cell Res., 15(2):81-92 (2002).
Moretti et al., "Vitiligo and Epidermal Microenvironment: Possible Involvement of Keratinnocyte-Derived Cytokines," Arch. Dermatol, 138(2):273-4 (2002).
Mori et al., "Peritoneal fluid interleukin-1/b and tumor necrosis factor in patients with benign gynecologic disease," Am J Reprod Immunol, 26:62 (1991).
Mullan et al., "Disease-modifying anti-rheumatic drug therapy and structural damage in early rheumatoid arthritis," Clinical and Experimental Rheumatology, 21(31):S158-164 (2003).
Murota et al., "Disruption of tumor necrosis receptor P55 impairs collagen turnover in experimentally induced sclerodermic skin fibroblasts," Arthritis Rheum, 48(4):1117-25 (2003).
Mussi et al., "Serum TNF-alpha levels correlate with disease severity and are reduced by effective therapy in plaque-type psoriasis," J Bil Reul Homeost Agents, 11(3):115-8 (1997).
Myers et al., "Juvenile arthritis and autoimmunity to type II collagen," Arthrit. Rheum., 8:1775-1781 (2001).
Nadler et al., "11-1 Band TNF-a in prostatic secretions are indicators in the evaluation of men with chronic prostatitis," Journal Urology, 164:214 (2000).

(56) References Cited

OTHER PUBLICATIONS

Neuner et al., "Cytokine release by peripheral blood mononuclear cells is affected by 8-methoxypsoralen plus UV-A," Photochem Photobiol., 59(2):182-188 (1994).
Newland et al., "Rapid response to infliximab in severe pustular psoriasis, von Zumbusch type." Int. J. Derma tol., 41(7):449-52 (2002).
News release, "Abbott Laboratories Initiates Clinical Trials to Explore Use of Humira® (adalimumab) in Psoriasis and Psoriatic Arthritis," Mar. 3, 2003.
Newsire, "Abbott's Humira® (adalimumab) Honored With Prestigious Galen Prize for Innovation in Patient Care," PR Newswire, 1 (2007).
Nickoloff et al., "Cellular Localization of Interleukin-8 and Its Inducer, Tumor Necrosis Factor-alpha in Psoriasis," Am. J. Pathology 138(1):129-140 (1991).
Nilsson, "Antibody engineering," Current Opinion in Structural Biology, 5:450-456 (1995).
O'Quinn et al. "The effectiveness of tumor necrosis factor a antibody (infliximab) in treating recalcitrant psoriasis: A report of 2 cases," Arch. Dermatol., 138(5):644-8 (2002).
Office Action cited during prosecution of U.S. Appl. No. 10/163,657, dated Jun. 18, 2007.
Office Action cited during prosecution of U.S. Appl. No. 10/163,657, dated Sep. 21, 2006.
Office Action cited during prosecution of U.S. Appl. No. 10/422,287, dated Jan. 16, 2009.
Office Action cited during prosecution of U.S. Appl. No. 10/422,287, dated Jul. 18, 2008.
Office Action cited during prosecution of U.S. Appl. No. 11/435,844, dated Aug. 8, 2008.
Office Action cited during prosecution of U.S. Appl. No. 11/435,844, dated Feb. 9, 2009.
Office Action cited during prosecution of U.S. Appl. No. 11/435,844, dated Jan. 16, 2008.
Oh et al., "The potential angiogenic role of macrophages in the formation of choroidal neovascular membranes," Invest Ophthalmol Visual Sci, 40:1891 (1999).
Oh et al., "Treatment with anti-tumor necrosis factor alpha (TNF-alpha) monoclonal antibody dramatically decreases the clinical activity of psoriasis lesions," Journal of the American Academy of Dermatology, 42(5 Pt 1):829-30 (2000).
Orhan et al., "Seminal plasma cytokine levels in the diagnosis of chronic pelvic pain syndrome," Int J Urol, 8:495 (2001).
Orthoclone OKT®3 Sterile Solution (murumonab-CD3) product label (Mar. 2001).
Osbourn et al., "From rodent reagents to human therapeutics using antibody guided selection," Methods, 36:61-68 (2005).
Overton et al., "Peritoneal fluid cytokines and the relationship with endometrosis and pain," Hum Reprod, 11:380 (1996).
Ozaktay et al., "Dorsal root sensitivity to interleukin-1 beta, interleukin-6 and tumor necrosis factor in rats," Eur Spine Journal, 11:467 (2002).
Papp et al., "Approaches to discontinuing efalizumab: an open-label study of therapies for managing inflammatory recurrence," BMC Dermatology, 6:9 (2006).
Partsch et al., "Highly increased levels of tumor necrosis factor-alpha and other proinflammatory cytokines in psoriatic arthritis synovial fluid," J. Rheumatol., 24(3):518-23 (1997).
Partsch et al., "T cell derived cytokines derived in psoriatic arthritis synovial fluids," Annals Rheumatoid Disease, 57:691 (1998).
Patel et al., "Adalimumab: efficacy and safety in psoriasis and rheumatoid arthritis," Dermatologic Therapy, 17(5):427-431 (2004).
Paul, "Immunogenicity and Antigen Structure," Fundamental Immunology, 3(242):292-295 (1993).
Pham et al., "Initiation of biological agents in patients with ankylosing spondylitis: results of a Delphi study by the ASAS Group," Ann Rheum Dis., 62(9):812-6 (2003).

Pincus et al., "Combination Therapy with Multiple Disease-Modifying Antirheumatic Drugs in Rheumatoid Arthritis: A Preventive Strategy," Ann. Intern. Med., 131:768-774 (1999).
Pincus, T., et al., "Evidence from clinical trials and long-term observational studies that disease-modifying anti-rheumatic drugs slow radiographic progression in rheumatoid arthritis: updating a 1983 review," Rheumatology, 41:1346-1356 (2002).
Pitarch et al., "Treatment of psoriasis with adalimumab," Clinical and Experimental Dermatology, 32(1):18-22 (2007).
PR Newswire, "Abbott Laboratories Announces Positive Results of Phase II Humira® (adalimumab) Study in Psoriasis" (Feb. 9, 2004).
PR Newswire, "Cambridge Antibody Technology Interim Results for the Six Months Ended Mar. 31, 2002" (May 20, 2002).
Product Monograph for Humira adalimumab (#00148) CAS Registry Number:331731-18-1, Abbott Laboratories, Jul. 10, 2012: 1-93.
Prous et al., "Annual update 2004/2005—Treatment of musculoskeletal disorders," Drugs of the Future, Prous Science, 30(2):181-232 (2005).
Queen et al., "A humanized antibody that binds to the interleukin 2 receptor," Proc. Natl. Acad. Sci. USA, 86:10029-10033 (1989).
R&D Focus Drug News, "Adalimumab Cambridge Antibody Technology clinical data" (Jul. 2, 2001) ("R&D Focus (2001)").
Rau et al., "2.5-Year Treatment Results with Adalimumab (D2E7), the First Fully Human Anti-TNF Monoclonal Antibody, in Combination with Methotrexate in Active Rheumatoid Arthritis," Ann. Rheum. Dis., 61(1):S55 (2002).
Rau et al., "Adalimumab Inhibits Radiographic Disease Progression in Long-Standing, Rapidly Progressive Rheumatoid Arthritis," Ann. Rheum. Dis., 62(1):191 (2003).
Rau et al., "Combination therapy with the human anti-TNF antibody D2E7 and methotrexate in active chronic polyarthritis," Z. Rheumatol., 58(1): 1/35, F20 (1999).
Rau et al., "Effect and compatibility of repeated intravenous doses of the human anti-TNF antibody D2E7 in patients with chronic polyarthritis," Z. Rheumatol., 58(1):1/41, P12 (1999).
Rau et al., "Erfahrungen mit D2E7," Akt. Rheumatol., 25:83-88 (2000).
Rau et al., "Long-term efficacy and tolerability of multiple I.V. doses of the fully human Anti-TNF-Antibody D2E7 in patients with Rheumatoid Arthritis," Arthritis & Rheumatism, 41(137):S55 (1998).
Rau et al., "Long-term Treatment with the Fully Human Anti-TNF-Antibody D2E7 Slows Radio-graphic Disease Progression in Rheumatoid Arthritis," Arthritis and Rheumatism, 42(9):S400 (1999).
Rau et al., "Low dose prednilsolone therapy (LDPT) retards radiographically detectable destruction in early rheumatoid arthritis—Preliminary results of a multicenter, randomized, parallel, double blind study," Z. Rheumatol., 59(2)11/90-11/96 (2000).
Rau et al., "Treatment with Adalimumab (D2E7), the Fully Human Anti-Tnf Monoclonal Antibody, Slows Radiographic Disease Progression in Rheumatoid Arthritis: Results of a 12-Month Study," J. Clin. Rheum., 8:S78 (2002).
Rau, "Adalimumab (a fully human anti-tumour necrosis factor a monoclonal antibody) in the treatment of active rheumatoid arthritis: the initial results of five trials," Ann. Rheum. Dis., 61(2)ii70-ii73 (2002).
Rau, "Experiments with D2E7," Z. Rheumatol., 58(1):1-21, S51 (1999).
Reilly et al., "Use of genetic knockouts to modulate disease expression in a murine model of lupus, MRUipr mice," Immunologic Research, 25(2):143-153 (2002).
Reimold, "New indications for treatment of chronic inflammation by TNF-alpha blockade," Am J Med Sci., 325(2):75-92 (2003).
Reinhart et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," Crit. Care. Med., 24(5):733-742 (1996).
Remicade (Infliximab) Drug Information: Uses, Side Effects, Drug Interactions and Warnings http://www.rxlist.com/remicadedrug.htm.

(56) References Cited

OTHER PUBLICATIONS

Remicade (infliximab) product information Feb. 1, 2002, retrieved from http://www.drugbank.ca/system/fda_labels/DB00065.pdf?1265922797.
Remicade (infliximab) Product Label (Jun. 2002).
Remicade™ (infliximab) Aug. 1998 Label.
Remicade™ (infliximab) Nov. 10, 1999 Approval Letter.
Reuss-Borst et al., "Sweet's syndrome associated with myelodysplasia: possible role of cytokines in the pathogenesis of the disease," Br. J. Haematol., 84(2):356-8 (1993).
Revenga, F., et al., "Treatment of recalcitrant psoriasis with infliximab," Actas Dermo-Sifiliograficas, 95.1:44-50 (2004).
Revicki et al., "Treatment with Adalimumab (D2E7), a Fully Human Anti-TNF Monoclonal Antibody, Improves Physical Function, Vitality, and Mental Health While Reducing Bodily Pain in Patients with Active Rheumatoid Arthritis (RA)," Arthritis Rheum., 46(9):S537 (2002).
Richette et al. "Sensory Neuropathy revealing a necrotizing vasculitis during infliximab therapy for rheumatoid arthritis," J. Rheumatol. 31:2079-2081 (2004).
Riechmann et al., "Phage Display and Selection of a Site-Directed Randomized Single-Chain Antibody Fv Fragment for Its Affinity Improvement," Biochemistry, 32:8848-8855 (1993).
Ritchlin et al., "Patterns of cytokine productions in psoriatic synovium," J. Rheumatol, 25:1544 (1998).
Rosenberg, Daniel, "Abbott sees new uses for rheumatoid arthritis drug [D2E7]," FirstWord Pharma (Sep. 9, 2002).
Rudikoff et al., "Single amino acid substitution altering antigen-binding specificity," Proc. Natl. Acad. Sci. USA, 79(6):1979-1983 (1982).
Ruperto et al., "A randomized, placebo-controlled trial of infliximab plus methotrexate for the treatment of polyarticular-course juvenile rheumatoid arthritis," Arthr. Rheum 56:3096-3106 (2007).
Ruperto, "48-Week Data From the Study of Adalimumab in Children With Juvenile Rheumatoid Arthritis (JRA)," Ann. Rheum. Dis., 65(2):56 (2006).
Russell-Jones et al., "High-dose interferon and the U.K. guidelines for cutaneous melanoma," Br. J. Dermatol.,147(4):832-4 (2002).
Salfeld et al., "Generation of Fully Human Anti-TNF Antibody D2E7," Arthritis Rheum., 41(9):S57 (1998).
Sandborn et al., "An engineered human antibody to TNF (CDP571) for active Crohn's disease: a randomized double-blind placebo-controlled trial," Gastroenterology, 120:1330-1338 (2001).
Sandborn et al., "CDP571, a humanised monoclonal antibody to tumour necrosis factor α, for moderate to severe Crohn's disease: a randomized, double blind, placebo controlled trial," Gut, 53:1485-1491 (2004).
Sandborn et al., "Etanercept for Active Crohn's Disease: a Randomized, Double-blind, Placebo-Controlled Trial," Gastroenterol, 121:1088-1094 (2001).
Santora et al., "Characterization of Noncovalent Complexes of Recombinant Human Monoclonal Antibody and Antigen Using Carbon Exchange, Size Exclusion Chromatography,and BIAcore," Analytical Biochemistry, 299(2):119-129 (2001).
Santora et al., "Characterization of Recombinant Human Monoclonal Tissue Necrosis Factor-a Antibody Using Cation-Exchange HPLC and Capillary Isoelectric Focusing," Analytical Biochemistry, 275:98-108 (1999).
Schattenkirchner et al, "Efficacy and Tolerability of Weekly Subcutaneous Injections of the Fully Human Anti-TNF-Antibody D2E7 in Patients with Rheumatoid Arthritis—Results of a Phase I Study," Arthritis and Rheumatism, 41(9):S57 (1998).
Schattenkirchner et al., "Long-term Use of the Fully Human Anti-TNF Antibody Adalimumab (D2E7) in Dmard-refractory Rheumatoid Arthritis," EULAR, Prague, Czech Republic, Jun. (2001).
Schattenkirchner et al., "Long-term Use of the Fully Human Anti-TNF Antibody D2E7 in Combination with Methotrexate in Active Rheumatoid Arthritis," EULAR 43(9) (suppl.) S228 (2000).
Schattenkirchner et al., "Phase 1 study on the effectiveness and compatibility of weekly subcutaneous injections of the human anti-TNF antibody D2E7 in chronic polyarthritis," Z.Rheumatol., 58(1):1-42, P14 (1999).
Scheinfeld, "Adalimumab (Humira): A Review," J. Drugs Dermatol, 2:375-377 (2003).
Schiff et al., "A Randomized, Controlled, Safety Trial of Adalimumab (D2E7), a Fully Human Anti-TNF Monoclonal Antibody, Given to RA Patients in Combination with Standard Rheumatologic Care: The STAR (Safety Trial of Adalimumab in Rheumatoid Arthritis) Trial," Ann. Rheum. Dis., 61(1):S169 (2002).
Schiff et al., "Efficacy of Adalimumab Measured by the Disease Activity Score 28 (DAS28) and EULAR Response Criteria," Ann. Rheum. Dis., 62(1):170 (2003).
Schiff et al., "Malignancies in Rheumatoid Arthritis (RA) Clinical Trials with Adalimumab (Humira)," Arthritis Rheum., 48(9):S700 (2003).
Schiff et al., "Rates of Infection in Adalimumab Rheumatoid Arthritis Clinical Trials," Ann. Rheum. Dis., 62(1):184 (2003).
Schiff et al., "Sustained Efficacy of Adalimumab (Humira™) Plus Methotrexate in Rheumatoid Arthritis (RA) Patients," Arthritis Rheum., 48(9):S314 (Poster 740) (2003).
Schnarr et al., "Anti-tumour necrosis factor (TNF)-alpha therapy in undifferentiated spondyloarthropathy," Clin Exp Rheumatol, 20(6 Supp 28):S126-9 (2002).
Schopf et al., "Treatment of psoriasis with the chimeric monoclonal antibody against tumor necrosis factor a, infliximab," J. Am. Acad. Dermatol, 46(6):886-91 (2002).
Shanahan et al., "Tumor Necrosis Factor-α Blockade: A Novel Therapy for Rheumatic Disease," Clin. Immunol. 103:231-242 (2002).
Shealy et al., "Characterization of golimumab, a human monoclonal antibody specific for human tumor necrosis factor alpha," mAbs, 2(4):1-12 (2010).
Shikiar et al., "The validity and responsiveness of three quality of life measures in the assessment of psoriasis patients: results of a phase II study," Health and Quality of Life Outcomes 4:71 (2006).
Shvidel et al., "Cytokine release by activated T-cells in large granular lymphocytic leukemia associated with autoimmune disorders," Hematol J., 3:32 (2002).
Sibilia, "Combination therapy for rheumatoid arthritis," Ann. Med. Interne., 153(1):41-52 (2002).
Siegel et al., "Evidence of Effects of a TNF Blocking Agent in ACR20 Non-Responders," Arthritis Rheum., 48(9):S127 (2003).
Sieper et al., "New treatment options in ankylosing spondylitis: a role for anti-TNFalpha therapy," Ann Rheum Dis., 60(3):iii58-61 (2001).
Sieper, J. & Braun, J., "Anti-TNF agents for the treatment of spondyloarthropathies," Expert Opinion on Emerging Drugs, 7(2):235-246 (2002) ("Sieper (2002)").
Simon et al., "Studies on efficacy in psoriasis and psoriatic arthritis initiated," Dermatol. Psychosom., 4:100-102 (2003).
Slatko, "Contender to the crown," MedAdNews, 29(7):1-3 (2010).
Smith, "Ibuprofen in psoriatic arthritis," Arthritis Rheum., 23(8):961-962 (1980).
Smolen et al., "A Comparison of the SDAI and DAS28 as Measures of Response in Adalimumab (Humira™) Clinical Trials in Rheumatoid Arthritis (RA)," Arthritis Rheum., 48(9):S107 (2003).
Smolen et al., "Objectives and Strategies for Rheumatoid Arthritis Therapy: Yesterday vs. Today," Drugs of Today, 39(B):3-8 (2003).
Spencer-Green, "Etanercept (Enbrel): update on therapeutic use," Ann Rheum Dis., 59(1):i46-i49 (2000).
St. Clair, "Infliximab treatment for rheumatic disease: clinical and radiological efficacy," Ann Rheum Dis, 61(2):ii67-ii69 (2002).
Stokes et al., "Potential of tumor necrosis factor neutralization strategies in Rheumatologlc disorders other than rheumatoid arthritis," Semin Arthritis Rheum., 33(1):1-18 (2003).
Stone et al., "Clinical and imaging correlates of response to treatment with infliximab in patients with ankylosing spondylitis," J Rheumatol., 28(7):1605-14 (2001).
Strand et al., "Adalimumab Improves Health-related Quality of Life in Rheumatoid Arthritis Patients," Ann. Rheum. Dis., 62(1):356 (2003).

(56) References Cited

OTHER PUBLICATIONS

Strand et al., "Improvement in Health-related Quality of Life, Health Utility, and Fatigue in Patients with Active Rheumatoid Arthritis (RA) on Adalimumab (Humira™, Abbott) Therapy," Arthritis Rheum., 48(9):S402 (2003).
Strand et al., "Treatment with Adalimumab (D2E7), a Fully Human Anti-TNF Monoclonal Antibody, Improves Physical Function and Health Related Quality of Life (HRQOL) in Patients with Active Rheumatoid Arthritis (RA)," Ann. Rheum. Dis., 61(1):S175 (2002).
Studnicka-Benke et al., "Tumor necrosis factor alpha and its soluble receptors parallel clinical disease and autoimmune activity in systemic lupus erythematosus," Br J Rheumatol., 35:1067 (1996).
Sun et al., "Bowel necrosis induced by tumor necrosis factor in rats is mediated by platelet-activating factor," J. Clin. Invest., 81:1328-1331 (1988).
Sun et al., "Individually Distinct Ig Homology Domains in PECAM-1 Regulate Homophilic Binding and Modulate Receptor Affinity," J. Biol. Chem., 271:11090-11098 (1996).
Takematsu, "Absence of tumor necrosis factor-alpha in suction blister fluids and stratum corneum from patients with psoriasis," Arch Dermatol Res., 281(6):398-400 (1989).
Taketani et al., "Comparison of cytokine levels and embryo toxicity in peritoneal fluid in infertile women with untreated or treated endometrosis," Am J Obstet. Gynecol., 167:265 (1992).
Thomas, Taber's Cyclopedic Medical Dictionary, 13:118-119 (1977).
Thompson et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," J. Mol. Biol., 256:77-88 (1996).
Thomson, "Abbott seeks U.S. And E.U. approval for D2E7 in rheumatoid arthritis," Reuters Drug News, Apr. 10, 2002, Retrieved from https ://integrity.thomsonpharma.com/integrity/xmlxsI/pk_ref_list.xml_show_ficha_ref?p_ref id=662437.
Tobin et al., "TNF alpha inhibitors in the treatment of psoriasis and psoriatic arthritis," Biodrugs: Clinical Immunotherapeutics, Biopharmaceuticals and Gene Therapy, 19(1):47-57 (2005).
Tomlinson et al., "The Repertoire of Human Germline VH Sequences Reveals about Fifty Groups of VH Segments with Different Hypervariable Loops," J. Mol. Biol., 227:776-798 (1992).
Tomlinson et al., "The structural repertoire of the human VK domain," The EMBO Journal, 14(18):4628-4638 (1995).
Tracey et al., "Shock and tissue injury induced by recombinant human cachectin," Science, 234:470-474 (1986).
Tracey et al., "Tumor Necrosis Factor: A Pleiotropic Cytokine and Therapeutic Target," Annu. Rev. Med., 45:491-503 (1994).
Tsutsumimoto et al., "TNF-a and IL-1 B Suppress N-Cadherin Expression in MC3T3-E1 Cells," J Bone Miner Res., 14:1751 (1999).
Tugwell et al., "Adalimumab Improves Utility and Quality-adjusted Life Days in Rheumatoid Arthritis," Ann. Rheum. Dis., 62(1):107-8 (2003).
Tugwell et al., "Relationship Between ACR Response and HRQL in Adalimumab Clinical Trials," Ann. Rheum. Dis., 62(1):536 (2003).
Tutuncu et al., "Anti-TNF therapy for other inflammatory conditions," Clin. Exp. Rheumatol., 20(6Suppl28):S146-51 (2002).
Tyring et al., "Efficacy and Safety of Humira Every-Other-Week Dosing: Pooled Clinical Trial Experience," Abstract, Presented at the 21st World Congress of Dermatology, Buenos Aires, Argentina, Sep. 30- Oct. 5, 2007.
Ueda et al., "Two Mouse Monoclonal Antibodies Detecting Two Different Epitopes of an Activated Lymphocyte Antigen on Adult T-Cell Leukemia Cells," Cancer Res. 45:1314-1319 (1985).
Vajdos et al., "Comprehensive Functional Maps of the Antigen-binding Site of an Anti-ErbB2 Antibody Obtained with Shotgun Scanning Mutagenesis," J. Mol. Biol., 320:415-428 (2002).
Van de Putte et al., "Adalimumab (D2E7) Monotherapy in the Treatment of Patients with Severely Active Rheumatoid Arthritis (RA)," Arthritis Rheum., 46(9):S171 (2002).
Van de Putte et al., "A placebo-controlled phase 1 study of the human anti-TNP-antibody D2E7 in patients with active chronic polyarthritis," Z. Rheumatol., 58(1):1-34, F19 (1999).
Van de Putte et al., "A Single Dose Placebo Controlled Phase I Study of the Fully Human Anti-TNF Antibody D2E7 in Patients with Rheumatoid Arthritis," Arthritis Rheum., 41:S57 (1998).
Van De Putte et al., "Adalimumab (D2E7), the Fully Human Anti-TNF Monoclonal Antibody, in the Treatment of Patients with Rheumatoid Arthritis Who Failed Previous DMARD Therapy: Efficacy and Safety Results from a 6-Month Phase III Study," JCR, 8(3):S89 (2002).
Van de Putte et al., "Adalimumab," TNFa-Inhibition in the Treatment of Rheumatoid Arthritis, 71-93 (2003).
Van de Putte et al., "Efficacy and Safety of Adalimumab (D2E7), the First Fully Human Anti-TNF Monoclonal Antibody, in Patients with Rheumatoid Arthritis Who Failed Previous DMARD Therapy: 6-Month Results from a Phase III Study," Ann. Rheum. Dis., 61(1):S168 (2002).
Van de Putte et al., "Efficacy and safety of the fully human anti-tumour necrosis factor a monoclonal antibody adalimumab (D2E7) in DMARD refractory patients with rheumatoid arthritis: a 12 week, phase II study," Ann. Rheum. Dis., 62:1168-1177 (2003).
Van de Putte et al., "Efficacy of the Fully Human anti-TNF Antibody D2E7 in Rheumatoid Arthritis," Arthritis & Rheumatism, 42(1977):S400 (1999).
Van de Putte et al., "One Year Efficacy Results of the Fully Human Anti-TNF Antibody D2E7 in Rheumatoid Arthritis," Arthritis Rheum., 43(9):S269 (2000).
Van de Putte et al., "Sustained 5-Year Efficacy of Adalimumab (Humira) Monotherapy in DMARD-Refractory rheumatoid arthritis (RA)," Arthritis Rheum., 48(9):S314 (2003).
Van den Bosch et al., "Crohn's disease associated with spondyloarthropathy: effect of TNF-alpha blockade with infliximab on articular symptoms," Lancet. 356(9244):1821-2 (2000).
Van den Bosch et al., "Effects of a loading dose regimen of three infusions of chimeric monoclonal antibody to tumour necrosis factor a (infliximab) in spondyloarthropathy: an open pilot study," Annal. Rheum. Dis. 59:428-433 (2000).
van der Heijde, D., et al., "Psoriatic arthritis imaging: a review of scoring methods," Ann. Rheum. Dis., 64 (Suppl. II):ii61-ii64 (2005).
van der Poll et al., "Effect of postponed treatment with an anti-tumour necrosis factor (TNF) F(ab')2 fragment on endotoxin-induced cytokine and neutrophil responses in chimpanzees," Clin. Exp. Immunol., 100:21-25 (1995).
van Deventer et al., "Transmembrane TNF-alpha, induction of apoptosis, and the efficacy of TNF-targeting therapies in Crohn's disease." Gastroenterol, 121:1242-1246 (2001).
van Riel et al., "Long-Term Treatment with Adalimumab (D2E7) Using Background Methotrexate in Active Rheumatoid Arthritis: Results of a 3 Year Study," Arthritis Rheum., 46(9):S534 (2002).
van Riel, "A Comparison of CRP and ESR to Measure the DAS28 in Adalimumab Clinical Trials," Ann Rheum Dis., 62:169-70 (Poster THU0199). (2003).
Vasilli, "The pathophysiology of tumor necrosis factors", Annu. Rev. Immunol., 10:411-452 (1992).
Vaughan et al., "Human antibodies by design," Nature Biotechnology, 16:535-539 (1998).
Veale et al., "Classification of clinical subsets in psoriatic arthritis," Br. J. Rheumatol. 33(2):133-138 (1994).
Velagapudi et al., "Pharmacokinetics of Adalimumab (D2E7), a Fully Human Anti-TNF-a Monoclonal Antibody, Following a Single Intravenous Injection in Rheumatoid Arthritis Patient Treated with Methotrexate," Arthritis Rheum., 46(9):S133 (2002).
Velagapudi, et al., "Effect of Methotrexate (MTX) Coadministration on the Pharmacokinetics (PK) of Adalimumab (Humira™, Abbott) Following a Single Intravenous (iv) Injection," Arthritis Rheum., 48(9):S141 (2003).
Venn et al., "Elevated synovial fluid levels of interleukin-6 and tumor necrosis factor associated with early experimental canine osteoarthritis," Arthritis Rheum., 36:819-826 (1993).

(56) References Cited

OTHER PUBLICATIONS

Victor et al., "TNF-alpha and apoptosis: implications for the pathogenesis and treatment of psoriasis," J Drugs Dermatol, 1(3):264-75 (2002).
Vitali et al., "Preliminary criteria for the classification of sjogren's syndrome," Arthritis Rheum, 36:3407 (1993).
Wakefield et al., "The role of cytokines in the pathogenesis of inflammatory eye disease," Cytokine, 4:1 (1992).
Ward et al., "Binding activities of a repertoire of single immunoglobulin variable domains secreted from *Escherichia coli*," Nature, 341:544-546 (1989).
Weinblatt et al., "Adalimumab, a Fully Human Anti-Tumor Necrosis Factor a Monoclonal Antibody, for the Treatment of Rheumatoid Arthritis in Patients Taking Concomitant Methotrexate," Arthritis & Rheumatism, 48(1):35-45 (2003).
Weinblatt et al., "The Armada Trial: Efficacy and Safety of Adalimumab in Patients with Active RA at 24 Months," Ann. Rheum. Dis., 62(1):98 (2003).
Weinblatt et al., "The Armada Trial: Sustained Improvement and Tolerability in Long-Term Follow-Up of Patients Treated with Adalimumab (Humira™)," Arthritis Rheum., 48(9):S314 (2003).
Weisman et al., "A Dose Escalation Study Designed to Demonstrate the Safety, Tolerability and Efficacy of the Fully Human Anti-TNF Antibody, D2E7, Given in Combination with Methotrexate," Arthritis Rheum., 43(9):S391 (2000).
Weisman et al., "Efficacy, Pharmacokinetic, and Safety Assessment of Adalimumab, a Fully Human Anti-Tumor Necrosis Factor-Alpha Monoclonal Antibody, in Adults with Rheumatoid Arthritis Receiving Concomitant Methotrexate: A Pilot Study," Clinical Therapeutics, 25(6): 1700-1721 (2003).
Weisman et al., The Importance of Pain and the Impact of Adalimumab on Pain in RA Patients, Ann. Rheum. Dis., 62(1):351 (2003).
Wellborne et al., "Adalimumab (D2E7), a Fully Human Anti-TNF-a Monoclonal Antibody, Improved Health-Related Quality of Life in Patients with Active Rheumatoid Arthritis Despite Concomitant Methotrexate Therapy," Arthritis Rheum., 46(9):S518 (2002).
Wells et al., "Incidence of Injection-Site Reactions Associated with Adalimumab (D2E7) Give Subcutaneously for at Least 6 Months: A Retrospective Analysis of 4 Phase II/III Clinical Trials," Arthritis Rheum., 46(9):S171 (2002).
Wells et al., "Injection-site Reactions in Adalimumab Rheumatoid Arthritis (RA) Pivotal Clinical Trials," Ann. Rheum. Dis., 62(1):411 (2003).
Westacott et al., "Tumor necrosis factor-a receptor expression on chondrocytes isolated from human articular cartilage," J. Rheumatology, 21:1710 (1994).
Williams et al., "Anti-tumor necrosis factor ameliorates joint disease in murine collagen-induced arthritis," Proc Natl Acad Sci USA, 89:9784 (1992).
Winter et al., "Humanized antibodies," Immunology Today, 14(6):243-246 (1993).
Winter et al., "Making Antibodies by Phage Display Technology," Annu. Rev. Immunol., 12:433-455 (1994).
Wollina et al., "Treatment of recalcitrant psoriatic arthritis with anti-tumor necrosis factor-alpha antibody," J. Eur. Acad. Dermatology and Venereology, 16(2):127-129 (2002).
Woon et al., "Kinetics of cytokine production in experimental autoimmune anterior uveitis (EAAU)," Current Eye Research, 17:955 (1998).
Yamauchi et al., "Adalimubab in the Management of Hidradenitis Suppurativa," J Am Acad. Deam., AB41:P504 (2007).
Yazici et al., "A preliminary study of etanercept in the treatment of severe, resistant psoriatic arthritis," Clinical and Experimental Rheumatology, 18:732-734 (2000).
Yazici, et al., "Etanercept in the treatment of severe, resistant psoriatic arthritis: Continued efficacy and changing patterns of use after two years," Clin Exp Rheumatol. Jan.-Feb. 2000;20(1):115.
Zabraniecki et al., "TNF alpha inhibition in psoriatic arthritis: cause for hope," Joint Bone Spine Mar.;68(2):106-8 (2001).
Zou et al., "Immunological basis for the use of TNF-alpha-blocking agents in ankylosing spondylitis and immunological changes during treatment," Clin Exp Rheumatol. Nov.-Dec.-20(6 Suppl 2S):S34-7 (2002).

\* cited by examiner

USES AND COMPOSITIONS FOR TREATMENT OF PSORIATIC ARTHRITIS

RELATED APPLICATIONS

This application claims the benefit of priority to U.S. provisional patent application No. 60/790,909, filed on Apr. 10, 2006; U.S. provisional patent application No. 60/809,770, filed on May 30, 2006; U.S. provisional patent application No. 60/815,489, filed on Jun. 20, 2006; U.S. provisional patent application No. 60/858,376, filed on Nov. 10, 2006; U.S. provisional patent application No. 60/899,262, filed on Feb. 2, 2007; and U.S. provisional patent application No. 60/909,683, filed on Apr. 2, 2007. The contents of all the above-mentioned priority applications are hereby incorporated by reference in their entirety.

BACKGROUND

Tumor necrosis factor has been implicated in the pathophysiology of psoriatic arthritis (Partsch et al. (1998) *Ann Rheum Dis.* 57:691; Ritchlin et al. (1998) *J Rheumatol.* 25:1544). As referred to herein, psoriatic arthritis (PsA) or psoriasis associated with the skin, refers to chronic inflammatory arthritis which is associated with psoriasis. Psoriasis is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis. The TNFα inhibitor, or TNFα antibody, or antigen-binding fragment thereof, of the invention can be used to treat PsA.

SUMMARY OF THE INVENTION

There remains a need for an effective and safe treatment option for patients suffering from psoriatic arthritis. The instant invention provides improved methods and compositions for treating psoriatic arthritis. The invention further provides a means for treating certain subpopulations of patients who have psoriatic arthritis, including patients who have failed therapy or lost responsiveness to treatment with TNFα inhibitors. The invention further provides a means by which the efficacy of a TNFα inhibitor for the treatment of psoriatic arthritis can be determined. The invention also includes methods for treating certain types of psoriatic arthritis, e.g., early psoriatic arthritis. Each of the examples described herein describes methods which can be used to determine whether a TNFα inhibitor is effective for treating the given disorder.

In some aspects, the present invention provides a method of determining the efficacy of a TNFa inhibitor for treating psoriatic arthritis in a subject comprising determining an ACR20 response of a patient population having psoriatic arthritis and who was administered the TNFa inhibitor, wherein an ACR20 response in at least about 59% of the patient population indicates that the TNFa inhibitor is an effective TNFa inhibitor for the treatment of psoriatic arthritis in a subject. In various embodiments, the method further comprises administering the effective TNFa inhibitor to a subject to treat psoriatic arthritis. In some embodiments, an ACR20 response in at least about 61% of the patient population indicates that the TNFa inhibitor is an effective TNFa inhibitor for the treatment of psoriatic arthritis in a subject. In other embodiments, an ACR20 response in at least about 65% of the patient population indicates that the TNFa inhibitor is an effective TNFa inhibitor for the treatment of psoriatic arthritis in a subject. In yet other embodiments, an ACR20 response in at least about 69% of the patient population indicates that the TNFa inhibitor is an effective TNFa inhibitor for the treatment of psoriatic arthritis in a subject. In some embodiments, an ACR20 response in at least about 72% of the patient population indicates that the TNFa inhibitor is an effective TNFa inhibitor for the treatment of psoriatic arthritis in a subject. In other embodiments, an ACR20 response in at least about 75% of the patient population indicates that the TNFa inhibitor is an effective TNFa inhibitor for the treatment of psoriatic arthritis in a subject.

In some aspects, the present invention provides a method of treating psoriatic arthritis in a subject comprising administering an effective TNFα inhibitor to the subject such that psoriatic arthritis is treated, wherein the effective TNFα inhibitor was previously identified as achieving an ACR20 response in at least about 59% of the patient population. In some aspects, the present invention provides for the use of an effective TNFα inhibitor in the manufacture of a medicament for the treatment of psoriatic arthritis in a subject, wherein the effective TNFα inhibitor was previously identified as achieving an ACR20 response in at least about 59% of the patient population who was administered the effective TNFα inhibitor. In some embodiments, the effective TNFα inhibitor was previously identified as achieving an ACR20 response in at least about 61% of the patient population having psoriatic arthritis. In other embodiments, the effective TNFα inhibitor was previously identified as achieving an ACR20 response in at least about 65% of the patient population having psoriatic arthritis. In yet other embodiments, the effective TNFa inhibitor was previously identified as achieving an ACR20 response in at least about 69% of the patient population having psoriatic arthritis. In some embodiments, the effective TNFα inhibitor was previously identified as achieving an ACR20 response in at least about 72% of the patient population having psoriatic arthritis. In other embodiments, the effective TNFa inhibitor was previously identified as achieving an ACR20 response in at least about 75% of the patient population having psoriatic arthritis.

In some aspects, the present invention provides a method of determining the efficacy of a TNFa inhibitor for treating psoriatic arthritis in a subject comprising: determining a PASI50 response of a patient population having psoriatic arthritis and who was administered the TNFa inhibitor, wherein a PASI50 response in at least about 55% of the patient population indicates that the TNFa inhibitor is an effective TNFa inhibitor for the treatment of psoriatic arthritis in a subject. In some embodiments, the method further comprises administering the effective TNFa inhibitor to a subject to treat psoriatic arthritis. In some embodiments, a PASI50 response in at least about 60% of the patient population indicates that the TNFa inhibitor is an effective TNFa inhibitor for the treatment of psoriatic arthritis in a subject. In other embodiments, a PASI50 response in at least about 65% of the patient population indicates that the TNFa inhibitor is an effective TNFa inhibitor for the treatment of psoriatic arthritis in a subject. In yet other embodiments, a PASI50 response in at least about 70% of the patient population indicates that the TNFa inhibitor is an effective TNFa inhibitor for the treatment of psoriatic arthritis in a subject. In some embodiments, a PASI50 response in at least about 75% of the patient population indicates that the TNFa inhibitor is an effective TNFa inhibitor for the treatment of psoriatic arthritis in a subject. In other embodiments, a PASI50 response in at least about 80% of the patient population indicates that the TNFa inhibitor is an effective TNFa inhibitor for the treatment of psoriatic arthritis in a subject.

In some aspects, the invention provides a method of treating psoriatic arthritis in a subject comprising administering an effective TNFa inhibitor to the subject such that psoriatic arthritis is treated, wherein the effective TNFa inhibitor was previously identified as achieving a PASI50 response in at least about 55% of the patient population. In other aspects, the invention provides for the use of an effective TNFa inhibitor in the manufacture of a medicament for the treatment of psoriatic arthritis in a subject, wherein the effective TNFa inhibitor was previously identified as achieving a PASI50 response in at least about 55% of the patient population who was administered the effective TNFa inhibitor. In some embodiments, the effective TNFa inhibitor was previously identified as achieving a PASI50 response in at least about 60% of the patient population having psoriatic arthritis. In other embodiments, the effective TNFa inhibitor was previously identified as achieving a PASI50 response in at least about 65% of the patient population having psoriatic arthritis. In yet other embodiments, the effective TNFa inhibitor was previously identified as achieving a PASI50 response in at least about 70% of the patient population having psoriatic arthritis. In some embodiments, the effective TNFa inhibitor was previously identified as achieving a PASI50 response in at least about 75% of the patient population having psoriatic arthritis. In yet other embodiments, the effective TNFa inhibitor was previously identified as achieving a PASI50 response in at least about 80% of the patient population having psoriatic arthritis.

In some aspects, the present invention provides a method of determining the efficacy of a TNFa inhibitor for treating psoriatic arthritis in a subject comprising: determining a PASI90 response of a patient population having psoriatic arthritis and who was administered the TNFa inhibitor, wherein a PASI90 response in at least about 43% of the patient population indicates that the TNFa inhibitor is an effective TNFa inhibitor for the treatment of psoriatic arthritis in a subject. In some embodiments, the method further comprises administering the effective TNFa inhibitor to a subject to treat psoriatic arthritis. In some embodiments, a PASI90 response in at least about 50% of the patient population indicates that the TNFa inhibitor is an effective TNFa inhibitor for the treatment of psoriatic arthritis in a subject. In some embodiments, a PASI90 response in at least about 55% of the patient population indicates that the TNFa inhibitor is an effective TNFa inhibitor for the treatment of psoriatic arthritis in a subject. In other embodiments, a PASI90 response in at least about 60% of the patient population indicates that the TNFa inhibitor is an effective TNFa inhibitor for the treatment of psoriatic arthritis in a subject. In yet other embodiments, a PASI90 response in at least about 65% of the patient population indicates that the TNFa inhibitor is an effective TNFa inhibitor for the treatment of psoriatic arthritis in a subject. In some embodiments, a PASI90 response in at least about 70% of the patient population indicates that the TNFa inhibitor is an effective TNFa inhibitor for the treatment of psoriatic arthritis in a subject. In still yet other embodiments, a PASI90 response in at least about 75% of the patient population indicates that the TNFa inhibitor is an effective TNFa inhibitor for the treatment of psoriatic arthritis in a subject.

In some aspects, the present invention provides a method of treating psoriatic arthritis in a subject comprising administering an effective TNFa inhibitor to the subject such that psoriatic arthritis is treated, wherein the effective TNFa inhibitor was previously identified as achieving a PASI90 response in at least about 43% of the patient population. In some aspects, the present invention provides for the use of an effective TNFa inhibitor in the manufacture of a medicament for the treatment of psoriatic arthritis in a subject, wherein the effective TNFa inhibitor was previously identified as achieving a PASI90 response in at least about 43% of the patient population who was administered the effective TNFa inhibitor. In some embodiments, the effective TNFa inhibitor was previously identified as achieving a PASI90 response in at least about 50% of the patient population. In other embodiments, the effective TNFa inhibitor was previously identified as achieving a PASI90 response in at least about 55% of the patient population. In other embodiments, the effective TNFa inhibitor was previously identified as achieving a PASI90 response in at least about 60% of the patient population. In still yet other embodiments, the effective TNFa inhibitor was previously identified as achieving a PASI90 response in at least about 65% of the patient population. In some embodiments, the effective TNFa inhibitor was previously identified as achieving a PASI90 response in at least about 70% of the patient population. In some embodiments, the effective TNFa inhibitor was previously identified as achieving a PASI90 response in at least about 75% of the patient population.

In some aspects, the present invention provides a method of determining the efficacy of a TNFa inhibitor for treating psoriatic arthritis in a subject comprising: determining a PASI100 response of a patient population having psoriatic arthritis and who was administered the TNFa inhibitor, wherein a PASI100 response in at least about 10% of the patient population indicates that the TNFa inhibitor is an effective TNFa inhibitor for the treatment of psoriatic arthritis in a subject. In some embodiments, the method of the present invention further comprises administering the effective TNFa inhibitor to a subject to treat psoriatic arthritis. In some embodiments, a PASI100 response in at least about 20% of the patient population indicates that the TNFa inhibitor is an effective TNFa inhibitor for the treatment of psoriatic arthritis in a subject. In some embodiments, a PASI100 response in at least about 30% of the patient population indicates that the TNFa inhibitor is an effective TNFa inhibitor for the treatment of psoriatic arthritis in a subject. In other embodiments, a PASI100 response in at least about 40% of the patient population indicates that the TNFa inhibitor is an effective TNFa inhibitor for the treatment of psoriatic arthritis in a subject. In yet other embodiments, a PASI100 response in at least about 45% of the patient population indicates that the TNFa inhibitor is an effective TNFa inhibitor for the treatment of psoriatic arthritis in a subject.

In some aspects, the present invention provides a method of treating psoriatic arthritis in a subject comprising administering an effective TNFa inhibitor to the subject such that psoriatic arthritis is treated, wherein the effective TNFa inhibitor was previously identified as achieving a PASI100 response in at least about 10% of the patient population. In yet other aspects, the present invention provides for the use of an effective TNFa inhibitor in the manufacture of a medicament for the treatment of psoriatic arthritis, wherein the effective TNFa inhibitor was previously identified as achieving a PASI100 response in at least about 10% of the patient population who was administered the effective TNFa inhibitor. In some embodiments, the effective TNFa inhibitor was previously identified as achieving a PASI90 response in at least about 20% of the patient population. In other embodiments, the effective TNFa inhibitor was previously identified as achieving a PASI90 response in at least about 30% of the patient population. In yet other embodiments, the effective TNFa inhibitor was previously identified as achieving a PASI90 response in at least about 40% of the patient population. In still yet other embodiments, the effective TNFa inhibitor was previously identified as achieving a PASI90 response in at least about 45% of the patient population.

In some aspects, the present invention provides for the use of a TNFα inhibitor for the manufacture of a medicament for the treatment of mild to moderate psoriatic arthritis (PsA), wherein the medicament is for administration to a subject who has a PASI score <10. In other aspects, the present invention provides for the use of a TNFα inhibitor for the manufacture of a medicament for the treatment of moderate to severe psoriatic arthritis (PsA), wherein the medicament is for administration to a subject who has a PASI score ≥10. In still yet other embodiments, the present invention provides for the use of a TNF inhibitor in the manufacture of a medicament for the treatment of psoriatic arthritis (PsA) and oligoarthritis.

In some aspects, the present invention provides for a method of improving both arthritis and physical functioning of a human subject having PsA and oligoarthritis comprising administering a TNFα inhibitor to the subject. In some aspects, the present invention provides for a method of treating PsA in a subject having a subtherapeutic response to treatment with a TNFα inhibitor comprising administering the TNFα inhibitor to the subject on a weekly dosing regimen, such that PsA is treated. In some embodiments, the TNFα inhibitor is a TNFα antibody, or antigen-binding portion thereof, or a TNFα fusion protein. In other embodiments, the TNFα fusion protein is etanercept.

In some aspects, the present invention provides a method of determining the efficacy of a human TNFa antibody, or antigen-binding portion thereof, for treating psoriatic arthritis in a subject comprising: determining an ACR50 response of a patient population having psoriatic arthritis and who was administered the human TNFa antibody, or antigen-binding portion thereof, wherein an ACR50 response in at least about 42% of the patient population indicates that the human TNFa antibody, or antigen-binding portion thereof, is an effective human TNFa antibody, or antigen-binding portion thereof, for the treatment of psoriatic arthritis in a subject. In some embodiments, the method further comprises administering the effective human TNFa antibody, or antigen-binding portion thereof, to a subject to treat psoriatic arthritis. In some embodiments, an ACR50 response in at least about 49% of the patient population indicates that the human TNFa antibody, or antigen-binding portion thereof, is an effective human TNFa antibody, or antigen-binding portion thereof, for the treatment of psoriatic arthritis in a subject. In other embodiments, an ACR50 response in at least about 52% of the patient population indicates that the human TNFa antibody, or antigen-binding portion thereof, is an effective human TNFa antibody, or antigen-binding portion thereof, for the treatment of psoriatic arthritis in a subject. In some embodiments, an ACR50 response in at least about 58% of the patient population indicates that the human TNFa antibody, or antigen-binding portion thereof, is an effective human TNFa antibody, or antigen-binding portion thereof, for the treatment of psoriatic arthritis in a subject. In other embodiments, an ACR50 response in at least about 60% of the patient population indicates that the human TNFa antibody, or antigen-binding portion thereof, is an effective human TNFa antibody, or antigen-binding portion thereof, for the treatment of psoriatic arthritis in a subject.

In some aspects, the present invention provides a method of treating psoriatic arthritis in a subject comprising administering an effective human TNFa antibody, or antigen-binding portion thereof, to the subject such that psoriatic arthritis is treated, wherein the effective human TNFa antibody, or antigen-binding portion thereof, was previously identified as achieving an ACR50 response in at least about 42% of the patient population. In other aspects, the present invention provides for the use of an effective human TNFa antibody, or antigen-binding portion thereof, in the manufacture of a medicament for the treatment of psoriatic arthritis in a subject, wherein the effective human TNFa antibody, or antigen-binding portion thereof, was previously identified as achieving an ACR50 response in at least about 42% of the patient population who was administered the effective human TNFa antibody, or antigen-binding portion thereof. In some embodiments, the effective human TNFa antibody, or antigen-binding portion thereof, or antigen-binding portion thereof, was previously identified as achieving an ACR50 response in at least about 49% of the patient population. In other embodiments, the effective human TNFa antibody, or antigen-binding portion thereof, was previously identified as achieving an ACR50 response in at least about 52% of the patient population. In yet other embodiments, the effective human TNFa antibody, or antigen-binding portion thereof, was previously identified as achieving an ACR50 response in at least about 58% of the patient population. In some embodiments, the effective human TNFa antibody, or antigen-binding portion thereof, was previously identified as achieving an ACR50 response in at least about 60% of the patient population.

In some aspects, the present invention provides a method of determining the efficacy of a human TNFa antibody, or antigen-binding portion thereof, for treating psoriatic arthritis in a subject comprising: determining an ACR70 response of a patient population having psoriatic arthritis and who was administered the human TNFa antibody, or antigen-binding portion thereof, wherein an ACR70 response in at least about 29% of the patient population indicates that the human TNFa antibody, or antigen-binding portion thereof, is an effective human TNFa antibody, or antigen-binding portion thereof, for the treatment of psoriatic arthritis in a subject. In some embodiments, the method further comprises administering the effective human TNFa antibody, or antigen-binding portion thereof, to a subject to treat psoriatic arthritis. In some embodiments, an ACR70 response in at least about 31% of the patient population indicates that the human TNFa antibody, or antigen-binding portion thereof, is an effective human TNFa antibody, or antigen-binding portion thereof, for the treatment of psoriatic arthritis in a subject. In other embodiments, an ACR70 response in at least about 35% of the patient population indicates that the human TNFa antibody, or antigen-binding portion thereof, is an effective human TNFa antibody, or antigen-binding portion thereof, for the treatment of psoriatic arthritis in a subject. In other embodiments, an ACR70 response in at least about 37% of the patient population indicates that the human TNFa antibody, or antigen-binding portion thereof, is an effective human TNFa antibody, or antigen-binding portion thereof, for the treatment of psoriatic arthritis in a subject. In yet other embodiments, an ACR70 response in at least about 40% of the patient population indicates that the human TNFa antibody, or antigen-binding portion thereof, is an effective human TNFa antibody, or antigen-binding portion thereof, for the treatment of psoriatic arthritis in a subject.

In some aspects, the present invention provides a method of treating psoriatic arthritis in a subject comprising administering an effective human TNFa antibody, or antigen-binding portion thereof, to the subject such that psoriatic arthritis is treated, wherein the effective human TNFa antibody, or antigen-binding portion thereof, was previously identified as achieving an ACR70 response in at least about 29% of the patient population. In other embodiments, the present invention provides for the use of an effective human TNFa antibody, or antigen-binding portion thereof, in the manufacture of a medicament for the treatment of psoriatic arthritis in a subject, wherein the effective human TNFa antibody, or antigen-binding portion thereof, was previously identified as achieving an ACR70 response in at least about 29% of the patient population who was administered the human TNFa antibody, or antigen-binding portion thereof. In some embodiments, the effective human TNF a antibody, or antigen-binding portion thereof, was previously identified as achieving an ACR70 response in at least about 31% of the patient population. In other embodiments, the effective human TNF a antibody, or antigen-binding portion thereof, was previously identified as achieving an ACR70 response in at least about 35% of the patient population. In yet other embodiments, the effective human TNF a antibody, or antigen-binding portion thereof, was previously identified as achieving an ACR70 response in at least about 37% of the patient population. In some embodiments, the effective human TNF a antibody, or antigen-binding portion thereof, was previously identified as achieving an ACR70 response in at least about 40% of the patient population.

In some aspects, the present invention provides a method of determining the efficacy of a human TNFa antibody, or antigen-binding portion thereof, for treating psoriatic arthritis in a subject comprising: determining a PASI75 response of a patient population having psoriatic arthritis and who was administered the human TNFa antibody, or antigen-binding portion thereof, wherein a PASI75 response in at least about 65% of the patient population indicates that the human TNFa antibody, or antigen-binding portion thereof, is an effective human TNFa antibody, or antigen-binding portion thereof, for the treatment of psoriatic arthritis in a subject. In some embodiments, the method further comprises administering the effective human TNFa antibody, or antigen-binding portion thereof, to a subject to treat psoriatic arthritis. In other embodiments, a PASI75 response in at least about 70% of the patient population indicates that the human TNFa antibody, or antigen-binding portion thereof, is an effective human TNFa antibody, or antigen-binding portion thereof, for the treatment of psoriatic arthritis in a subject. In some embodiments, a PASI75 response in at least about 75% of the patient population indicates that the human TNFa antibody, or antigen-binding portion thereof, is an effective human TNFa antibody, or antigen-binding portion thereof, for the treatment of psoriatic arthritis in a subject.

In some aspects, the present invention provides a method of treating psoriatic arthritis in a subject comprising administering an effective human TNFa antibody, or antigen-binding portion thereof, to the subject such that psoriatic arthritis is treated, wherein the effective human TNFa antibody, or antigen-binding portion thereof, was previously identified as achieving a PASI75 response in at least about 65% of the patient population. In some aspects, the present invention provides for the use of an effective human TNFa antibody, or antigen-binding portion thereof, in the manufacture of a medicament for the treatment of psoriatic arthritis in a subject, wherein the effective human TNFa antibody, or antigen-binding portion thereof, was previously identified as achieving a PASI75 response in at least about 65% of the patient population who was administered the effective human TNFa antibody, or antigen-binding portion thereof. In some embodiments, the effective human TNF a antibody, or antigen-binding portion thereof, was previously identified as achieving a PASI75 response in at least about 70% of the patient population. In other embodiments, the effective human TNF a antibody, or antigen-binding portion thereof, was previously identified as achieving a PASI75 response in at least about 75% of the patient population.

In some aspects, the present invention provides for a method of determining the efficacy of a human TNFa antibody, or antigen-binding portion thereof, for treating psoriatic arthritis in a subject comprising: determining a PGA response of "Clear" or "Almost Clear," of a patient population having psoriatic arthritis and who was administered the human TNFa antibody, or antigen-binding portion thereof, wherein a PGA response of "Clear" or "Almost Clear," in at least about 30% of the patient population indicates that the human TNFa antibody, or antigen-binding portion thereof, is an effective human TNFa antibody, or antigen-binding portion thereof, for the treatment of psoriatic arthritis in a subject. In some embodiments, the method further comprises, administering the effective human TNFa antibody, or antigen-binding portion thereof, to a subject to treat psoriatic arthritis. In yet other embodiments, a PGA response of "Clear" or "Almost Clear," in at least about 45% of the patient population indicates that the human TNFa antibody, or antigen-binding portion thereof, is an effective human TNFa antibody, or antigen-binding portion thereof, for the treatment of psoriatic arthritis in a subject. In other embodiments, a PGA response of "Clear" or "Almost Clear," in at least about 60% of the patient population indicates that the human TNFa antibody, or antigen-binding portion thereof, is an effective human TNFa antibody, or antigen-binding portion thereof, for the treatment of psoriatic arthritis in a subject. In still yet other embodiments, a PGA response of "Clear" or "Almost Clear," in at least about 75% of the patient population indicates that the human TNFa antibody, or antigen-binding portion thereof, is an effective human TNFa antibody, or antigen-binding portion thereof, for the treatment of psoriatic arthritis in a subject. In other embodiments, a PGA response of "Clear" or "Almost Clear," in at least about 80% of the patient population indicates that the human TNFa antibody, or antigen-binding portion thereof, is an effective human TNFa antibody, or antigen-binding portion thereof, for the treatment of psoriatic arthritis in a subject.

In some aspects, the present invention provides a method of treating psoriatic arthritis in a subject comprising administering an effective human TNFa antibody, or antigen-binding portion thereof, to the subject such that psoriatic arthritis is treated, wherein the effective human TNFa antibody, or antigen-binding portion thereof, was previously identified as achieving a PGA response of "Clear" or "Almost Clear," in at least about 30% of the patient population. In other aspects, the present invention provides for the use of an effective human TNFa antibody, or antigen-binding portion thereof, in the manufacture of a medicament for the treatment of psoriatic arthritis in a subject, wherein the effective human TNFa antibody, or antigen-binding portion thereof, was previously identified as achieving a PGA response of "Clear" or "Almost Clear," in at least about 30% of the patient population who was administered the effective human TNFα antibody, or antigen-binding portion thereof. In some embodiments, the effective human TNF a antibody, or antigen-binding portion thereof, was previously identified as achieving a PGA response of "Clear" or "Almost Clear," in at least about 45% of the patient population. In other embodiments, the effective human TNF a antibody, or antigen-binding portion thereof, was previously identified as achieving a PGA response of "Clear" or "Almost Clear," in at least about 60% of the patient population. In some embodiments, the effective human TNF a antibody, or antigen-binding portion thereof, was previously identified as achieving a PGA response of "Clear" or "Almost Clear," in at least about 75% of the patient population. In other embodiments, the effective human TNF a antibody, or antigen-binding portion thereof, was previously identified as achieving a PGA response of "Clear" or "Almost Clear," in at least about 80% of the patient population.

In some embodiments, the human TNFα antibody, or antigen-binding portion thereof, is administered to the subject in a biweekly dosing regimen. In other embodiments, the human TNFα antibody, or antigen-binding portion thereof, is administered to the subject in a dose of 40 mg. In yet other embodiments, the human TNFα antibody, or antigen-binding portion thereof, is administered to the subject subcutaneously.

In some embodiments, the human TNFa antibody, or an antigen-binding portion thereof, dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less. In other embodiments, the human TNFa antibody, or an antigen-binding portion thereof, has the following characteristics: a) dissociates from human TNFα with a $K_{off}$ rate constant of $1\times10^{-3}$ s$^{-1}$ or less, as determined by surface plasmon resonance; b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12. In other embodiments, the human TNFa antibody, or an antigen-binding portion thereof, comprises a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and comprises a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In yet other embodiments, the human TNFa antibody, or an antigen-binding portion thereof, comprises a light chain variable region (LCVR) comprising the amino acid sequence of SEQ ID NO: 1 and a heavy chain variable region (HCVR) comprising the amino acid sequence of SEQ ID NO: 2. In still yet other embodiments, the human TNFa antibody, or an antigen-binding portion thereof, is adalimumab.

The invention provides an article of manufacture comprising a packaging material; a TNFα inhibitor; and a label or package insert contained within the packaging material indicating that the standardized mortality rate for the TNFα inhibitor was calculated at about 0.67.

The invention also provides a method of treating a human subject having rheumatoid arthritis (RA) comprising administering a TNFα inhibitor to the subject, wherein the subject has previously failed an anti-TNFα therapy comprising administration of an alternate TNFα antagonist. In one embodiment, the alternate TNFα antagonist is a biologic agent. In one embodiment, the biologic agent comprises etanercept or infliximab. In another embodiment, the alternate TNFα antagonist was discontinued for a reason selected from the group consisting of no response, lost efficacy, and intolerance.

The invention includes a method for monitoring the effectiveness of a TNFα inhibitor for the treatment of rheumatoid arthritis (RA) in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR20 achieved in about 58-85% of the patient population indicates that the TNFα inhibitor is effective at treating RA.

The invention also provides a method for monitoring the effectiveness of a TNFα inhibitor for the treatment of RA in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR50 achieved in about 30-62% of the patient population indicates that the TNFα inhibitor is effective at treating RA.

The invention also provides a method for monitoring the effectiveness of a TNFα inhibitor for the treatment of RA in a human subject comprising administering the TNFα inhibitor to a preselected patient population having RA; and determining the effectiveness of the TNFα inhibitor using a baseline ACR score of the patient population and an ACR score of the patient population following administration of the TNFα inhibitor, wherein an ACR70 achieved in about 12-38% of the patient population indicates that the TNFα inhibitor is effective at treating RA. In one embodiment, preselected patient population has already been administered the TNFα inhibitor.

The invention includes a method for monitoring the effectiveness of a TNFα inhibitor for the treatment of RA in a human subject comprising administering the TNFα inhibitor to a preselected patient population having rheumatoid arthritis; determining the effectiveness of the TNFα inhibitor using a baseline Disease Activity Score (DAS)28 score of the patient population and a DAS28 score of the patient population following administration of the TNFα inhibitor, wherein a mean change in the DAS28 score of between about −1.9 and −2.8 of the patient population indicates that the TNFα inhibitor is effective at treating RA. In one embodiment, the TNFα inhibitor has already been administered to the pre-selected patient population.

The invention includes an article of manufacture comprising a packaging material; a TNFα inhibitor; and a label or package insert contained within the packaging material indicating that patients receiving treatment with the TNFα inhibitor can be safely administered a pneumonococcal or influenza virus vaccine.

The invention also includes an article of manufacture comprising a packaging material; pneumonococcal or influenza virus vaccine; and a label or package insert contained within the packaging material indicating that patients receiving the pneumonococcal or influenza virus vaccine can be safely administered a TNFα inhibitor.

The invention provides a method for treating RA and immunizing against a pneumonococcal or influenza virus antigen in a human subject comprising administering a TNFα inhibitor to the subject; and administering a pneumonococcal or influenza viral vaccine to the subject.

The invention further provides an article of manufacture comprising a packaging material; a TNFα inhibitor; and a label or package insert contained within the packaging material indicating that in studies of the TNFα inhibitor, observed malignancies included melanoma and granulose cell tumor of the ovary.

The invention includes a method of achieving an early clinical response in a Hispanic human subject having RA comprising administering a TNFα inhibitor such that an early clinical response in the Hispanic human subject is achieved. In one embodiment, the Hispanic human subject is Venezuelan. In one embodiment, the early clinical response is determined using an assessment test selected from the group consisting of DAS28, TJC28, SJC28, HAQ, pain on VAS, ESR, and CRP. In another embodiment, the invention includes the early clinical response occurs at about 2 weeks following administration of the TNFα inhibitor.

The invention provides a method of testing the efficacy of a TNFα inhibitor for the rapid improvement of moderate to severe RA in a Hispanic patient population comprising administering the TNFα inhibitor to a preselected Hispanic patient population having moderate to severe RA; determining the efficacy of the TNFα inhibitor using a baseline Health Assessment Questionnaire (HAQ) score of the patient population and an HAQ score of the patient population following administration of the TNFα inhibitor, wherein a decrease in the mean HAQ score of at least about −0.5 indicates that the TNFα inhibitor is efficacious for the rapid improvement of moderate to severe RA in a Hispanic patient population. In one embodiment, the rapid improvement occurs at about 2 weeks following administration of the TNFα inhibitor. In one embodiment, the TNFα inhibitor has already been administered to the pre-selected patient population.

The invention provides an article of manufacture comprising a packaging material; a TNFα inhibitor; and a label or package insert contained within the packaging material indicating that in studies of the TNFα inhibitor for the treatment of juvenile rheumatoid arthritis (JRA) the most common adverse events (AEs) were infections. In one embodiment, the infections include mild upper respiratory infections.

In one embodiment, the TNFα inhibitor is administered weekly. In another embodiment, the TNFα inhibitor is administered every other week.

The invention provides a method of monitoring the effectiveness of a TNFα inhibitor for the treatment of Crohn's disease comprising administering the TNFα inhibitor to a preselected patient population having Crohn's disease; and determining the effectiveness of the TNFα inhibitor using a mean baseline Crohn's Disease Activity Index (CDAI) score of the patient population and a mean CDAI score following administration of the TNFα inhibitor, wherein a Δ100 CDAI in at least about 60% of the patient population indicates that the TNFα inhibitor is effective for the treatment of Crohn's disease.

The invention also includes a method of monitoring the effectiveness of a TNFα inhibitor for the treatment of Crohn's disease comprising administering the TNFα inhibitor to a preselected patient population having Crohn's disease; and determining the effectiveness of the TNFα inhibitor by using a mean baseline Crohn's Disease Activity Index (CDAI) score of the patient population and a mean CDAI score following administration of the TNFα inhibitor, wherein a CDAI<150 achieved in at least about 40% of the patient population indicates that the TNFα inhibitor is effective for the treatment of Crohn's disease. In one embodiment, the patient population comprises patients on concomitant immunosuppressant (IMM) treatment. In another embodiment, the patient population comprises patients not on concomitant IMM treatment. In one embodiment, the TNFα inhibitor has already been administered to the pre-selected patient population.

The invention provides a method of testing the efficacy of a TNFα inhibitor to induce and maintain remission of Crohn's disease comprising administering the TNFα inhibitor to a preselected patient population having Crohn's disease; and determining the efficacy of the TNFα inhibitor by using a mean baseline Inflammatory Bowel Disease Questionnaire (IBDQ) score of the patient population and a mean IBDQ score following administration of the TNFα inhibitor, wherein an IBDQ>170 achieved in at least about 74% of the patient population indicates that the TNFα inhibitor is efficacious for inducing and maintaining remission of Crohn's disease. In one embodiment, the TNFα inhibitor is administered weekly. In another embodiment, the TNFα inhibitor is administered every other week. In one embodiment, the TNFα inhibitor has already been administered to the pre-selected patient population.

The invention further provides a package comprising a TNFα inhibitor and a label, in a position which is visible to prospective purchasers, comprising a printed statement which informs prospective purchasers that the median apparent clearance (CL/F) of the TNFα inhibitor ranges from about 13.2 to about 15.0 mL/hr. In one embodiment of the invention, the package further informs prospective purchasers that concomitant therapy with either immunosuppressant 6 mercaptopurine or azathioprine has slightly lower or no impact on TNFα inhibitor CL/F. In one embodiment, the anti-TNFα antibody, or antigen-binding portion thereof, is a 40 mg dose.

The invention also includes a method of achieving a PASI50 response and improving a Physician's Global Assessment (PGA) score to a score of at least "almost clear" in about 74% of a preselected patient population having psoriatic arthritis (PsA) and a baseline PASI<10, comprising administering a TNFα inhibitor to the patient population such that the PASI50 response and the PGA score of "almost clear" is achieved in about 74% of the patient population.

The invention includes a method of achieving a PASI75 response and improving a Physician's Global Assessment (PGA) score to a score of at least "almost clear" in about 62% of a preselected patient population having PsA and a baseline PASI<10, comprising administering a TNFα inhibitor to the patient population such that the PASI75 response and the PGA score of "almost clear" is achieved in about 74% of the patient population.

The invention also describes a method of achieving a PASI90 response and improving a Physician's Global Assessment (PGA) score to a score of at least "almost clear" in about 38% of a preselected patient population having PsA and a baseline PASI>10, comprising administering a TNFα inhibitor to the patient population such that the PASI90 response is achieved and the PGA score of "almost clear" in about 38% of the patient population is achieved.

In one embodiment of the invention, the PASI response and improved PGA score is achieved in about 24 weeks.

The invention further describes a method of testing the efficacy of a TNFα inhibitor for the treatment of mild to moderate PsA comprising treating a preselected patient population having a PASI score <10 with the TNFα inhibitor; and determining the efficacy of the TNFα inhibitor using a baseline Physician Global Assessment (PGA) score of the patient population following administration of the TNFα inhibitor, wherein a PGA score of "clear" or "almost clear" in at least about 75% of the patient population indicates that the TNFα inhibitor is efficacious for the treatment of mild to moderate PsA.

The invention describes a method of testing the efficacy of a TNFα inhibitor for the treatment of moderate to severe PsA comprising: treating a preselected patient population having a PASI score >10 with the TNFα inhibitor; and determining the efficacy of the TNFα inhibitor using a PGA score of the patient population following administration of the TNFα inhibitor, wherein a PGA of "clear" or "almost clear" in 38% of the patient population indicates that TNFα inhibitor is efficacious for the treatment of moderate to severe PsA. In one embodiment, the TNFα inhibitor has already been administered to the pre-selected patient population.

The invention includes a method of testing the efficacy of a TNFα inhibitor for treating mild to moderate PsA comprising: treating a preselected patient population having mild to moderate PsA with the TNFα inhibitor; and determining the efficacy of the TNFα inhibitor using a baseline PASI score of the patient population and a PASI score of the patient population following administration of the TNFα inhibitor, wherein a PASI50 score in about 77% of the patient population indicates that the TNFα inhibitor is efficacious for the treatment of mild to moderate PsA. In one embodiment, the TNFα inhibitor has already been administered to the pre-selected patient population.

The invention provides a method of testing the efficacy of a TNFα inhibitor for treating mild to moderate PsA comprising treating a preselected patient population having mild to moderate PsA with the TNFα inhibitor; and determining the efficacy of the TNFα inhibitor using a baseline PASI score of the patient population and a PASI score of the patient population following administration of the TNFα inhibitor, wherein a PASI75 score in about 60% of the patient population indicates that the TNFα inhibitor is efficacious for the treatment of mild to moderate PsA. In one embodiment, the TNFα inhibitor has already been administered to the pre-selected patient population.

The invention also includes a method of testing the efficacy of a TNFα inhibitor for treating mild to moderate PsA comprising treating a preselected patient population having mild to moderate PsA with the TNFα inhibitor; and determining the efficacy of the TNFα inhibitor using a baseline PASI score of a the patient population and a PASI score of the patient population following administration of the TNFα inhibitor, wherein a PASI90 score in about 40% of the patient population indicates that the TNFα inhibitor is efficacious for the treatment of mild to moderate PsA.

The invention also includes a method of testing the efficacy of a TNFα inhibitor for treating moderate to severe PsA comprising treating a preselected patient population with the TNFα inhibitor; and determining the efficacy of the TNFα inhibitor using a baseline PASI score of patient population and a PASI score of the patient population following administration of the TNFα inhibitor, wherein a PASI50 score in about 74% of the patient population indicates that the TNFα inhibitor is efficacious for the treatment of moderate to severe PsA.

The invention provides a method of testing the efficacy of a TNFα inhibitor for treating moderate to severe PsA comprising treating a preselected patient population having moderate to severe PsA with the TNFα inhibitor; and determining the efficacy of the TNFα inhibitor using a baseline PASI score of the patient population and a PASI score of the patient population following administration of the TNFα inhibitor, wherein a PASI75 score in about 59% of the patient population indicates that the TNFα inhibitor is efficacious for the treatment of moderate to severe PsA.

The invention also describes a method of testing the efficacy of a TNFα inhibitor for treating moderate to severe PsA comprising treating a preselected patient population having moderate to severe PsA with the TNFα inhibitor; and determining the efficacy of the TNFα inhibitor using a baseline PASI score of the patient population and a PASI score of the patient population following administration of the TNFα inhibitor, wherein a PASI90 score in about 44% of the patient population indicates that the TNFα inhibitor is efficacious for the treatment of moderate to severe PsA. In one embodiment, the TNFα inhibitor has already been administered to the pre-selected patient population.

The invention further provides a method for predicting the efficacy of a TNFα inhibitor for improving the PGA score of a subject having mild to moderate PsA comprising treating the subject with the TNFα inhibitor; determining the post-treatment PASI score of the subject; and determining the change between a predetermined baseline PASI score and the post-treatment PASI score of (b), wherein a PASI50 or a PASI75 response indicates that the TNFα inhibitor is efficacious for improving the PGA score in the subject having mild to moderate PsA. In one embodiment, the subject as a baseline PASI<10.

The invention includes a method for predicting the efficacy of a TNFα inhibitor for improving the PGA score of a subject having moderate to severe PsA comprising treating the subject with the TNFα inhibitor; determining the post-treatment PASI score of the subject; and determining the change between a predetermined baseline PASI score and the post-treatment PASI score of (b), wherein a PASI90 response indicates that the TNFα inhibitor is efficacious or improving the PGA score in the subject having moderate to severe PsA. In one embodiment, the subject as a baseline PASI>10.

The invention further provides a method for reducing both joint inflammation and skin disease in a subject having PsA comprising administering a TNFα inhibitor such that a PASI50 and an ACR20 response is achieved.

In one embodiment, a PASI75 response is achieved. In another embodiment, a PASI90 response is achieved. In another embodiment of the invention, an ACR50 response is achieved. In another embodiment of the invention, an ACR70 response is achieved.

The invention also describes a method for determining the efficacy of a TNFα inhibitor for the treatment of PsA comprising administering a TNFα inhibitor to a preselected patient population having psoriasis affecting about 3% body surface area (BSA) at baseline; and determining the efficacy of the TNFα inhibitor using a baseline ACR score and a baseline PASI score of the patient population and an ACR score and a PASI score of the patient population following administration of the TNFα inhibitor, wherein an ACR20 response achieved in about 54% and a PASI50 response achieved in about 70% of the patient population indicates that TNFα inhibitor is efficacious for the treatment of PsA.

The invention also provides a method for determining the efficacy of a TNFα inhibitor for the treatment of PsA comprising administering a TNFα inhibitor to a preselected patient population having psoriasis affecting about 3% body surface area (BSA) at baseline; and determining the efficacy of the TNFα inhibitor using a baseline ACR score and a baseline PASI score of the patient population and an ACR score and a PASI score of the patient population following administration of the TNFα inhibitor, wherein an ACR70 and a PASI75 response achieved in about 26% of the patient population indicates that TNFα inhibitor is efficacious for the treatment of PsA.

The invention further provides a method for determining the efficacy of a TNFα inhibitor for the treatment of PsA comprising administering a TNFα inhibitor to a preselected patient population having psoriasis affecting about 3% body surface area (BSA) at baseline; and determining the efficacy of the TNFα inhibitor using a baseline ACR score and a baseline PASI score of the patient population and an ACR score and a PASI score of the patient population following administration of the TNFα inhibitor, wherein an ACR70 and a PASI90 response achieved in about 16% of the patient population indicates that TNFα inhibitor is efficacious for the treatment of PsA. In one embodiment, the TNFα inhibitor has already been administered to the pre-selected patient population.

The invention includes a method of improving both arthritis and physical functioning of a human subject having PsA and oligoarthritis comprising administering a TNFα inhibitor to the subject. In one embodiment, the invention further comprises determining a Health Assessment Questionnaire (HAQ) score of the subject following administration of the TNFα inhibitor, wherein the HAQ score decreases by about 0.2 from a pre-determined baseline HAQ score of the subject. In one embodiment, the HAQ score decreases by about 0.3. In another embodiment, the HAQ score decreases by about 0.5. In one embodiment, the subject has a baseline tender joint count (TJC)<5 or a baseline swollen joint count (SJC)<5.

The invention further provides a method for monitoring the effectiveness of a TNFα inhibitor for the treatment of oligoarthritis associated with PsA comprising administering a TNFα inhibitor to a patient population having PsA and oligoarthritis; and determining the effectiveness of the TNFα inhibitor using a baseline HAQ score of the patient population and an HAQ score of the patient population following administration of the TNFα inhibitor, wherein an average decrease in the HAQ score of about 0.2 in the patient population indicates that TNFα inhibitor is effective for the treatment of oligoarthritis in human subjects with PsA. In one embodiment, the subjects in the patient population have a baseline TJC<5 and/or a baseline SJC<5. In another embodiment, the invention further comprises determining the effectiveness of the TNFα inhibitor using a baseline ACR score of the patient population and an ACR score of the patient population following administration of the TNFα inhibitor, wherein an ACR20 response in about 50% of the patient population indicates that TNFα inhibitor is effective for the treatment of oligoarthritis in human subjects with PsA. In one embodiment, the TNFα inhibitor has already been administered to the pre-selected patient population when the effectiveness is determined.

The invention also includes a method of determining the effectiveness of a TNFα inhibitor for treating PsA regardless of the disease duration in a patient comprising administering the TNFα inhibitor to each of two preselected patient populations, wherein the patient populations comprise an early patient population having a baseline PsA disease duration <about 2 years and a late patient population having a baseline PsA disease duration >about 10 years; determining the effectiveness of the TNFα inhibitor by obtaining both an early and a late patient population result using a baseline score from a selected assessment test from both the early and late patient populations, wherein the assessment test is selected from the group consisting of an HAQ score, a DAS28 score, and an ACR score, and a corresponding score from the selected assessment test in the early and late patient populations following administration of the TNFα inhibitor, wherein at least one early patient result selected from the group consisting of
  i) a mean decrease of about 0.3 in the HAQ score between the two early patient populations;
  ii) a mean decrease of about 1.5 in the DAS28 score between the two early patient populations;
  iii) an ACR20 response in about 46% of the early patient population;
  iv) an ACR50 response in about 38% of the early patient population;
  v) an ACR70 response in about 23% of the early patient population; and at least one late patient result selected from the group consisting of
  i) a mean decrease of about 0.4 in the HAQ score between the two late patient populations;
  ii) a mean decrease of about 1.8 in the DAS28 score between the two late patient populations;
  iii) an ACR20 response of about 59% of the late patient population,
  iv) an ACR50 response of about 36% of the late patient population, and
  v) an ACR70 response of about 20% in the late patient population, indicates that the TNFα inhibitor is effective for treating PsA regardless of the disease duration in a patient.

The invention also includes a method of for determining the efficacy of a TNFα inhibitor for achieving complete resolution of general loss of physical functional associated with moderate to severe PsA comprising administering the TNFα inhibitor to a preselected patient population having moderate to severe psoriatic arthritis; and determining the efficacy of the TNFα inhibitor using a baseline Disability Index of the HAQ (HAQ DI) score of the patient population and an HAQ DI score of the patient population following administration of the TNFα inhibitor, wherein an HAQ DI score of 0 in about 30-40% of the patient population indicates that TNFα inhibitor is efficacious for the complete resolution of general loss of physical functional associated with moderate to severe PsA. In one embodiment, the TNFα inhibitor has already been administered to the pre-selected patient population when the efficacy is determined.

The invention provides a method of for determining the efficacy of a TNFα inhibitor for achieving complete resolution of dermatologic-related loss of physical functional associated with moderate to severe psoriatic arthritis comprising administering the TNFα inhibitor to a preselected patient population having moderate to severe psoriatic arthritis and a BSA>3%; and determining the efficacy of the TNFα inhibitor using a baseline DLQI score from the patient population and a DLQI score of the patient population following administration of the TNFα inhibitor, wherein a DLQI score of 0 in about 30-40% of the patient population indicates that TNFα inhibitor is efficacious for the complete resolution of dermatologic-related loss of physical functional associated with moderate to severe PsA.

The invention also provides a method for completely resolving dermatologic-related loss of physical functional in a human subject having moderate to severe PsA comprising administering adalimumab on a biweekly dosing regimen to the subject. In one embodiment, the dermatologic-related loss of physical functional is completely resolved within 12 weeks.

The invention further provides a method of treating a subtherapeutic response in a human subject having PsA comprising administering a TNFα inhibitor weekly to the subject. In one embodiment, the human subject has a baseline diagnosis of >3 swollen joint count and >3 tender joint count. In another embodiment, the subtherapeutic response comprises an improvement of less than 20% in both swollen and tender joint counts between baseline (week 0) and at a determined time period following baseline. In still another embodiment, the determined time period following baseline is about 12 weeks.

The invention describes a method of achieving an ACR20 response in about 41% of a preselected patient population having a subtherapeutic response to treatment for PsA, comprising administering a TNFα inhibitor weekly to the patient population until an ACR20 response is achieved in about 41% of the patient population.

The invention also describes a method of achieving a PASI50 response in about 60% of a preselected patient population having a subtherapeutic response to treatment for PsA, comprising administering a TNFα inhibitor weekly to the patient population until a PASI50 response is achieved in about 60% of the patient population.

The invention further provides a method of achieving a PGA score of at least "almost clear" in about 32% of a preselected patient population having a subtherapeutic response to treatment for PsA, comprising administering a TNFα inhibitor weekly to the patient population until a PGA score of at least "almost clear" is achieved in about 32% of the patient population. In one embodiment, the subtherapeutic response comprises an improvement of less a 20% improvement in both swollen and tender joint counts between baseline (week 0) and a determined time period following baseline. In another embodiment, the determined time period following baseline is about 12 weeks.

The invention includes a method of treating ankylosing spondylitis (AS) in a subject comprising subcutaneously administering to the subject a TNFα inhibitor on a biweekly dosing regimen, wherein the serum trough concentration level of the TNFα inhibitor in the subject is no less than about 6-7 µg/mL. In one embodiment, the TNFα inhibitor is administered in combination with methotrexate.

The invention also provides a method of treating AS in a subject comprising subcutaneously administering to the subject a TNFα inhibitor on a biweekly dosing regimen in combination with methotrexate, wherein the serum trough concentration level of TNFα inhibitor in the subject is no less than about 7-9 µg/mL.

The invention describes a package comprising a TNFα inhibitor and a label, in a position which is visible to prospective purchasers, comprising a printed statement which informs prospective purchasers that TNFα inhibitor mean steady-state trough concentrations of approximately 6-7 µg/mL and 7-9 µg/mL were observed without and with methotrexate, respectively.

The invention describes a method of testing the effectiveness of a TNFα inhibitor for the treatment of AS comprising administering the TNFα inhibitor to a preselected patient population having AS and determining the effectiveness of the TNFα inhibitor using the Assessment in Ankylosing Spondylitis (ASAS) response rate in the patient population, wherein an ASAS20 response rate in about 68% of the patient population indicates the TNFα inhibitor is effective for the treatment of AS.

The invention further includes a method of testing the efficacy of a TNFα inhibitor for the treatment of AS administering the TNFα inhibitor to a preselected patient population having AS; and determining the efficacy of the TNFα inhibitor using the presence of anti-TNFα inhibitor antibodies in the serum of subjects of the patient population in correlation with a baseline ASAS score from the patient population and an ASAS score of the patient population following administration of the TNFα inhibitor, wherein the TNFα inhibitor is effective for treating AS if an ASAS20 response is achieved in about 76% of patients determined as having no anti-TNFα inhibitor antibodies in the serum. In one embodiment, the TNFα inhibitor has already been administered to the pre-selected patient population when the efficacy is determined.

The invention also includes a method of testing the efficacy of a TNFα inhibitor for the treatment of AS administering the TNFα inhibitor to a preselected patient population having AS; and determining the efficacy of the TNFα inhibitor using the presence of anti-TNFα inhibitor antibodies in the serum of subjects of the patient population in correlation with a baseline ASAS score from the patient population and an ASAS score of the patient population following administration of the TNFα inhibitor, wherein the TNFα inhibitor is effective for treating AS is an ASAS20 response is achieved in about 68% of patients determined as having anti-TNFα inhibitor antibodies in their serum. In one embodiment, the presence of anti-TNFα inhibitor antibodies is determining using ELISA methods. In one embodiment, the TNFα inhibitor has already been administered to the pre-selected patient population when the efficacy is determined.

The invention describes a method of testing the efficacy of a TNFα inhibitor for the treatment of AS comprising: administering the TNFα inhibitor to a preselected patient population having AS; and determining the efficacy of the TNFα inhibitor using a baseline Bath Ankylosing Spondylitis Activity Index (BASDAI) score of the patient population and a BASDAI score of the patient population following administration of the TNFα inhibitor, wherein a BASDAI20 in about 80% of the patient population indicates that the TNFα inhibitor is effective for treating AS. In one embodiment, the TNFα inhibitor has already been administered to the pre-selected patient population when the efficacy is determined.

The invention also includes a method of testing the efficacy of a TNFα inhibitor for the treatment of AS comprising: administering the TNFα inhibitor to a preselected patient population having AS; and determining the efficacy of the TNFα inhibitor using a baseline BASDAI score of the patient population and a BASDAI score of the patient population following administration of the TNFα inhibitor, wherein a BASDAI50 in about 67% of the patient population indicates the TNFα inhibitor is effective for treating AS. In one embodiment, the TNFα inhibitor has already been administered to the pre-selected patient population when the efficacy is determined.

The invention describes a method of testing the efficacy of a TNFα inhibitor for the treatment of AS comprising: administering the TNFα inhibitor to a preselected patient population having AS; and determining the efficacy of the TNFα inhibitor using a baseline BASDAI score of the patient population and a BASDAI score of the patient population following administration of the TNFα inhibitor, wherein a BASDAI70 in about 27% of the patient population indicates the TNFα inhibitor is effective for treating AS. In one embodiment, the TNFα inhibitor has already been administered to the pre-selected patient population when the efficacy is determined.

The invention also provides a method of testing the efficacy of a TNFα inhibitor for the treatment of AS comprising: administering the TNFα inhibitor to a preselected patient population having AS; and determining the efficacy of the TNFα inhibitor using a baseline ASAS score of the patient population and an ASAS score of the patient population following administration of the TNFα inhibitor, wherein an ASAS20 in about 73% of the patient population indicates that TNFα inhibitor is effective for treating AS. In one embodiment, the TNFα inhibitor has already been administered to the pre-selected patient population when the efficacy is determined.

The invention describes a method of testing the efficacy of a TNFα inhibitor for the treatment of AS comprising: administering the TNFα inhibitor to a preselected patient population having AS; and determining the efficacy of the TNFα inhibitor using a baseline ASAS score of the patient population and an ASAS score of the patient population following administration of the TNFα inhibitor, wherein an ASAS40 in about 60% of the patient population indicates the TNFα inhibitor is effective for treating AS. In one embodiment, the TNFα inhibitor has already been administered to the pre-selected patient population when the efficacy is determined.

The invention includes method of testing the efficacy of a TNFα inhibitor for the treatment of AS comprising administering the TNFα inhibitor to a preselected patient population having AS; and determining the efficacy of the TNFα inhibitor using a baseline ASAS score of the patient population and an ASAS score of the patient population following administration of the TNFα inhibitor, wherein a ASAS70 in about 40% of the patient population indicates the TNFα inhibitor is effective for treating AS. In one embodiment, the TNFα inhibitor has already been administered to the pre-selected patient population when the efficacy is determined.

The invention also includes a method of predicting long-term efficacy of a TNFα inhibitor for treatment of AS in a human subject comprising administering the TNFα inhibitor to the subject; and predicting the long-term efficacy using a baseline C-reactive protein (CRP) concentration of the subject and the CRP concentration of the subject at about 2 weeks following administration of the TNFα inhibitor, wherein a CRP concentration decrease to a normal range indicates that the TNFα inhibitor will be effective for the long term treatment of AS. In one embodiment, the baseline CRP concentration is about 15 mg/L. In one embodiment, the TNFα inhibitor has already been administered to the pre-selected patient population when the efficacy is determined.

The invention also provides a method for improving the overall well being of a subject having AS comprising administering a TNFα inhibitor to the subject and determining the physical functioning response of the subject, wherein an improvement in the physical functioning response indicates an improvement in the overall well being of the subject. In one embodiment, the physical functioning response is determined using an index selected from the group consisting of an ASAS response, a BASDAI response, or a combination thereof. In another embodiment, the invention further comprises verifying the improvement in the overall well being of the subject using a Health Related Quality of Life (HRQL) score. In one embodiment, the HRQL score is determined using an index selected from the group consisting of a SF-36 mental summary component (SF-36 MCS) score, an AS Quality of Life (ASQoL) score, or a combination thereof.

The invention provides a method for improving the physical functioning response of a subject having AS comprising administering a TNFα inhibitor to the subject and determining the overall well being of the subject, wherein an improvement in the overall well being of the subject indicates an improvement in the overall physical functioning response of the subject. In one embodiment, the overall well being of the subject is determining using an HRQL score. In one embodiment, the HRQL score is determined using an index selected from the group consisting of a SF-36 MCS score, an ASQoL score, or a combination thereof. In one embodiment, the change in the ASQoL score is about 2 or the change in the SF-36 MCS score is >3 from baseline. In one embodiment, the invention further comprises verifying the improvement in the physical functioning response using an index selected from the group consisting of an ASAS response, a BASDAI response, or a combination thereof.

The invention includes a method for determining the efficacy of a TNFα inhibitor for improving the overall well being and physical functioning in a human subject having AS comprising a) administering the TNFα inhibitor to a patient population having AS; and b) determining the efficacy of the TNFα inhibitor using a baseline physical functioning response selected from the group consisting of an ASAS response, a BASDAI response, or a combination thereof, and a baseline overall well being response comprising an HRQL score based on an index selected from the group consisting of a SF-36 MCS score, an ASQoL score, or a combination thereof, of the patient population and a corresponding physical functioning response and overall well being response of the patient population following administration of the TNFα inhibitor, wherein the TNFα inhibitor is effective at improving the overall well being and physical functioning of the patient population if at least one of the following is achieved:

i) the patient population has an ASAS response of at least ASAS70 and has a mean SF-36 MCS score change from baseline of at least about 14;

ii) the patient population has an ASAS response between at least ASAS20 to less than ASAS50 and has a mean ASQoL score change from baseline of at least about −3.1;

iii) the patient population has an ASAS response between at least ASAS50 to less than ASAS70 and a mean ASQoL score change from baseline of at least about −4.0;

iv) the patient population has an ASAS response between at least ASAS20 to less than ASAS50 and a mean ASQoL score change from baseline of at least about −3.1;

v) the patient population has an ASAS response of at least ASAS70 and a mean ASQoL score change from baseline of at least about −7.5;

vi) the patient population has a BASDAI response of at least BASDAI50 to less than BASDAI70 and a mean SF-36 MCS score change from baseline of at least about 4.3;

vii) the patient population has a BASDAI response of at least BASDAI70 and a mean SF-36 MCS score change from baseline of at least about 7.6;

viii) the patient population has a BASDAI response of at least BASDAI50 to less than BASDAI70 and a mean SF-36 MCS score change from baseline of at least about 4.3;

ix) the patient population has a BASDAI response of at least BASDAI50 to less than BASDAI70 and a mean ASQoL score change from baseline of at least about −4.0; and x) the patient population has a BASDAI response of at least BASDAI70 and a mean ASQoL score change from baseline of at least about −6.8.

The invention also provides a method of reducing both spinal and sacroiliac (SI) joint inflammation in a human subject having AS comprising administering a TNFα inhibitor to the subject such the spinal and sacroiliac (SI) joint inflammation is reduced. In one embodiment, the reduction of spinal and SI joint inflammation is determined using magnetic resonance imaging (MRI). In another embodiment, there is at least about a 53% improvement in spine inflammation from a baseline determination to a determination at a time period following baseline. In still another embodiment, there is at least about a 54% improvement in SI joint inflammation from a baseline determination to a determination at a time period following baseline. In one embodiment, the time period following baseline is about 12 weeks.

The invention provides a method of predicting the efficacy of a TNFα inhibitor for the treatment of AS comprising administering the TNFα inhibitor to a human subject having AS; predicting the efficacy of the TNFα inhibitor using a baseline C-reactive protein (CRP) level of the human subject and a CRP level following administration of the TNFα inhibitor, wherein a reduction in the CRP level to normal levels indicates that the TNFα inhibitor is effective at treating AS.

The invention includes a method for monitoring the effectiveness of a TNFα inhibitor for the treatment of pain in a human subject having AS comprising: administering the TNFα inhibitor to the subject; and determining the effectiveness of the TNFα inhibitor using a baseline score from a pain assessment test selected from the group consisting of Total Back Pain (TBP) VAS, Nocturnal Pain (NP) VAS, and the SF-36 Bodily Pain domain and a score from the pain assessment test following administration of the TNFα inhibitor, wherein a change selected from the group consisting of about −19.5 for the TBP assessment test; about −19.2 for the NP assessment test; and about 19.2 for the SF-36 assessment test indicates that the TNFα inhibitor is effective at reducing pain in a subject having AS.

The invention further provides a method for monitoring the effectiveness of a TNFα inhibitor for the treatment of fatigue in a human subject having AS comprising: administering the TNFα inhibitor to the subject; and determining the effectiveness of the TNFα inhibitor using a either a baseline BASDAI fatigue item score or a baseline SF-36 Vitality item score and a BASDAI fatigue item score or a baseline SF-36 Vitality item score following administration of the TNFα inhibitor, wherein either a change of about −1.1 for the BASDAI fatigue item or about 13.1 for the SF-36 vitality item indicates that the TNFα inhibitor is effective at reducing fatigue in a subject having AS.

The invention also provides a method for monitoring the effectiveness of a TNFα inhibitor for treatment of enthesitis in a human subject having AS comprising: administering the TNFα inhibitor to the subject; and determining the effectiveness of the TNFα inhibitor using a baseline BASDAI enthesitis item score and a BASDAI enthesitis item score determined after administration of the TNFα inhibitor, wherein a change of about −1.79 for the BASDAI enthesitis item indicates that the TNFα inhibitor is effective at reducing enthesitis in a subject having AS.

The invention includes a method for determining the efficacy of a TNFα inhibitor for improving the functional limitations of human subjects having moderate to severe chronic plaque psoriasis comprising administering the TNFα inhibitor to a preselected patient population having moderate to severe chronic plaque psoriasis; and determining the efficacy of the TNFα inhibitor using a baseline Dermatology Life Quality Index (DLQI) score from the patient population and a DLQI score from a time period following administration of the TNFα inhibitor, wherein a DLQI score of no or small impact in at least about 83% of the patient population indicates that TNFα inhibitor is efficacious for improving the functional limitations of human subjects having moderate to severe chronic plaque psoriasis. In one embodiment, the TNFα inhibitor has already been administered to the pre-selected patient population when the efficacy is determined.

In one embodiment, the TNFα inhibitor is administered weekly to the patient population. In another embodiment, the TNFα inhibitor is administered biweekly to the patient population. In still another embodiment, the TNFα inhibitor is administered in a multiple variable dose regimen. In one embodiment, the multiple variable dose regimen comprises an induction dose which is at least double the treatment dose. In one embodiment, the induction dose comprises about 80 mg. In one embodiment, the treatment dose comprises about 40 mg.

The invention provides an article of manufacture comprising: a packaging material; a TNFα inhibitor, and a label or package insert contained within the packaging material indicating that a history of systemic or biologic therapy does not adversely affect efficacy of the TNFα inhibitor in patients.

The invention also provides an article of manufacture comprising: a packaging material; a TNFα inhibitor, and a label or package insert contained within the packaging material indicating that administration of the TNFα inhibitor is safe in patients with a history of systemic or biologic therapy. In one embodiment, the patients have moderate to severe psoriasis.

The invention includes a method of treating a subtherapeutic response in a subject having moderate to severe plaque psoriasis comprising administering a TNFα inhibitor to the subject at an increased dosing rate which is about twice as frequent as the original dosing rate. In one embodiment, the increased dosing rate is weekly. In another embodiment, the subtherapeutic response comprises <PASI50 improvement from baseline (week 0) and a determined time period following baseline. In one embodiment, the determined time period following baseline is about 24 weeks.

The invention includes a package comprising a TNFα inhibitor and instructions for administering the TNFα inhibitor to a human subject for the treatment of adults with moderate to severe active ankylosing spondylitis who have had an inadequate response to conventional therapy.

The invention also includes a package comprising a TNFα inhibitor, wherein the package contains, on the label and in a position which is visible to prospective purchasers, a printed statement which informs prospective purchasers that the TNFα inhibitor is indicated for the treatment of adults with moderate to severe active ankylosing spondylitis who have had an inadequate response to conventional therapy.

The invention further provides a package comprising a TNFα inhibitor, wherein the package contains, on the label and in a position which is visible to prospective purchasers, a printed statement which informs prospective purchasers that the recommended dose of the TNFα inhibitor for patients with ankylosing spondylitis is 40 mg TNFα inhibitor administered every other week as a single dose via subcutaneous injection.

The invention also includes a package comprising a TNFα inhibitor, wherein the package contains, on the label and in a position which is visible to prospective purchasers, a printed statement which informs prospective purchasers that available data suggest that the clinical response is usually achieved within 12 weeks of treatment; and continued therapy should be carefully reconsidered in a patient not responding within this time period.

The invention provides a package comprising adalimumab, wherein the package contains, on the label and in a position which is visible to prospective purchasers, a printed statement which informs prospective purchasers that the proportion of patients who discontinued treatment due to adverse events during the double-blind, controlled portion of Studies I-IX was 5.1% for patients taking the adalimumab and 3.2% for control treated patients.

The invention also provides a package comprising a TNFα inhibitor, wherein the package contains, on the label and in a position which is visible to prospective purchasers, a printed statement which informs prospective purchasers that the TNFα inhibitor has been shown to have an uncommon undesirable effect in clinical studies selected from the group consisting of vaginal infection (including fungal), hyperglycaemia, dysphonia, pharyngeal erythema, wheezing, skin reaction, skin exfoliation, spasm, rheumatoid nodule, shoulder pain, and feeling hot.

The invention further provides a package comprising adalimumab, wherein the package contains, on the label and in a position which is visible to prospective purchasers, a printed statement which informs prospective purchasers of at least one of the following notifications: in the nine controlled trials, 17% of patients treated with adalimumab developed injection site reactions (erythema and/or itching, haemorrhage, pain or swelling), compared to 10% of patients receiving placebo or active control; in the nine controlled trials, the rate of infection was 1.52 per patient year in the adalimumab treated patients and 1.40 per patient year in the placebo and active control-treated patients; in the nine controlled trials, 29 malignancies were reported in 2370 adalimumab treated patients with 1779 patient-years of exposure (16.3 per 1000 patient years), and 6 malignancies were reported in 1309 control treated patients observed with 872 patient-years of exposure (6.9 per 1000 patient years); this included 2 lymphomas in the adalimumab treated patients (1.1 per 1000 patient years) and 1 lymphoma in the control treated patients (1.1 per 1000 patient years); and two patients out of 3834 treated with adalimumab in all rheumatoid arthritis, psoriatic arthritis and ankylosing spondylitis studies developed clinical signs suggestive of new-onset lupus-like syndrome.

In one embodiment of the invention, the TNFα inhibitor is selected from the group consisting of an anti-TNFα antibody, or an antigen-binding portion thereof, a TNF fusion protein, or a recombinant TNF binding protein. In one embodiment, the TNF fusion protein is etanercept. In another embodiment of the invention, the anti-TNFα antibody, or antigen-binding portion thereof, is selected from the group consisting of a chimeric antibody, a humanized antibody, and a multivalent antibody.

In one embodiment of the invention, the anti-TNFα antibody, or antigen-binding portion thereof, is a human antibody.

In another embodiment, the anti-TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less.

In one embodiment of the invention, the anti-TNFα antibody is an isolated human antibody, or antigen-binding portion thereof, with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment of the invention, the anti-TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2. In one embodiment, the anti-TNFα antibody, or antigen-binding portion thereof, is adalimumab.

In one embodiment, the anti-TNFα antibody, or antigen-binding portion thereof, is a 40 mg dose.

In another embodiment, the anti-TNFα antibody, or antigen-binding portion thereof, is administered subcutaneously.

In another embodiment of the invention, the anti-TNFα antibody, or antigen-binding portion thereof, is infliximab or golimumab.

The invention provides methods for determining the efficacy of a TNFα inhibitor for a disorder in which TNFα activity is detrimental, including rheumatoid arthritis (RA), juvenile RA, ankylosing spondylitis (AS), and psoriatic arthritis (PsA). Each of the examples described herein describes methods which can be used to determine whether a TNFα inhibitor is effective for treating the given disorder.

The invention describes a method of preventing flare ups associated with juvenile arthritis (JRA) comprising administering adalimumab to a patient having JRA, such that flare ups are prevented. In one embodiment, the flare up is prevented from occurring for at least about 32 weeks. In another embodiment, the flare up is prevented from occurring for at least about 48 weeks.

The invention describes a method for predicting the efficacy of a TNFα inhibitor for the treatment of rheumatoid arthritis in a patient comprising using a mean baseline score selected from the group consisting of a global assessment of the patient's disease activity, pain, function, fatigue, and stiffness, wherein an improvement selected from the group consisting of an improvement of at least about 2.4 in the patient global score, an improvement of at least about 2.8 in the pain score, an improvement of at least about 2.7 in the function score, an improvement of at least about 0.8 in the fatigue score, and an improvement of at least about 1.2 in the stiffness score, at day 1 from baseline indicates that the TNFα inhibitor will be effective for treating RA in the patient.

The invention describes a method for predicting the efficacy of a TNFα inhibitor for the treatment of rheumatoid arthritis in a patient comprising using the combination of C-reactive protein (CRP) levels of the patient and the Patient Activity Score (PAS), wherein an improvement in both the CRP level and the PAS score early in the treatment of the patient with the TNFα inhibitor indicates that the TNFα inhibitor will be effective at treating RA in the patient. In one embodiment, the PAS score is determined using the Health Assessment Questionnaire (HAQ).

The invention describes a method for determining the efficacy of a TNFα inhibitor for the treatment of ankylosing spondylitis (AS) in a patient comprising assessing whether the patient considers his/her current disease state satisfactory (PASS).

The invention describes a method of achieving partial remission of a patient having AS comprising administering to the patient a TNFα inhibitor.

The invention also describes method of increasing work productivity in a patient having AS comprising administering to the patient a TNFα inhibitor such that physical functioning is improved.

The invention describes a method for identifying a patient having psoriatic arthritis (PsA) who is at risk of aggressive joint destruction and who would benefit from treatment with a TNFα inhibitor, comprising determining the CRP level of the patient, wherein a CRP level of at least about 2.0 indicates a risk of aggressive joint destruction and that the patient would benefit from treatment with a TNFα inhibitor.

The invention describes a method for predicting the efficacy of a TNFα inhibitor for improving the quality of life of a patient having rheumatoid arthritis (RA) in a patient comprising comparing the baseline DAS28 score of the patient with a DAS28 score of the patient following treatment with the TNFα inhibitor, wherein an improvement in the DAS28 indicates that the TNFα inhibitor will be effective for improving the quality of life in the patient. In one embodiment, the patient has severe RA.

The invention describes a method of treating late-onset RA comprising administering adalimumab to a patient having late-onset RA. In one embodiment, the patient is over 60 years old.

The invention describes a method for determining the efficacy of a TNFα inhibitor for the treatment of rheumatoid arthritis comprising comparing a pre-determined baseline Simplified Disease Activity Score (SDAI) from a pre-selected patient population having RA to an SDAI score of the patient population following treatment with the TNFα inhibitor, wherein a mean SDAI of no greater than 3.3 in at least about 11% of the patient population indicates that the TNFα inhibitor will be effective for treating RA.

In one embodiment, the TNFα inhibitor is administered weekly to the patient population. In one embodiment, the TNFα inhibitor is administered biweekly to the patient population.

In another embodiment, the TNFα inhibitor is administered in a multiple variable dose regimen. In one embodiment, the TNFα inhibitor is administered in a biweekly dosing regimen.

In one embodiment, the TNFα inhibitor is administered as a monotherapy.

In another embodiment, the TNFα inhibitor is administered with an additional therapeutic agent. In one embodiment, the TNFα inhibitor is administered with methotrexate. In one embodiment, the patient or patient population is administered methotrexate in combination with the TNFα inhibitor.

In one embodiment, the TNFα inhibitor is selected from the group consisting of a TNFα antibody, or an antigen-binding portion thereof, a TNF fusion protein, or a recombinant TNF binding protein.

In one embodiment, the TNF fusion protein is etanercept.

In one embodiment, the TNFα antibody, or antigen-binding portion thereof, is selected from the group consisting of a chimeric antibody, a humanized antibody, and a multivalent antibody. In one embodiment, the TNFα antibody, or antigen-binding portion thereof, is a human antibody.

In one embodiment, the TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In one embodiment, the TNFα antibody is an isolated human antibody, or antigen-binding portion thereof, with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment, the TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2

In one embodiment, the human TNFα antibody, or antigen-binding portion thereof, is adalimumab.

In one embodiment, the TNFα antibody, or antigen-binding portion thereof, is a 40 mg dose.

In one embodiment, the TNFα antibody, or antigen-binding portion thereof, is administered subcutaneously.

In one embodiment, the TNFα antibody, or antigen-binding portion thereof, is infliximab or golimumab.

The invention provides a method of preventing reactivation of latent tuberculosis (LTB) in a patient prior to administration of a TNFα inhibitor to the subject comprising prescreening the patient for TB, wherein the patient is administered isoniazid (INH) if the patient is identified as being high-risk based on the prescreening results. In one embodiment, the prescreening method is selected from the group consisting of a clinical interview, a PPD test, a chest x-ray, or any combination thereof. In a further embodiment, the patient is administered isoniazid (INH) if the patient is identified as being high-risk if the prescreening result is a positive PPD test.

The invention also provides a method of promoting the safety a TNFα inhibitor for the treatment of a disorder in which TNFα activity is detrimental comprising conveying to a recipient or a medical agent that studies have indicated that prescreening a recipient prior to initial administration of the TNFα inhibitor significantly reduces the chance of latent TB reactivation.

The invention includes a method of achieving a PASI 100 and an improvement in the quality of life in a subject having psoriatic arthritis comprising administering a TNFα inhibitor to the subject such that a PAS100 score and DLQI score of 0 or 1 is achieved.

The invention further provides an article of manufacture comprising: a packaging material; an autoinjector pen filled with a TNFα inhibitor; and a label or package insert contained within the packaging material indicating that the bioequivalence of the TNFα inhibitor is similar regardless of whether the injection site is the thigh or abdomen.

In one embodiment of the invention, the TNFα inhibitor is selected from the group consisting of an anti-TNFα antibody, or an antigen-binding portion thereof, a TNF fusion protein, or a recombinant TNF binding protein. In one embodiment, the TNF fusion protein is etanercept. In another embodiment of the invention, the anti-TNFα antibody, or antigen-binding portion thereof, is selected from the group consisting of a chimeric antibody, a humanized antibody, and a multivalent antibody.

In one embodiment of the invention, the anti-TNFα antibody, or antigen-binding portion thereof, is a human antibody.

In another embodiment, the anti-TNFα antibody, or antigen-binding portion thereof, is an isolated human antibody that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an $IC_{50}$ of $1 \times 10^{-7}$ M or less.

In one embodiment of the invention, the anti-TNFα antibody is an isolated human antibody, or antigen-binding portion thereof, with the following characteristics:

a) dissociates from human TNFα with a $K_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In one embodiment of the invention, the anti-TNFα antibody is an isolated human antibody, or an antigen binding portion thereof, with a light chain variable region (LCVR) comprising the amino acid sequence of SEQ ID NO: 1 and a heavy chain variable region (HCVR) comprising the amino acid sequence of SEQ ID NO: 2. In one embodiment, the anti-TNFα antibody, or antigen-binding portion thereof, is adalimumab.

In one embodiment of the invention, the anti-TNFα antibody, or antigen-binding portion thereof, is infliximab or golimumab or adalimumab.

In one embodiment, the anti-TNFα antibody, or antigen-binding portion thereof, is a 40 mg dose.

In another embodiment, the anti-TNFα antibody, or antigen-binding portion thereof, is administered subcutaneously.

In one embodiment, the anti-TNFα antibody, or antigen-binding portion thereof, is administered on a biweekly dosing regimen.

In one embodiment, the anti-TNFα antibody, or antigen-binding portion thereof, is administered using a multiple variable dose regimen.

The invention provides methods for determining the efficacy of a TNFα inhibitor for a disorder in which TNFα activity is detrimental, including rheumatoid arthritis (RA), ankylosing spondylitis (AS), and psoriatic arthritis (PsA). Each of the examples described herein describes methods which can be used to determine whether a TNFα inhibitor is effective for treating the given disorder.

The invention also describes an article of manufacture comprising a packaging material; a TNFα inhibitor; and a label or package insert contained within the packaging material indicating that patients with rheumatoid arthritis (RA) who previously failed therapy with etanercept or infliximab may benefit from treatment of RA with the human TNFα antibody.

The invention includes a method of promoting a human TNFα antibody to a recipient, the method comprising conveying to the recipient that patients with rheumatoid arthritis (RA) who previously failed therapy with etanercept or infliximab may benefit from treatment of RA with the human TNFα antibody.

In one embodiment, the invention provides compositions and methods described herein in combination with an additional therapeutic agent.

DETAILED DESCRIPTION OF THE INVENTION

I. Definitions

Figure 1:
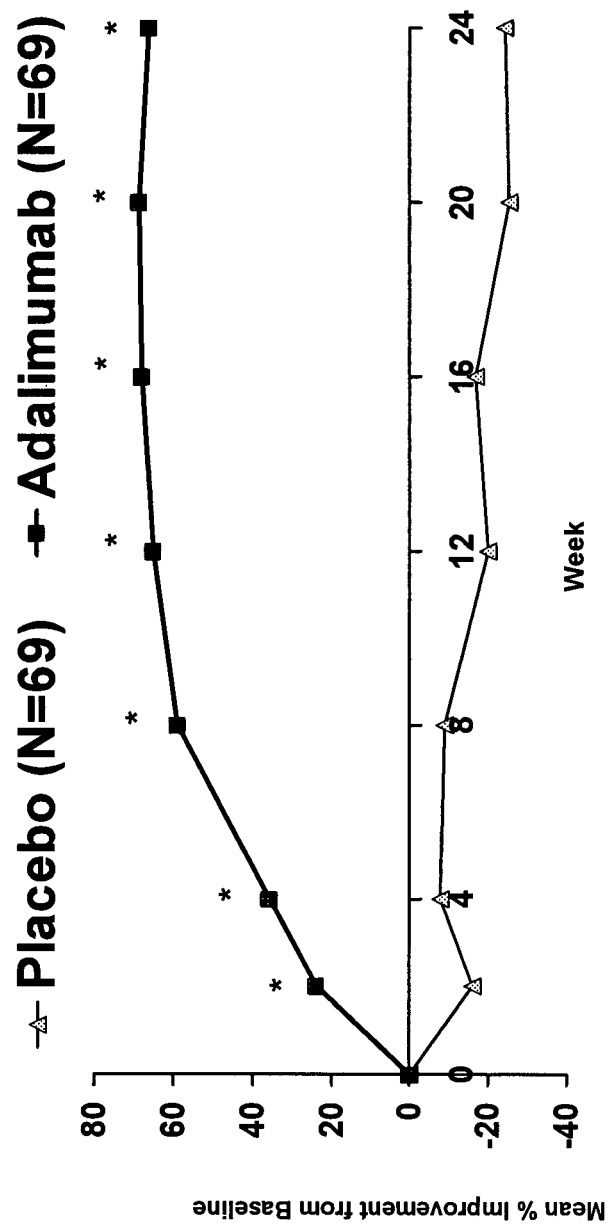
FIG. 1 shows a graphic comparison of the mean percent improvement in PASI over 24 weeks between placebo and adalimumab treated patients.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" includes agents which interfere with TNFα activity. The term also includes each of the anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. In another embodiment, the TNFα inhibitor is a TNF fusion protein, e.g., etanercept (Enbrel®, Amgen; described in WO 91/03553 and WO 09/406,476, incorporated by reference herein). In another embodiment, the TNFα inhibitor is a recombinant TNF binding protein (r-TBP-I) (Serono).

The term "antibody," as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety.

The term "antigen-binding portion" or "antigen-binding fragment" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Binding fragments include Fab, Fab', F(ab')$_2$, Fabc, Fv, single chains, and single-chain antibodies. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

A "conservative amino acid substitution," as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison (1985) Science 229:1202-1207; Oi et al. (1986) BioTechniques 4:214; U.S. Pat. No. 5,225, 539; Jones et al. (1986) Nature 321:552-525; Verhoeyan et al. (1988) Science 239:1534; and Beidler et al. (1988) J. Immunol. 141:4053-4060, Queen et al., Proc. Natl. Acad. Sci. USA 86:10029-10033 (1989), U.S. Pat. No. 5,530,101, U.S. Pat. No. 5,585,089, U.S. Pat. No. 5,693,761, U.S. Pat. No. 5,693,762, Selick et al., WO 90/07861, and Winter, U.S. Pat. No. 5,225,539.

An "isolated antibody," as used herein, is intended to refer to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

A "neutralizing antibody," as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) Ann. Biol. Clin. 51:19; Jönsson et al.

(1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "dose," as used herein, refers to an amount of TNFα inhibitor which is administered to a subject.

The term "dosing", as used herein, refers to the administration of a substance (e.g., an anti-TNFα antibody) to achieve a therapeutic objective (e.g., treatment of psoriatic arthritis).

A "dosing regimen" describes a treatment schedule for a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

The terms "biweekly dosing regimen", "biweekly dosing", and "biweekly administration", as used herein, refer to the time course of administering a substance (e.g., an anti-TNFα antibody) to a subject to achieve a therapeutic objective, e.g., throughout the course of treatment. The biweekly dosing regimen is not intended to include a weekly dosing regimen. Preferably, the substance is administered every 9-19 days, more preferably, every 11-17 days, even more preferably, every 13-15 days, and most preferably, every 14 days. In one embodiment, the biweekly dosing regimen is initiated in a subject at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in US 20030235585, incorporated by reference herein.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present invention, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

The term "combination therapy", as used herein, refers to the administration of two or more therapeutic substances, e.g., an anti-TNFα antibody and another drug. The other drug(s) may be administered concomitant with, prior to, or following the administration of an anti-TNFα antibody.

The term "treatment," as used within the context of the present invention, is meant to include therapeutic treatment, as well as prophylactic or suppressive measures, for the treatment of psoriatic arthritis. For example, in one embodiment, the term "treatment" or "treating" refers to reducing signs and symptoms of active arthritis. In one embodiment, the term "treatment" or "treating" refers to inhibiting the progression of structural damage in patients with psoriatic arthritis. In one embodiment, the term "treatment" or "treating" refers to improving physical function in patients with psoriatic arthritis.

The term treatment may, for example, include administration of a TNFα inhibitor prior to or following the onset of psoriatic arthritis thereby preventing or removing signs of the disease or disorder. As another example, administration of a TNFα inhibitor after clinical manifestation of psoriatic arthritis to combat the symptoms and/or complications and disorders associated with psoriatic arthritis comprises "treatment" of the disease. Further, administration of the agent after onset and after clinical symptoms and/or complications have developed where administration affects clinical parameters of the disease or disorder and perhaps amelioration of the disease, comprises "treatment" of psoriatic arthritis.

Those "in need of treatment" include mammals, such as humans, already having psoriatic arthritis, including those in which the disease or disorder is to be prevented.

Various aspects of the invention are described in further detail herein.

The invention provides improved uses and compositions for treating psoriatic arthritis with a TNFα inhibitor, e.g., a human TNFα antibody, or an antigen-binding portion thereof. Compositions and articles of manufacture, including kits, relating to the methods and uses for treating psoriatic arthritis are also contemplated as part of the invention.

II. TNF Inhibitors

A TNFα inhibitor which is used in the methods and compositions of the invention includes any agent which interferes with TNFα activity. In a preferred embodiment, the TNFα inhibitor can neutralize TNFα activity, particularly detrimental TNFα activity which is associated with psoriatic arthritis, and related complications and symptoms.

In one embodiment, the TNFα inhibitor used in the invention is an TNFα antibody (also referred to herein as a TNFα antibody), or an antigen-binding fragment thereof, including chimeric, humanized, and human antibodies. Examples of TNFα antibodies which may be used in the invention include, but not limited to, infliximab (Remicade®, Johnson and Johnson; described in U.S. Pat. No.

5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502) and adalimumab (HUMIRA® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein.

Other examples of TNFα inhibitors which may be used in the methods and compositions of the invention include etanercept (Enbrel, described in WO 91/03553 and WO 09/406,476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

In one embodiment, the invention features uses and composition for treating or determining the efficacy of a TNFα inhibitor for the treatment of psoriatic arthritis, wherein the TNFα antibody is an isolated human antibody, or antigen-binding portion thereof, that binds to human TNFα with high affinity and a low off rate, and also has a high neutralizing capacity. Preferably, the human antibodies used in the invention are recombinant, neutralizing human anti-hTNFα. antibodies. The most preferred recombinant, neutralizing antibody of the invention is referred to herein as D2E7, also referred to as HUMIRA® or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein. The methods of the invention may also be performed using chimeric and humanized murine anti-hTNFα antibodies which have undergone clinical testing for treatment of rheumatoid arthritis (see e.g., Elliott, M. J., et al. (1994) Lancet 344: 1125-1127; Elliot, M. J., et al. (1994) Lancet 344:1105-1110; Rankin, E. C., et al. (1995) Br. J. Rheumatol. 34:334-342).

In one embodiment, the method of the invention includes determining the efficacy of D2E7 antibodies and antibody portions, D2E7-related antibodies and antibody portions, or other human antibodies and antibody portions with equivalent properties to D2E7, such as high affinity binding to hTNFα with low dissociation kinetics and high neutralizing capacity, for the treatment of psoriatic arthritis. In one embodiment, the invention provides treatment with an isolated human antibody, or an antigen-binding portion thereof, that dissociates from human TNFα with a $K_d$ of $1×10^{-8}$ M or less and a $K_{off}$ rate constant of $1×10^{-3}$ s$^{-1}$ or less, both determined by surface plasmon resonance, and neutralizes human TNFα cytotoxicity in a standard in vitro L929 assay with an IC$_{50}$ of $1×10^{-7}$ M or less. More preferably, the isolated human antibody, or antigen-binding portion thereof, dissociates from human TNFα with a $K_{off}$ of $5×10^{-4}$ s$^{-1}$ or less, or even more preferably, with a $K_{off}$ of $1×10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1×10^{-8}$ M or less, even more preferably with an IC$_{50}$ of $1×10^{-9}$ M or less and still more preferably with an IC$_{50}$ of $1×10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to treating psoriatic arthritis by administering human antibodies that have slow dissociation kinetics for association with hTNFα. and that have light and heavy chain CDR3 domains that structurally are identical to or related to those of D2E7. Position 9 of the D2E7 VL CDR3 can be occupied by Ala or Thr without substantially affecting the $K_{off}$. Accordingly, a consensus motif for the D2E7 VL CDR3 comprises the amino acid sequence: Q-R-Y-N-R-A-P-Y-(T/A) (SEQ ID NO: 3). Additionally, position 12 of the D2E7 VH CDR3 can be occupied by Tyr or Asn, without substantially affecting the $K_{off}$. Accordingly, a consensus motif for the D2E7 VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the D2E7 heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the K.sub.off. Still further, the skilled artisan will appreciate that, given the amenability of the D2E7 VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the D2E7 VL and/or VH CDR3 domains. More preferably, no more than one to three conservative amino acid substitutions are made within the D2E7 VL and/or VH CDR3 domains. Additionally, conservative amino acid substitutions should not be made at amino acid positions critical for binding to hTNFα. Positions 2 and 5 of the D2E7 VL CDR3 and positions 1 and 7 of the D2E7 VH CDR3 appear to be critical for interaction with hTNFα and thus, conservative amino acid substitutions preferably are not made at these positions (although an alanine substitution at position 5 of the D2E7 VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1×10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of 5×10$^{-4}$ s$^{-1}$ or less. Even more preferably, the antibody, or antigen-binding portion thereof, dissociates from human TNFα with a $K_{off}$ of 1×10$^{-4}$ s$^{-1}$ or less.

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). Even more preferably, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL preferably are from the $V_\kappa$I human germline family, more preferably from the A20 human germline Vk gene and most preferably from the D2E7 VL framework sequences shown in FIGS. 1A and 1B of U.S. Pat. No. 6,090,382. The framework regions for VH preferably are from the $V_H$3 human germline family, more preferably from the DP-31 human germline VH gene and most preferably from the D2E7 VH framework sequences shown in FIGS. 2A and 2B of U.S. Pat. No. 6,090,382.

Accordingly, in another embodiment, the antibody or antigen-binding portion thereof preferably contains a light chain variable region (LCVR) comprising the amino acid sequence of SEQ ID NO: 1 (i.e., the D2E7 VL) and a heavy chain variable region (HCVR) comprising the amino acid sequence of SEQ ID NO: 2 (i.e., the D2E7 VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portions thereof, containing D2E7-related VL and VH CDR3 domains. For example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the methods and compositions of the invention may be modified for improved treatment of psoriatic arthritis. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: Focus on Growth Factors 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat psoriatic arthritis by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield, S. M. and S. L. Morrison (1991) *J. Exp. Med.* 173:1483-1491; and Lund, J. et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion used in the methods of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss et al.

To express adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) *Sequences of proteins of Immunological Interest, Fifth Edition*, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of D2E7, or a D2E7-related antibody, a member of the $V_H3$ family of human germline VH genes is amplified by standard PCR. Most preferably, the DP-31 VH germline sequence is amplified. To obtain a DNA fragment encoding the light chain variable region of D2E7, or a D2E7-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the D2E7 or D2E7-related amino acid sequences disclosed herein. The amino acid sequences encoded by the germline VH and VL DNA sequences are first compared to the D2E7 or D2E7-related VH and VL amino acid sequences to identify amino acid residues in the D2E7 or D2E7-related sequence that differ from germline. Then, the appropriate nucleotides of the germline DNA sequences are mutated such that the mutated germline sequence encodes the D2E7 or D2E7-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding D2E7 or D2E7-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of proteins of immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of proteins of immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the D2E7 or D2E7-related light or heavy chain sequences, the expression vector may already carry antibody constant region sequences. For example, one approach to converting the D2E7 or D2E7-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNFα antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

Recombinant human antibodies of the invention in addition to D2E7 or an antigen binding portion thereof, or D2E7-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-65; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al., *Nature* (1990) 348:552-554; and Griffiths et al., (1993) *EMBO J.* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human neutralizing antibodies with high affinity and a low off rate constant for hTNFα are described in U.S. Pat. Nos. 6,090,382, 6,258,562, and 6,509,015, each of which is incorporated by reference herein.

Antibodies, antibody-portions, and other TNFα inhibitors for use in the methods of the invention, can be incorporated into pharmaceutical compositions suitable for administration to a subject. Typically, the pharmaceutical composition comprises an antibody, antibody portion, or other TNFα inhibitor, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody or other TNFα inhibitor is administered by intravenous infusion or injection. In another preferred embodiment, the antibody or other TNFα inhibitor is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, the invention includes pharmaceutical compositions comprising an effective TNFα. inhibitor and a pharmaceutically acceptable carrier, wherein the effective TNFα. inhibitor may be used to treat psoriatic arthritis.

In one embodiment, the antibody or antibody portion for use in the methods of the invention is incorporated into a pharmaceutical formulation as described in PCT/IB03/04502 and U.S. Appln. No. 20040033228, incorporated by reference herein. This formulation includes a concentration 50 mg/ml of the antibody D2E7 (adalimumab), wherein one pre-filled syringe contains 40 mg of antibody for subcutaneous injection.

The antibodies, antibody-portions, and other TNFα inhibitors of the present invention can be administered by a variety of methods known in the art, although for many therapeutic applications, the preferred route/mode of administration is parenteral, e.g., subcutaneous injection. In another embodiment, administration is via intravenous injection or infusion.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, Robinson, ed., Dekker, Inc., New York, 1978.

In one embodiment, the TNFα antibodies and inhibitors used in the invention are delivered to a subject subcutaneously. In one embodiment, the subject administers the TNFα inhibitor, including, but not limited to, TNFα antibody, or antigen-binding portion thereof, to himself/herself.

The TNFα antibodies and inhibitors used in the invention may also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Appln. No. 20040033228, incorporated by reference herein, are used to treat rheumatoid arthritis using the treatment methods of the invention.

In certain embodiments, an antibody, antibody portion, or other TNFα inhibitor of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion for use in the methods of the invention is coformulated with and/or coadministered with one or more additional therapeutic agents, including a psoriatic arthritis inhibitor or antagonist. For example, an anti-hTNFα. antibody or antibody portion of the invention may be coformulated and/or coadministered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Additional description regarding methods and uses of the invention comprising administration of a TNFα inhibitor are described in Part III of this specification.

The invention also pertains to packaged pharmaceutical compositions or kits for administering the anti-TNF antibodies of the invention for the treatment of psoriatic arthritis. In one embodiment of the invention, the kit comprises a TNFα inhibitor, such as an antibody and instructions for administration of the TNFα inhibitor for treatment of psoriatic arthritis. The instructions may describe how, e.g., subcutaneously, and when, e.g., at week 0, week 2, week 4, etc., the different doses of TNFα inhibitor shall be administered to a subject for treatment.

Another aspect of the invention pertains to kits containing a pharmaceutical composition comprising a TNFα inhibitor, such as an antibody, and a pharmaceutically acceptable carrier and one or more pharmaceutical compositions each comprising an additional therapeutic agent useful for treating psoriatic arthritis, and a pharmaceutically acceptable carrier. Alternatively, the kit comprises a single pharmaceutical composition comprising an anti-TNFα antibody, one or more drugs useful for treating psoriatic arthritis, and a pharmaceutically acceptable carrier. The instructions may describe how, e.g., subcutaneously, and when, e.g., at week 0, week 2, week 4, etc., the different doses of TNFα inhibitor and/or the additional therapeutic agent shall be administered to a subject for treatment.

The kit may contain instructions for dosing of the pharmaceutical compositions for the treatment of psoriatic arthritis. Additional description regarding articles of manufacture of the invention are described in subsection III.

The package or kit alternatively can contain the TNFα inhibitor and it can be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

III. Uses and Compositions for Treating Psoriatic Arthritis

Tumor necrosis factor has been implicated in the pathophysiology of psoriatic arthritis (Partsch et al. (1998) *Ann Rheum Dis.* 57:691; Ritchlin et al. (1998) *J Rheumatol.* 25:1544). As referred to herein, psoriatic arthritis (PsA) or psoriasis associated with the skin, refers to chronic inflammatory arthritis which is associated with psoriasis. Psoriasis is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. The TNFα antibody, or antigen-binding fragment thereof, of the invention can be used to treat PsA.

Treatment of psoriatic arthritis may be determined according to standard clinical definitions. For example, primary efficacy for signs and symptoms can be measured via American College of Rheumatology preliminary criteria for improvement (ACR). ACR criteria measures improvement in tender or swollen joint counts and improvement in three of the following five parameters: acute phase reactant (such as sedimentation rate); patient assessment; physician assessment; pain scale; and disability/functional questionnaire. ACR criteria is indicated as ACR 20 (a 20 percent improvement in tender or swollen joint counts as well as 20 percent improvement in three of the other five criteria), ACR 50 (a 50 percent improvement in tender or swollen joint counts as well as 50 percent improvement in three of the other five criteria), and ACR 70 (a 70 percent improvement in tender or swollen joint counts as well as 70 percent improvement in three of the other five criteria).

An additional primary endpoint includes evaluation of radiologic changes over 6 to 12 months to assess changes in structural damage. Multiple other evaluations are performed during treatment including Psoriatic Arthritis Response Criteria (PsARC), quality of life measurements, and skin evaluations to determine efficacy on psoriasis lesions (psoriasis area severity index (PASI) and target lesion evaluations).

In one embodiment, the invention provides a method for treating psoriatic arthritis in a subject comprising administering a human TNFα antibody, or an antigen-binding portion thereof, to the subject, such that the psoriatic arthritis is treated. In one embodiment, the invention describes a use of a human TNFα antibody, or antigen-binding portion thereof, in the manufacture of a medicament for treating psoriatic arthritis in a subject. The medicament may be for administration to the subject on a maintenance dose regimen. In one embodiment, efficacy of treatment of psoriatic arthritis is determined by achievement of an ACR20, ACR50 or ACR70 response, or a PASI50, PASI75, or PASI90 response in the subject.

The TNFα antibody, or an antigen-binding portion thereof, may be administered to the subject on a biweekly dosing regimen. In one embodiment, biweekly dosing includes a dosing regimen wherein doses of a TNFα inhibitor are administered to a subject every other week beginning at week 0. In one embodiment, biweekly dosing includes a dosing regimen where doses of a TNFα inhibitor are administered to a subject every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc.

In one embodiment, treatment of psoriatic arthritis is achieved by administering a human TNFα antibody, or an antigen-binding portion thereof, to a subject having psoriatic arthritis, wherein the human TNFα antibody, or an antigen-binding portion thereof, is administered on a biweekly dosing regimen. In one embodiment, the human TNFα antibody, or an antigen-binding portion thereof, is administered in a dose of about 40 mg. In one embodiment, the human TNFα antibody, or an antigen-binding portion thereof, is adalimumab.

Methods of treatment described herein may include administration of a TNFα inhibitor to a subject to achieve a therapeutic goal, e.g., achievement of an ACR20, ACR50, or ACR70 response, or a PASI50, PASI75, or PASI90 response. Also included in the scope of the invention are uses of a TNFα inhibitor in the manufacture of a medicament to achieve a therapeutic goal, e.g., achievement of an ACR20, ACR50, or ACR70 response, or a PASI50, PASI75, or PASI90 response. Thus, where methods are described herein, it is also intended to be part of this invention that the use of the TNFα inhibitor in the manufacture of a medicament for the purpose of the method is also considered within the scope of the invention. Likewise, where a use of a TNFα inhibitor in the manufacture of a medicament for the purpose of achieving a therapeutic goal is described, methods of treatment resulting in the therapeutic goal are also intended to be part of the invention.

In one embodiment, treatment of psoriatic arthritis is achieved by administering a TNFα inhibitor to a subject in accordance with a biweekly dosing regimen. Biweekly dosing regimens can be used to treat disorders in which TNFα activity is detrimental, and are further described in U.S. application Ser. No. 10/163,657 (US 20030235585), incorporated by reference herein.

In one embodiment, the invention provides a method of treating psoriatic arthritis in a subject comprising administering a human TNFα antibody, or antigen-binding portion thereof, e.g., adalimumab, to the subject at week 0 on a biweekly dosing regimen. In one embodiment, the human TNFα antibody, or antigen-binding portion thereof, is administered subcutaneously. In one embodiment, psoriatic arthritis is treated by administering a human TNFα antibody, or antigen-binding portion thereof, on biweekly dosing regimen for at least about 12, 24, 36 or 48 weeks.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Dosage regimens described herein may be adjusted to provide the optimum desired response, e.g., maintaining remission of psoriatic arthritis, in consideration of the teachings herein. It is to be noted that dosage values may vary with the type and severity of psoriatic arthritis. It is to be further understood that for any particular subject, specific dosage regimens may be adjusted over time according to the teachings of the specification and the individual need and the professional judgment of the person administering or supervising the administration of the compositions, and that dosage amounts and ranges set forth herein are exemplary only and are not intended to limit the scope or practice of the claimed invention.

Examples of other methods and uses of TNFα inhibitors for the treatment of psoriatic arthritis are also described in: U.S. provisional patent application No. 60/812,312 (BBI-248-1), filed on Jun. 8, 2006; U.S. provisional patent application No. 60/832,370 (BBI-254-1), filed on Jul. 20, 2006; and U.S. provisional patent application No. 60/851,830 (BBI-260-1), filed on Oct. 12, 2006; each of which is incorporated herein.

Subpopulations

The invention provides uses and methods for treating certain subpopulations of psoriatic arthritis patients with a TNFα inhibitor.

The invention provides a method of treating oligoarticular arthritis in a subject comprising administering to the subject a TNFα inhibitor, such that oligoarticular arthritis is treated. Subjects having oligoarticular arthritis may be administered a TNFα inhibitor such that oligoarticular arthritis is treated and advancement of the disease is prevented. The invention also provides use of a TNFα inhibitor in the manufacture of a medicament for the treatment of oligoarticular arthritis in a subject who has oligoarticular arthritis.

The invention also provides a method for treating early and established psoriatic arthritis in a subject, comprising administering to the subject a TNFα inhibitor, such that early and established psoriatic arthritis are treated. Subjects having early psoriatic arthritis may be administered a TNFα inhibitor such that the psoriatic arthritis is treated and advancement of the disease is prevented. Subjects having established psoriatic arthritis may be administered a TNFα inhibitor such that the psoriatic arthritis is treated and advancement of the disease is prevented. The invention also provides use of a TNFα inhibitor in the manufacture of a medicament for the treatment of early and established psoriatic arthritis in a subject who has either early or established psoriatic arthritis.

The invention also provides a method for treating a subpopulation of psoriatic arthritis patients who have failed disease modifying anti-rheumatic drug (DMARDs) therapy, e.g., methotrexate, for the treatment of psoriatic arthritis. Traditional interventions for moderate to severe PsA have included nonsteroidal anti-inflammatory drugs (NSAIDs) and nonbiologic disease-modifying antirheumatic drugs (DMARDs). A meta-analysis of published, well-controlled studies found that, of the traditional DMARDs, only high-dosage, parenteral methotrexate (MTX) had demonstrated efficacy for both skin and articular manifestations of PsA. (Jones et al, Cochrane Database Syst Rev 2000; (3): CD000212. 2000). It has not yet been established whether MTX has efficacy against joint destruction in PsA. In certain instances, some patients who are administered a DMARD for the treatment of psoriatic arthritis have subtherapeutic responses to such treatment. In one embodiment, the invention provides use of a TNFα inhibitor in the manufacture of a medicament for treatment of psoriatic arthritis in a subject who has had a subtherapeutic response to a DMARD.

In one embodiment, the invention provides an article of manufacture comprising adalimumab and a package insert, wherein the package insert indicates that adalimumab may be used to treat psoriatic arthritis in patients who have had an inadequate response to conventional DMARD therapy.

Articles of Manufacture

The invention also provides a packaged pharmaceutical composition wherein the TNFα inhibitor, e.g., TNFα antibody, is packaged within a kit or an article of manufacture. The kit or article of manufacture of the invention contains materials useful for the treatment, prevention and/or diagnosis of psoriatic arthritis. The kit or article of manufacture comprises a container and a label or package insert or printed material on or associated with the container which provides information regarding use of the TNFα inhibitor, e.g., a TNFα antibody, for the treatment of psoriatic arthritis.

A kit or an article of manufacture refers to a packaged product comprising components with which to administer a TNFα inhibitor for treatment of psoriatic arthritis. The kit preferably comprises a box or container that holds the components of the kit. The box or container is affixed with a label or a Food and Drug Administration approved label, including a protocol for administering the TNFα inhibitor. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody adalimumab (or D2E7), as described in PCT/IB03/04502 and U.S. application Ser. No. 10/222,140, incorporated by reference herein.

The term "package insert" is used to refer to instructions customarily included in commercial packages of therapeutic products, that contain information about the indications, usage, dosage, administration, contraindications and/or warnings concerning the use of such therapeutic products.

In one embodiment, the article of manufacture of the invention comprises (a) a first container with a composition contained therein, wherein the composition comprises a TNFα antibody; and (b) a package insert indicating that the TNFα antibody may be used for reducing signs and symptoms of psoriatic arthritis. In a preferred embodiment, the label or package insert indicates that the TNFα inhibitor, e.g., a TNFα antibody, is used for treatment of psoriatic arthritis.

Suitable containers for the TNFα inhibitor, e.g., a TNFα antibody, include, for example, bottles, vials, syringes, pens, etc. The containers may be formed from a variety of materials such as glass or plastic. The container holds a composition which is by itself or when combined with another composition effective for treating, preventing and/or diagnosing the condition and may have a sterile access port.

In one embodiment, the article of manufacture comprises a TNFα inhibitor, e.g., a TNFα antibody, and a label which indicates to a subject who will be administering the TNFα inhibitor about using the TNFα inhibitor for the treatment of psoriatic arthritis. The label may be anywhere within or on the article of manufacture. In one embodiment, the article of manufacture comprises a container, such as a box, which comprises the TNFα inhibitor and a package insert or label providing information pertaining to use of the TNFα inhibitor for the treatment of psoriatic arthritis. In another embodiment, the information is printed on a label which is on the outside of the article of manufacture, in a position which is visible to prospective purchasers.

In one embodiment, the package insert of the invention informs a reader, including a subject, e.g., a purchaser, who will be administering the TNFα inhibitor for treatment, that the TNFα inhibitor, e.g., a TNFα antibody such as adalimumab, is an indicated treatment of psoriatic arthritis, including of moderately to severely active disease in adult patients.

In one embodiment, the package insert describes certain patient populations who may respond favorably to the TNFα inhibitor within the article of manufacture. For example, the package insert may indicate that the TNFα antibody, e.g., adalimumab, may be used to treat psoriatic arthritis in patients who have had an inadequate response to conventional therapy.

In another embodiment, the label of the invention indicates that adalimumab is indicated for treatment of early to established psoriatic arthritis in adult patients who have had an inadequate response to conventional therapy. In another embodiment, the label of the invention indicates that adalimumab is indicated for treatment of oligoarticular arthritis in patients with psoriatic arthritis.

In one embodiment, the package insert of the invention describes certain therapeutic benefits of the TNFα antibody, e.g., adalimumab, including specific symptoms of psoriatic arthritis which may be reduced by using the TNFα antibody, e.g., adalimumab. It should be noted that the package insert may also contain information pertaining to other disorders which are treatable using the TNFα antibody, e.g., adalimumab. Information described herein which is provided in a package insert and pertains to other disorders, i.e., diseases other than psoriatic arthritis, is also included within the scope of the invention. The package insert of the invention may indicate that extra TNFα in your body can attack normal healthy body tissues and cause inflammation especially in the tissues in your bones, cartilage, joints and digestive tract. The package insert of the invention may also indicate that adalimumab helps reduce the signs and symptoms of immune diseases, including rheumatoid and psoriatic arthritis (pain and swollen joints), ankylosing spondylitis (morning stiffness and back pain), and Crohn's disease (abdominal pain and diarrhea).

In another embodiment, the package insert of the invention describes the dose and administration of adalimumab, for the treatment of psoriatic arthritis. The label may indicate that the initiation of therapy includes a biweekly 40 mg subcutaneous dose. The label may also indicate that the maintenance dosing for the treatment of psoriatic arthritis with adalimumab is 40 mg every other week. In another embodiment, the package insert of the invention indicates that adalimumab is administered by subcutaneous injection.

In another embodiment, the label of the invention indicates that the recommended TNFα inhibitor, e.g., a TNFα antibody such as adalimumab, dose regimen for adult patients with psoriatic arthritis is 40 mg at week 0, followed by 40 mg every other week.

The package insert of the invention may also provide information to subjects who will be receiving adalimumab regarding combination uses for both safety and efficacy purposes. The package insert of the invention may contain warnings and precautions regarding the use of the TNFα inhibitor, e.g., a TNFα antibody such as adalimumab.

The label of the invention may contain information regarding the use of the TNFα inhibitor, e.g., a TNFα antibody such as adalimumab, in clinical studies for psoriatic arthritis. In one embodiment, the label of the invention describes the studies described herein as the Examples, either as a whole or in portion.

The label of the invention may contain information regarding the pharmacodynamics of the TNFα inhibitor, e.g., a TNFα antibody such as adalimumab. the label of the invention may contain information regarding the pharmacokinetics of the TNFα inhibitor, e.g., a TNFα antibody such as adalimumab.

In one embodiment of the invention, the kit comprises a TNFα inhibitor, such as an antibody, an second pharmaceutical composition comprising an additional therapeutic agent, and instructions for administration of both agents for the treatment of psoriatic arthritis. The instructions may describe how, e.g., subcutaneously, and when, e.g., at week 0, week 2, and biweekly thereafter, doses of TNFα antibody and/or the additional therapeutic agent shall be administered to a subject for treatment.

Another aspect of the invention pertains to kits containing a pharmaceutical composition comprising an anti-TNFα antibody and a pharmaceutically acceptable carrier and one or more additional pharmaceutical compositions each comprising a drug useful for treating a TNFα related disorder and a pharmaceutically acceptable carrier. Alternatively, the kit comprises a single pharmaceutical composition comprising an anti-TNFα antibody, one or more drugs useful for treating a TNFα related disorder and a pharmaceutically acceptable carrier. The kits further contain instructions for dosing of the pharmaceutical compositions for the treatment of a TNFα related disorder.

The package or kit alternatively may contain the TNFα inhibitor and it may be promoted for use, either within the package or through accompanying information, for the uses or treatment of the disorders described herein. The packaged pharmaceuticals or kits further can include a second agent (as described herein) packaged with or copromoted with instructions for using the second agent with a first agent (as described herein).

Additional Therapeutic Agents

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Binding proteins described herein may be used in combination with additional therapeutic agents such as a Disease Modifying Anti-Rheumatic Drug (DMARD) or a Nonsteroidal Antiinflammatory Drug (NSAID) or a steroid or any combination thereof. Preferred examples of a DMARD are hydroxychloroquine, leflunomide, methotrexate, parenteral gold, oral gold and sulfasalazine. Preferred examples of non-steroidal anti-inflammatory drug(s) also referred to as NSAIDS include drugs like ibuprofen. Other preferred combinations are corticosteroids including prednisolone; the well known side effects of steroid use can be reduced or even eliminated by tapering the steroid dose required when treating patients in combination with the antibodies of this invention. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists such as soluble p55 or p75 TNF receptors, derivatives, thereof, (p75TNFR1gG (Enbrel™) or p55TNFR1gG (Lenercept), chimeric, humanized or human TNF antibodies, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor, see WO 02/12502), and adalimumab (Humira® Abbott Laboratories, a human anti-TNF mAb, described in U.S. Pat. No. 6,090,382 as D2E7). Additional TNF antibodies which can be used in the invention are described in U.S. Pat. Nos. 6,593,458; 6,498, 237; 6,451,983; and 6,448,380, each of which is incorporated by reference herein. Other combinations including TNFα converting enzyme (TACE) inhibitors; IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with TNFα function; especially preferred are IL-18 antagonists including IL-18 antibodies or soluble IL-18 receptors, or IL-18 binding proteins. It has been shown that TNFα and IL-18 have overlapping but distinct functions and a combination of antagonists to both may be most effective.

Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

Non-limiting examples of therapeutic agents for Psoriatic Arthritis with which an antibody, or antibody portion, of the invention can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab.

IV. Efficacy of TNFα Inhibitor

The invention also provides methods for determining whether a TNFα inhibitor is effective at treating psoriatic arthritis in a subject. Such methods may be used to determine the efficacy of a TNFα inhibitor, including those which are unknown or unconfirmed to have such efficacy. Using the methods described herein, effective TNFα inhibitors may be determined or confirmed, and, subsequently, used in the method of treating psoriatic arthritis.

In one embodiment, the invention provides a method for determining the efficacy of a TNFα inhibitor, including a human TNFα antibody, for treatment of psoriatic arthritis in a subject, using the American College of Rheumatology (ACR) preliminary criteria for improvement in rheumatoid arthritis. ACR criteria measures improvement in tender or swollen joint counts and improvement in three of the following five parameters: acute phase reactant (such as sedimentation rate); patient assessment; physician assessment; pain scale; and disability/functional questionnaire. ACR criteria is indicated as ACR 20 (a 20 percent improvement in tender or swollen joint counts as well as 20 percent improvement in three of the other five criteria), ACR 50 (a 50 percent improvement in tender or swollen joint counts as well as 50 percent improvement in three of the other five criteria), and ACR 70 (a 70 percent improvement in tender or swollen joint counts as well as 70 percent improvement in three of the other five criteria) (see Felson D T, et al. Arthritis Rheum 1995; 38:727-35).

The efficacy of a TNFα inhibitor for treatment of psoriatic arthritis in a patient population who has psoriatic arthritis, may be evaluated by determining the percentage of the patient population in whom an ACR20, ACR50 or ACR 70 response has been achieved following administration of the TNFα inhibitor.

In one aspect, the invention provides a method of determining the efficacy of a TNFα inhibitor for treating psoriatic arthritis in a subject comprising determining a an ACR20 response of a patient population having psoriatic arthritis and who was administered the TNFα inhibitor, wherein a an ACR20 response in at least about 59% of the patient population indicates that the TNFα inhibitor is an effective TNFα inhibitor for the treatment of psoriatic arthritis in a subject. In one embodiment, the method further comprises administering the effective TNFα inhibitor to a subject to treat psoriatic arthritis. The invention provides a method of treatment of psoriatic arthritis in a subject comprising administering an effective amount of a TNFα inhibitor to the subject such that the subject is treated, wherein the effective amount of the TNFα inhibitor was previously identified as achieving an ACR20 response in at least about 59% of a patient population having psoriatic arthritis.

In one embodiment, an ACR20 response in at least about 61% of the patient population indicates that the TNFa inhibitor is an effective TNFa inhibitor for the treatment of psoriatic arthritis in a subject. In one embodiment, an ACR20 response in at least about 65% of the patient population indicates that the TNFa inhibitor is an effective TNFa inhibitor for the treatment of psoriatic arthritis in a subject. In one embodiment, an ACR20 response in at least about 69% of the patient population indicates that the TNFa inhibitor is an effective TNFa inhibitor for the treatment of psoriatic arthritis in a subject. In one embodiment, an ACR20 response in at least about 72% of the patient population indicates that the TNFa inhibitor is an effective TNFa inhibitor for the treatment of psoriatic arthritis in a subject. In one embodiment, an ACR20 response in at least about 75% of the patient population indicates that the TNFa inhibitor is an effective TNFa inhibitor for the treatment of psoriatic arthritis in a subject. Numbers intermediate to the above recited percentages, e.g., 60. 61, 63, 65, 66, 70, 72%, as well as all other numbers recited herein, are also intended to be part of this invention. Ranges of values using a combination of any of the above recited values as upper and/or lower limits are intended to be included in the scope of the invention. For example, in one embodiment, an ACR20 response in at least about 59% to at least about 75% of the patient population indicates that the TNFa inhibitor is an effective TNFa inhibitor for the treatment of psoriatic arthritis in a subject.

In some aspects, the invention provides a method of determining the efficacy of a human TNFa antibody for treating psoriatic arthritis in a subject comprising determining an ACR50 response of a patient population having psoriatic arthritis and who was administered the human TNFa antibody, wherein an ACR50 response in at least about 42% of the patient population indicates that the human TNFa antibody is an effective human TNFa antibody for the treatment of psoriatic arthritis in a subject. In one embodiment, the method further comprises administering the effective TNFa inhibitor to a subject to treat psoriatic arthritis. The invention provides a method of treatment of psoriatic arthritis in a subject comprising administering an effective amount of a TNFa inhibitor to the subject such that the subject is treated, wherein the effective amount of the TNFa inhibitor was previously identified as achieving an ACR50 response in at least about 42% of a patient population having psoriatic arthritis.

In one embodiment, an ACR50 response in at least about 49% of the patient population indicates that the human TNFa antibody is an effective human TNFa antibody for the treatment of psoriatic arthritis in a subject. In one embodiment, an ACR50 response in at least about 52% of the patient population indicates that the human TNFa antibody is an effective human TNFa antibody for the treatment of psoriatic arthritis in a subject. In one embodiment, an ACR50 response in at least about 58% of the patient population indicates that the human TNFa antibody is an effective human TNFa antibody for the treatment of psoriatic arthritis in a subject. In one embodiment, an ACR50 response in at least about 60% of the patient population indicates that the human TNFa antibody is an effective human TNFa antibody for the treatment of psoriatic arthritis in a subject. Numbers intermediate to the above recited percentages, e.g., 43, 46, 49, 52, 58%, as well as all other numbers recited herein, are also intended to be part of this invention. Ranges of values using a combination of any of the above recited values as upper and/or lower limits are intended to be included in the scope of the invention. For example, in one embodiment, an ACR50 response in at least about 42% to at least about 60% of the patient population indicates that the human TNFa antibody is an effective human TNFa antibody for the treatment of psoriatic arthritis in a subject.

In some aspects, the invention provides a method of determining the efficacy of a human TNFa antibody for treating psoriatic arthritis in a subject comprising determining an ACR70 response of a patient population having psoriatic arthritis and who was administered the human TNFa antibody, wherein an ACR70 response in at least about 29% of the patient population indicates that the human TNFa antibody is an effective human TNFa antibody for the treatment of psoriatic arthritis in a subject. In one embodiment, the method further comprises administering the effective TNFa inhibitor to a subject to treat psoriatic arthritis. The invention provides a method of treatment of psoriatic arthritis in a subject comprising administering an effective amount of a TNFa inhibitor to the subject such that the subject is treated, wherein the effective amount of the TNFa inhibitor was previously identified as achieving an ACR70 response in at least about 29% of a patient population having psoriatic arthritis.

In one embodiment, an ACR70 response in at least about 31% of the patient population indicates that the human TNFa antibody is an effective human TNFa antibody for the treatment of psoriatic arthritis in a subject. In one embodiment, an ACR70 response in at least about 35% of the patient population indicates that the human TNFa antibody is an effective human TNFa antibody for the treatment of psoriatic arthritis in a subject. In one embodiment, an ACR70 response in at least about 37% of the patient population indicates that the human TNFa antibody is an effective human TNFa antibody for the treatment of psoriatic arthritis in a subject. In one embodiment, an ACR70 response in at least about 40% of the patient population indicates that the human TNFa antibody is an effective human TNFa antibody for the treatment of psoriatic arthritis in a subject. Numbers intermediate to the above recited percentages, e.g., 30, 31, 32, 37%, as well as all other numbers recited herein, are also intended to be part of this invention. Ranges of values using a combination of any of the above recited values as upper and/or lower limits are intended to be included in the scope of the invention. For example, in one embodiment, an ACR70 response in at least about 29% to at least about 40% of the patient population indicates that the human TNFa antibody is an effective human TNFa antibody for the treatment of psoriatic arthritis in a subject.

The invention provides a method for determining the efficacy of a TNFα inhibitor, including a human TNFα antibody, for treatment of psoriatic arthritis in a subject, using the Psoriasis Area and Severity Index (PASI). The PASI is used by dermatologists to assess psoriasis disease intensity. This index is based on the quantitative assessment of three typical signs of psoriatic lesions: erythema, infiltration, and desquamation, combined with the skin surface area involvement (see Fredriksson T, et al. Dermatologica 1978; 157: 238-41). PASI is indicated as PASI50 (a 50 percent improvement in PASI from baseline), PASI75 (a 75 percent improvement in PASI from baseline), PASI90 (a 90 percent improvement in PASI from baseline), and PASI100 (a 100 percent improvement in PASI from baseline).

The efficacy of a TNFα inhibitor for treatment of psoriatic arthritis in a patient population who has psoriatic arthritis, may be evaluated by determining the percentage of the patient population in whom a PASI50, PASI75, PASI90, or PASI100 response has been achieved following administration of the TNFα inhibitor.

In some aspects, the invention provides a method of determining the efficacy of a TNFa inhibitor for treating psoriatic arthritis in a subject comprising determining a PASI50 response of a patient population having psoriatic arthritis and who was administered the TNFa inhibitor, wherein a PASI50 response in at least about 55% of the patient population indicates that the TNFa inhibitor is an effective TNFa inhibitor for the treatment of psoriatic arthritis in a subject. In one embodiment, the method further comprises administering the effective TNFα inhibitor to a subject to treat psoriatic arthritis. In some aspects, the present invention provides a method of treating psoriatic arthritis in a subject comprising administering an effective TNFa inhibitor to the subject such that psoriatic arthritis is treated, wherein the effective TNFa inhibitor was previously identified as achieving a PASI50 response in at least about 55% of the patient population.

In one embodiment, a PASI50 response in at least about 60% of the patient population indicates that the TNFa inhibitor is an effective TNFa inhibitor for the treatment of psoriatic arthritis in a subject. In one embodiment, a PASI50 response in at least about 65% of the patient population indicates that the TNFa inhibitor is an effective TNFa inhibitor for the treatment of psoriatic arthritis in a subject. In one embodiment, a PASI50 response in at least about 70% of the patient population indicates that the TNFa inhibitor is an effective TNFa inhibitor for the treatment of psoriatic arthritis in a subject. In one embodiment, a PASI50 response in at least about 75% of the patient population indicates that the TNFa inhibitor is an effective TNFa inhibitor for the treatment of psoriatic arthritis in a subject. In one embodiment, a PASI50 response in at least about 80% of the patient population indicates that the TNFa inhibitor is an effective TNFa inhibitor for the treatment of psoriatic arthritis in a subject. Numbers intermediate to the above recited percentages, e.g., 69, 71%, as well as all other numbers recited herein, are also intended to be part of this invention. Ranges of values using a combination of any of the above recited values as upper and/or lower limits are intended to be included in the scope of the invention. For example, in one embodiment, a PASI50 response in at least about 55% to at least about 80% of the patient population indicates that the TNFa inhibitor is an effective TNFa inhibitor for the treatment of psoriatic arthritis in a subject.

In some aspects, the invention provides a method of determining the efficacy of a human TNFa antibody for treating psoriatic arthritis in a subject comprising determining a PASI75 response of a patient population having psoriatic arthritis and who was administered the human TNFa antibody, wherein a PASI75 response in at least about 65% of the patient population indicates that the human TNFa antibody is an effective human TNFa antibody for the treatment of psoriatic arthritis in a subject. IN one embodiment, the method further comprises administering the effective human TNFa antibody to a subject to treat psoriatic arthritis. In some aspects, a method of treating psoriatic arthritis in a subject comprising administering an effective human TNFa antibody to the subject such that psoriatic arthritis is treated, wherein the effective human TNFa antibody was previously identified as achieving a PASI75 response in at least about 65% of the patient population.

In one embodiment, a PASI75 response in at least about 70% of the patient population indicates that the human TNFa antibody is an effective human TNFa antibody for the treatment of psoriatic arthritis in a subject. In one embodiment, a PASI75 response in at least about 75% of the patient population indicates that the human TNFa antibody is an effective human TNFa antibody for the treatment of psoriatic arthritis in a subject. Numbers intermediate to the above recited percentages, e.g., 69, 71%, as well as all other numbers recited herein, are also intended to be part of this invention. Ranges of values using a combination of any of the above recited values as upper and/or lower limits are intended to be included in the scope of the invention. For example, in one embodiment, a PASI75 response in at least about 65% to at least about 75% of the patient population indicates that the human TNFa antibody is an effective human TNFa antibody for the treatment of psoriatic arthritis in a subject.

In some aspects, the invention provides a method of determining the efficacy of a TNFa inhibitor for treating psoriatic arthritis in a subject comprising determining a PASI90 response of a patient population having psoriatic arthritis and who was administered the TNFa inhibitor, wherein a PASI90 response in at least about 43% of the patient population indicates that the TNFa inhibitor is an effective TNFa inhibitor for the treatment of psoriatic arthritis in a subject. In one embodiment, the invention further comprises administering the effective TNFa inhibitor to a subject to treat psoriatic arthritis. In some aspects, the invention provides a method of treating psoriatic arthritis in a subject comprising administering an effective TNFa inhibitor to the subject such that psoriatic arthritis is treated, wherein the effective TNFa inhibitor was previously identified as achieving a PASI90 response in at least about 43% of the patient population.

In one embodiment, a PASI90 response in at least about 50% of the patient population indicates that the TNFa inhibitor is an effective TNFa inhibitor for the treatment of psoriatic arthritis in a subject. In one embodiment, a PASI90 response in at least about 55% of the patient population indicates that the TNFa inhibitor is an effective TNFa inhibitor for the treatment of psoriatic arthritis in a subject. In one embodiment, a PASI90 response in at least about 60% of the patient population indicates that the TNFa inhibitor is an effective TNFa inhibitor for the treatment of psoriatic arthritis in a subject. In one embodiment, a PASI90 response in at least about 65% of the patient population indicates that the TNFa inhibitor is an effective TNFa inhibitor for the treatment of psoriatic arthritis in a subject. In one embodiment, a PASI90 response in at least about 70% of the patient population indicates that the TNFa inhibitor is an effective TNFa inhibitor for the treatment of psoriatic arthritis in a subject. In one embodiment, a PASI90 response in at least about 75% of the patient population indicates that the TNFa inhibitor is an effective TNFa inhibitor for the treatment of psoriatic arthritis in a subject. Numbers intermediate to the above recited percentages, e.g., 71%, as well as all other numbers recited herein, are also intended to be part of this invention. Ranges of values using a combination of any of the above recited values as upper and/or lower limits are intended to be included in the scope of the invention. For example, in one embodiment, a PASI90 response in at least about 43% to at least about 75% of the patient population indicates that the TNFa inhibitor is an effective TNFa inhibitor for the treatment of psoriatic arthritis in a subject In some aspects, the invention provides a method of determining the efficacy of a TNFa inhibitor for treating psoriatic arthritis in a subject comprising determining a PASI100 response of a patient population having psoriatic arthritis and who was administered the TNFa inhibitor, wherein a PASI100 response in at least about 10% of the patient population indicates that the TNFa inhibitor is an effective TNFa inhibitor for the treatment of psoriatic arthritis in a subject. In one embodiment, the invention further comprises administering the effective TNFa inhibitor to a subject to treat psoriatic arthritis. In some aspects, the invention provides a method of treating psoriatic arthritis in a subject comprising administering an effective TNFa inhibitor to the subject such that psoriatic arthritis is treated, wherein the effective TNFa inhibitor was previously identified as achieving a PASI100 response in at least about 10% of the patient population.

In one embodiment, a PASI100 response in at least about 20% of the patient population indicates that the TNFa inhibitor is an effective TNFa inhibitor for the treatment of psoriatic arthritis in a subject. In one embodiment, a PASI100 response in at least about 30% of the patient population indicates that the TNFa inhibitor is an effective TNFa inhibitor for the treatment of psoriatic arthritis in a subject. In one embodiment, a PASI100 response in at least about 40% of the patient population indicates that the TNFa inhibitor is an effective TNFa inhibitor for the treatment of psoriatic arthritis in a subject. In one embodiment, a PASI100 response in at least about 45% of the patient population indicates that the TNFa inhibitor is an effective TNFa inhibitor for the treatment of psoriatic arthritis in a subject. Numbers intermediate to the above recited percentages, e.g., 32, 43%, as well as all other numbers recited herein, are also intended to be part of this invention. Ranges of values using a combination of any of the above recited values as upper and/or lower limits are intended to be included in the scope of the invention. For example, in one embodiment a PASI100 response in at least about 10% to at least about 45% of the patient population indicates that the TNFa inhibitor is an effective TNFa inhibitor for the treatment of psoriatic arthritis in a subject The invention provides a method for determining the efficacy of a TNFα inhibitor, including α human TNFa antibody, for treatment of psoriatic arthritis in a subject, using the Physician's Global Assessment scale (PGA). PGA is used to assess psoriasis activity and follow clinical response to treatment. It is a score that summarizes the overall quality (erythema, scaling and thickness) and extent of plaques relative to the baseline assessment. A patient's response is rated as worse, poor (0-24%), fair (25-49%), good (50-74%), excellent (75-99%), or cleared (100%) (see van der Kerkhof P. Br J Dermatol 1997; 137:661-662).

The efficacy of a TNFα inhibitor for treatment of psoriatic arthritis in a patient population who has psoriatic arthritis, can be evaluated by determining the percentage of the patient population in whom a PGA of "Clear" or "Almost Clear" has been achieved following administration of the TNFα inhibitor, including a human TNFa antibody.

In some aspects, the invention provides a method of determining the efficacy of a human TNFa antibody for treating psoriatic arthritis in a subject comprising determining a PGA response of "Clear" or "Almost Clear," of a patient population having psoriatic arthritis and who was administered the human TNFa antibody, wherein a PGA response of "Clear" or "Almost Clear," in at least about 30% of the patient population indicates that the human TNFa antibody is an effective human TNFa antibody for the treatment of psoriatic arthritis in a subject. In one embodiment, the invention further comprises administering the effective human TNFa antibody to a subject to treat psoriatic arthritis. In some aspects, the invention provides a method of treating psoriatic arthritis in a subject comprising administering an effective human TNFa antibody to the subject such that psoriatic arthritis is treated, wherein the effective human TNFa antibody was previously identified as achieving a PGA response of "Clear" or "Almost Clear," in at least about 30% of the patient population.

In one embodiment, a PGA response of "Clear" or "Almost Clear," in at least about 45% of the patient population indicates that the human TNFa antibody is an effective human TNFa antibody for the treatment of psoriatic arthritis in a subject. In one embodiment, a PGA response of "Clear" or "Almost Clear," in at least about 60% of the patient population indicates that the human TNFa antibody is an effective human TNFa antibody for the treatment of psoriatic arthritis in a subject. In one embodiment, a PGA response of "Clear" or "Almost Clear," in at least about 75% of the patient population indicates that the human TNFa antibody is an effective human TNFa antibody for the treatment of psoriatic arthritis in a subject. In one embodiment, a PGA response of "Clear" or "Almost Clear," in at least about 80% of the patient population indicates that the human TNFa antibody is an effective human TNFa antibody for the treatment of psoriatic arthritis in a subject. Numbers intermediate to the above recited percentages, e.g., 32, 38, 76%, as well as all other numbers recited herein, are also intended to be part of this invention. Ranges of values using a combination of any of the above recited values as upper and/or lower limits are intended to be included in the scope of the invention. For example, in one embodiment a PGA response of "Clear" or "Almost Clear," in at least about 30% to at least about 80% of the patient population indicates that the human TNFa antibody is an effective human TNFa antibody for the treatment of psoriatic arthritis in a subject.

Additional measures can be used to evaluate the efficacy of a TNFα inhibitor for treatment of psoriatic arthritis, or improvement in the quality of life (QOL) and physical function in a patient population who has psoriatic arthritis, following administration of the TNFa inhibitor, including a human TNFa antibody, or antigen binding fragment thereof. Examples of QOL measures include the Short-Form 36 (SF-36),[78] a broad measure of physical and mental domains which has been used and validated in many diseases, and the Dermatology Life Quality Index (DLQI). For example, in one embodiment, a Health Assessment Questionaire (HAQ) is used to evaluate the efficacy of a TNF α inhibitor for treatment of psoriatic arthritis in a patient population who has psoriatic arthritis. The HAQ is a standardized disability questionnaire that was initially developed for use in rheumatoid arthritis. The HAQ-DI assesses the difficulty a patient has accomplishing tasks in eight functional areas (dressing, arising, eating, walking, hygiene, reaching, gripping and other activities of daily living). A high HAQ score has been shown to be a strong predictor of morbidity and mortality in RA, and low HAQ scores are predictive of better outcomes (see Fries J F, et al. Arthritis Rheum 1980; 23:137-45).

A number of measures of fatigue have been developed as well. Fatigue is an important domain to PsA patients; even in patients without evident clinical psoriasis, fatigue is often overlooked by assessors, yet is capable of significant improvement with newer therapies. In one embodiment, the Functional Assessment of Chronic Illness Therapy (FACIT) can be used to evaluate the efficacy of a TNFa inhibitor for the treatment of psoriatic arthritis in a patient population who has psoriatic arthritis.

It should be noted that the Examples provided herein represent different methods of determining the efficacy of a TNFα inhibitor, such as a human TNFα antibody, or antigen-binding portion thereof. As such, data and results described in the Examples section which shows efficacy of a TNFα inhibitor, e.g., treatment of psoriatic arthritis, are included in the methods of determining efficacy of the invention.

Time points for determining efficacy will be understood by those of skill in the art to depend on the type of efficacy being determined, e.g., treatment of early psoriatic arthritis, treatment of established psoriatic arthritis. In one embodiment, measurements in scores, e.g., ACR20/50/70 response, or PASI50/75/90 response, may be measured against a subject's baseline score. Generally, a baseline refers to a measurement or score of a patient before treatment, i.e. week 0. Other time points may also be included as a starting point in determining efficacy, however.

Patient populations described in the methods of the invention are generally selected based on common characteristics, such as, but not limited to, subjects diagnosed with psoriatic arthritis. Such a patient population would be appropriate for determining the efficacy of the TNFα inhibitor for treating psoriatic arthritis in the given patient population. In one embodiment, the patient population is an adult population, e.g., older than 17 years of age or older than 18 years of age.

In one embodiment, the methods of the invention for determining whether a TNFα inhibitor is an effective TNFα inhibitor, include determining changes, improvements, measurements, etc., in psoriatic arthritis using appropriate indices known in the art, e.g., ACR, PASI, PGA, HAQ, DLQI. from a patient population who has already been administered the TNFα inhibitor. Such a patient population may be pre-selected according to common characteristics, e.g., psoriatic arthritis, loss of response to DMARDs, and may have already been given the TNFα inhibitor. Administration of the TNFα inhibitor may or may not be performed by the same person of ordinary skill who is determining the efficacy of the TNFα inhibitor in accordance with the teachings of the specification.

In one embodiment, the methods of the invention comprise administering the TNFα inhibitor to the subjects of a patient population and determining the efficacy of the TNFα inhibitor by determining changes, improvements, measurements, etc., using psoriatic arthritis indices known in the art, in the patient population in comparison to the Examples set forth below. For example, in one embodiment the invention includes a method for determining the efficacy of a TNFα inhibitor for the treatment of psoriatic arthritis comprising administering the TNFα inhibitor to a preselected patient population having psoriatic arthritis; and determining the effectiveness of the TNFα inhibitor by using a mean baseline ACR score of the patient population and a mean ACR20 score following administration of the TNFα inhibitor, wherein a ACR20 achieved in at least about 59% of the patient population indicates that the TNFα inhibitor is effective for the treatment of psoriatic arthritis.

Methods of the invention relating to determining efficacy, i.e., determining whether a TNFα inhibitor is an effective TNFα inhibitor, may also be applied to specific patient populations within the overall patient population who together have specific, common characteristics, i.e., a subpopulation. For example, the patient population may comprise patients on who previously failed DMARD therapy. In another example, the patient population may comprise patients who did not previously fail DMARD therapy.

In addition, while the above methods are described in terms of patient populations, methods of efficacy described herein may also be applied to individual subjects. For example, a method for determining efficacy may comprise determining whether a subject who has psoriatic arthritis, and who is on a dosage regimen comprising a human TNFα antibody, is able to maintain an ACR20 response.

The Examples and discoveries described herein are representative of a TNFα inhibitor, i.e., adalimumab, which is effective for treating psoriatic arthritis. As such, the studies and results described in the Examples section herein may be used as a guideline for determining the efficacy of a TNFα inhibitor, i.e., whether a TNFα inhibitor is an effective TNFα inhibitor for the treatment of psoriatic arthritis. In one embodiment, methods of determining efficacy described herein may be used to determine whether a TNFα inhibitor is bioequivalent to another TNFα inhibitor.

In one embodiment, the article of manufacture of the invention comprises instructions regarding how to determine the efficacy of the TNF inhibitor for the treatment of psoriatic arthritis.

The present invention is further illustrated by the following examples which should not be construed as limiting in any way. Examples 1 to 12 refer to Study G. The baseline demographic and clinical characteristics for patients participating in Study G are provided in Table 1.

TABLE 1

Baseline Demographics and Disease Characteristics

| Characteristic | Placebo Every Other Week (EOW) N = 162 | Adalimumab 40 mg Every Other Week (EOW) N = 151 |
|---|---|---|
| Age (years) | 49.2 ± 11.1 | 48.6 ± 12.5 |
| % Male | 54.9 | 56.3 |
| % Caucasian | 93.8 | 97.4 |
| Body Weight (kg) | 85.5 ± 16.5 | 86.0 ± 20.6 |
| Rheumatoid Factor negative (%) | 90.1 | 89.4 |
| Duration of Psoriatic Arthritis (years) | 9.2 ± 8.7 | 9.8 ± 8.3 |
| Duration of Psoriasis (years) | 17.1 ± 12.6 | 17.2 ± 12.0 |
| No. of previous DMARDs | 1.5 ± 1.2 | 1.5 ± 1.2 |
| % MTX use | 50.0 | 51.0 |

*Mean values ± standard deviations, except percentages.

The study design for Study G was as follows. 313 patients were randomized during a screening period. At week 0, patients were split into two groups: the first group included 151 patients who received 40 mg every other week of Adalimumab; and the second group included 162 patients who received placebo every other week. The study was conducted in a double blind manner for 24 weeks. Statistical analysis was conducted at week 24.

Patients were exclude for prior anti-TNF therapy; Alefacept within 12 weeks prior to study entry; other biologics within 6 weeks prior to study entry; DMARDs (except MTX) within 4 weeks prior to study entry; systemic therapies for psoriasis within 4 weeks prior to study entry; and phototherapy and topicals within 2 weeks prior to study entry.

Example 1

Adalimumab is Efficacious in Treating Skin Disease in Psoriatic Arthritis: Subanalysis of Moderate Vs. Severe Psoriasis A study was performed to evaluate whether the efficacy of adalimumab for cutaneous disease in patients with psoriatic arthritis (PsA) varies with severity of psoriasis. Prior to this study, it was unknown whether the response of psoriasis to adalimumab therapy in previous, related studies was affected by the level of skin disease at baseline.

A randomized Phase III study of adalimumab was studied in patients with active PsA (=3 swollen and =3 tender joints) who had failed NSAID therapy (see above description of Study G). Randomization was centrally stratified by methotrexate (MTX) use and extent of psoriasis (<3% or =3% body surface area [BSA]) at baseline. Patients completing Week 24 were eligible to continue in an open-label extension study.

Patients were included if they had a history of psoriasis; were over 18 years; =3 swollen and =3 tender joints; and inadequate response to NSAID therapy. Exclusion criteria included prior anti-TNF therapy; alefacept within 12 weeks prior to study entry; other biologics within 6 weeks prior to study entry; DMARDs (except MTX) within 4 weeks prior to study entry; systemic therapies for psoriasis within 4 weeks prior to study entry; and phototherapy and topicals within 2 weeks prior to study entry.

Patients were stratified by methotrexate use (yes/no) and degree of psoriasis (<3% and =3% BSA involvement) and received adalimumab 40 mg every other week or placebo for 24 weeks.

Efficacy measures included: ACR response criteria (co-primary endpoint: ACR20 response at Week 12); Psoriasis Area and Severity Index (PASI) in patients with significant psoriasis at study entry (=3% BSA); and Physician's Global Assessment (PGA) of psoriasis. This study examined patients according to the severity of psoriasis at baseline: PASI<10 vs. PASI≥10

Thus, efficacy measures in patients with psoriasis affecting =3% BSA at baseline included PASI, PGA of psoriasis, and DLQI. ACR response criteria was also used as an efficacy measurement. A post-hoc analysis was conducted for patients with baseline PASI<10 vs. those with PASI=10. PASI analyses were by NRI, and PGA and DLQI scores were calculated as LOCF. Table 2 shows the baseline psoriasis scores of adalimumab-treated patients grouped by psoriatic severity.

TABLE 2

Baseline psoriasis scores of adalimumab-treated patients grouped by psoriatic severity.

| Characteristics* | PASI < 10 N = 53 | PASI ≥ 10 N = 16 |
|---|---|---|
| Mean PASI ± SD (0-72) | 4.8 ± 2.4 | 16.1 ± 6.4 |
| PGA "Clear" or "Almost Clear" | 1 (1.9%) | 0 (0%) |
| Mean DLQI ± SD* | 6.6 ± 4.8 | 15.4 ± 7.8 |

*N values for mean DLQI at baseline are 51 (PASI < 10) and 14 (PASI ≥ 10).

Baseline data was similar between the groups. ACR responses were significantly better with adalimumab than placebo, as ACR20/50/70 responses at Week 24 were 57*/39*/23* for adalimumab vs. 15/6/1 for placebo (*p≤0.001, placebo vs. adalimumab).

PASI responses were evaluated for 138 of 313 enrolled patients. Baseline data for this subset were also well-matched, with baseline PASI scores of 7.4±6.1 for adalimumab and 8.3±7.3 for placebo.

PASI responses had rapid onset and were maintained out to Week 24, when approximately half of adalimumab patients had achieved a PASI 90 response. The trend in mean percent improvement in PASI scores over 24 weeks is described in FIG. 1. Overall, PASI 50/75/90 responses at Week 24 were 75*/59*/42* for adalimumab (n=69) vs. 12/1/0 for placebo (n=69) (*p<0.001 adalimumab vs. placebo, PASI 50/75/90 by non-responder imputation).

PASI responses at week 24 were examined in accordance with disease severity. Of the 69 patients on adalimumab who were evaluated for PASI response, 53 had mild to moderate psoriasis (baseline PASI<10), and 16 had moderate to severe psoriasis (baseline PASI=10). Mean baseline PASI scores for patients with mild psoriasis vs. patients with moderate to severe psoriasis were 4.8±2.4 vs. 16.1±6.4. At week 24, the two subgroups of adalimumab-treated patients (PASI<10 and PASI≥10) had similar and clinically significant PASI 50, 70, and 90 response rates. After 24 weeks, the % of patients who had achieved PASI50/75/90 response rates were similar: 74*/62*/43* for those with PASI<10 (n=53) and 81*/50*/38† for those with PASI=10 (n=16) (*P≤0.001; †=0.005, for ada vs. placebo, non-responder imputation).

The distribution of PGA scores improved from baseline with 24 weeks of adalimumab treatment in both disease severity groups (PASI<10 and PASI≥10), as shown below in Table 3.

TABLE 3

PGA at Baseline and Week 24 by Disease Severity Including PASI = 10

|  | % Patients with PASI = 10 | |
| --- | --- | --- |
|  | Baseline | Week 24 |
| Severe | 12.5 | 0 |
| Moderate to Severe | 50 | 6.3 |
| Moderate | 25 | 25 |
| Mild to Moderate | 12.5 | 12.5 |
| Mild | 0 | 18.8 |
| Almost Clear | 0 | 18.8 |
| Clear | 0 | 18.8 |

The percentage of patients with a PGA of "Clear" or "Almost Clear" at 24 weeks was 76% for those with PASI<10 and 38% for those with PASI=10, as shown in Table 4.

TABLE 4

Percentage of Patients with PGA of "Almost Clear" or "Clear"

|  | PASI < 10 | | PASI = 10 | |
| --- | --- | --- | --- | --- |
|  | Placebo (n = 50) | Adalimumab (n = 53) | Placebo (n = 19) | Adalimumab (n = 16) |
| % of Patients with PGA of "Clear" or "Almost Clear" | 14 | 76* | 0 | 38† |

*P < 0.001,
†P < 0.01 adalimumab vs. placebo (placebo data not shown)

For patients with moderate psoriasis, the PGA appeared to correlate with PASI 50-75 responses; for patients with severe psoriasis, the correlation was with PASI 90.

At week 24, both subgroups of adalimumab-treated patients (PASI<10 and PASI=10) achieved meaningful improvements in quality of life as measure by DLQI. Mean change in DLQI at 24 weeks for patients who received Adalimumab with PASI<10 was −4.6, and for patients who received Adalimumab with PASI=10 it was −10.6. Mean change in DLQI at 24 weeks for patients who received placebo with PASI<10 was −0.6, and −0.9 for patients who received placebo with PASI=10. Quality of life improvements were greater for patients with severe psoriasis. Adalimumab was generally well-tolerated during the trial, as previously reported.

Rates of individual adverse events (AE) and serious adverse events (SAE) were comparable between adalimumab and placebo, as shown below in Table 5.

TABLE 5

Common adverse events >5% at week 24

|  | Placebo eow N = 162 n (%) | Adalimumab 40 mg eow N = 151 n (%) |
| --- | --- | --- |
| Any AE | 130 (80.2) | 122 (80.8) |
| Any SAE | 7 (4.3) | 5 (3.3) |
| Upper Respiratory Tract Infection NOS | 24 (14.8) | 19 (12.6) |
| Nasopharyngitis | 15 (9.3) | 15 (9.9) |
| Injection site reaction NOS | 5 (3.1) | 10 (6.6) |
| Headache | 14 (8.6) | 9 (6.0) |
| Hypertension NOS | 5 (3.1) | 8 (5.3) |
| PsA aggravated | 11 (6.8) | 5 (3.3) |
| Psoriasis aggravated | 10 (6.2) | 3 (2.0) |
| Arthralgia | 9 (5.6) | 3 (2.0) |
| Diarrhea NOS | 9 (5.6) | 3 (2.0) |

In conclusion, adalimumab is efficacious for skin and joint disease in patients with PsA. In this post-hoc analysis, clinically significant improvements were observed for patients with moderate to severe psoriasis, as well as those with mild to moderate psoriasis. Thus, the baseline severity of skin disease did not affect the efficacy of adalimumab in the treatment of psoriasis.

Example 2

Correlation of Skin and Joint Responses in Psoriatic Arthritis

Previous studies have shown that anti-TNF therapy with adalimumab (ada) is efficacious against the arthritis and skin disease of psoriatic arthritis (PsA) for up to 24 weeks (wks). Patients (pts) completing Study G were eligible to enroll in an open-label extension (OLE) trial. The objective of this study was to evaluate the frequency of concurrent joint and skin responses in PsA patients treated with ada for up to 48 wks in Study G (described above).

Patients completing the 24-week trial were eligible to enroll in an OLE study to receive ada 40 mg eow. Skin responses were evaluated only in patients with psoriasis affecting =3% BSA at baseline. For the present post-hoc subanalysis, these patients were categorized according to the response to treatment of psoriasis (PASI nonresponse, 50, 75, 90) and of arthritis (ACR nonresponse, 20, 50, 70) at Wks 24 and 48, compared to baseline. ACR and PASI scores were analyzed in the intent-to-treat population, using non-responder imputation for missing data.

Baseline demographics/disease characteristics were similar between randomization groups (162 placebo, 151 ada). For patients with baseline psoriasis affecting =3% BSA (69 placebo, 69 ada), mean baseline PASI scores were 8.3 and 7.4. In these 138 patients, at Wk 24 the response rates for ACR20/50/70 were 14/6/0 (placebo) and 54/36/23 (ada), and for PASI 50/75/90 were 12/1/0 (placebo) and 75/59/42 (ada). Among the 69 patients in the ada arm, an ACR20 and/or PASI75 response was achieved by 75% at Wk 24 and by 68% at Wk 48. Simultaneous ACR20 and PASI70 responses were achieved by 38% and 45% at Wks 24 and 48, and simultaneous ACR70 and PASI75 responses were achieved by 22% and 26% at Wks 24 and 48, respectively. Among ada patients who achieved an ACR50 or an ACR70 response, a PASI75 response was achieved at Wk 24 by 84% and 94%, respectively, and at Wk 48 by 83% and 95% (Table 6).

TABLE 6

PASI responses among patients with an ACR20, 50, or 70 response

| | Week 24 | | | Week 48 | | |
|---|---|---|---|---|---|---|
| | ACR20 n = 37 | ACR50 n = 25 | ACR70 N = 16 | ACR20 n = 38 | ACR50 n = 29 | ACR70 n = 19 |
| PASI50 % | 86 | 92 | 94 | 87 | 90 | 100 |
| PASI75 % | 70 | 84 | 94 | 82 | 83 | 95 |
| PASI90 % | 54 | 64 | 69 | 61 | 62 | 63 |

*Numbers of ada-treated patients, of 69 total, with the indicated level of ACR response at Wks 24 or 48, compared with baseline; PASI responses are % of the above n values.

Furthermore, among ACR non-responders (<ACR20), a PASI75 or PASI90 response was achieved at Wk 24 by 47% and 28%, respectively, and at Wk 48 by 29% and 29%.

As shown in Table 7 (below), 30% of evaluated patients (n=69) achieved concurrent ACR50 and PASI 75 responses. In addition, 16% of patients achieved concurrent ACR70 and PASI 90 responses.

TABLE 7

Concurrent Skin-Joint Responses at Week 24

| | PASI 75 | PASI 90 |
|---|---|---|
| % patients with ACR20 | 38 | 29 |
| % patients with ACR50 | 30 | 23 |
| % patients with ACR70 | 22 | 16 |

At week 24, 47% of patients with <ACR20 response, i.e., ACR non-responders, achieved a PASI 75 response, and 70% of ACR20 responders achieved a PASI 75 response. Furthermore, 84% of ACR50 responders and 94% of ACR70 responders achieved a PASI 75 response. ACR response rates were higher for patients who achieved a ≥PASI 75 response than those who did not (see Table 8).

TABLE 8

ACR Response Rates for PASI75 Responders at Week 24

| | PASI < 75 | PASI = 75 |
|---|---|---|
| % patients with ACR20 | 39 | 63 |
| % patients with ACR50 | 14 | 51 |
| % patients with ACR70 | 4 | 37 |

In conclusion, adalimumab was simultaneously efficacious against the skin disease and joint inflammation of patients with PsA. Simultaneous ACR70 and PASI75 responses occurred in 26% of ada-treated patients. PASI75 responses were frequent among ada-treated ACR non-responders (<ACR20) and as the level of joint response increased, the frequency of PASI 75 skin response also increased, reaching 95% in ACR70 responders. Concurrent high-level skin and joint responses were frequent, with 30% of patients achieving both a PASI 75 and an ACR50 response. Finally, as the level of one type of response (skin or joint) increased, so did the frequency of the other, with 94% of ACR70 responders also having a PASI 75 response.

Example 3

Adalimumab is Efficacious in Treating Skin Disease in Psoriatic Arthritis: Subanalysis by Severity of Psoriasis Results from Study G demonstrated that adalimumab (ada) is an effective treatment for the joint and skin disease of psoriatic arthritis (PsA) for up to 24 wks. Patients (pts) completing Study G were eligible to enroll in an open label extension (OLE) trial. The relationship between the severity of skin disease in Study G patients, and the efficacy of ada as treatment for PsA skin disease, is described in the instant example.

This study was conducted to determine the 48-week efficacy of ada for PsA skin disease in patients with mild-to-moderate versus moderate-to-severe psoriasis (Ps) at baseline (BL). The present post-hoc analysis examined subgroups of patients enrolled in Study G (see above for description of study characteristics) with mild-to-moderate Ps (PASI<10) vs. moderate-to-severe Ps (PASI=10) at BL. Analyses were conducted on the ITT population, using NRI for the PASI response rates and LOCF for the Psoriasis Area and Severity Index (PASI), Physician's Global Assessment (PGA) and Dermatology Life Quality Index (DLQI).

A total of 313 patients (151 ada, 162 pbo) enrolled in Study G and 285 entered the OLE. BL data were similar between randomization groups. PASI responses were evaluated for 138 patients (69 ada, 69 pbo), in whom BL data were well matched, and the BL PASI scores were 7.4±6.1 for ada and 8.3±7.3 for pbo. Overall, PASI 50/75/90 responses at Week 24 were 75/59/42 for ada versus 12/1/0 for pbo, and at Week 48 were 70/58/46 for patients from the ada randomization arm. Among the 69 ada patients in whom skin efficacy was evaluated, the BL PASI was <10 in 53 patients (mean PASI, 4.8±2.4) and was =10 in 16 patients (mean PASI, 16.1±6.4). At Weeks 24 and 48, the mean PASI score and the DLQI both showed larger improvement in the PASI=10 group (Table 9), whereas this difference was not seen in the PASI50/75/90 responses (PASI<10: 74/62/43 Wk 24 and 72/66/51 Wk 48; PASI=10: 81/50/38 and 63/31/31;

p>0.05, for all comparisons). Consistent with their milder skin disease at BL, the PASI<10 group had better PGA results than the PASI=10 group (see Table 9). These Week 24 PASI, DLQI and PGA results were all significantly better than observed in the corresponding pbo patients (p≤0.001 for PASI<10; p≤0.005 for PASI≥10).

TABLE 9

Psoriasis-related changes following ada in Study G patients by baseline Ps severity.

|  | PASI | | PASI90 | | DLQI | | PGA | |
| --- | --- | --- | --- | --- | --- | --- | --- | --- |
|  | PASI < 10 n = 53 | PASI ≥ 10 n = 16 | PASI < 10 n = 53 | PASI ≥ 10 n = 16 | PASI < 10 n = 51 | PASI ≥ 10 n = 14 | PASI < 10 n = 53 | PASI ≥ 10 N = 16 |
| Baseline | 4.8 | 16.1 |  |  | 6.6 | 15.4 | 2 | 0 |
| Wk 24* | −3.6 | −10.7 | 43 | 38 | −4.6 | −10.6 | 76 | 38 |
| Wk 48* | −3.8 | −10.0 | 51 | 31 | −4.1 | −8.1 | 72 | 31 |

*Mean change from baseline for PASI, DLQI, % for PASI90 and PGA clear or almost clear.

Ada generally had a good safety profile and was well-tolerated during the blinded phase of Study G and the first 24 weeks of the OLE trial.

In conclusion, clinically meaningful improvements were observed for patients with moderate-to-severe Ps, as well as those with mild-to-moderate Ps in this post-hoc analysis of PsA patients treated for 48 weeks.

Example 4

Adalimumab Efficacy in Psoriatic Arthritis Patients with Oligoarticular Arthritis Initial studies from Study G have shown that anti-TNF treatment with adalimumab (ada) is efficacious for arthritis and skin disease of psoriatic arthritis (PsA) for up to 24 weeks. Patients (pts) completing Study G could enroll in an open-label extension (OLE) trial. Most patients in Study G had polyarticular arthritis. The effect of ada on the subset of PsA patients with oligoarticular arthritis, as originally defined by Moll and Wright (Wright and Moll. Psoriatic arthritis. *Seronegative polyarthritis*. Amsterdam: North Holland Publishing Co, 1976:169-223) was not known prior to this study. Thus, the purpose of this study was to determine the efficacy of ada for arthritis and physical function of PsA patients with oligoarthritis in Study G.

Study G is described above. The present post-hoc analysis examined subgroups of patients who had oligoarthritis at baseline (BL), defined as a tender joint count (TJC)<5 or a swollen joint count (SJC)<5. Analyses were conducted on the intention to treat population (ITT population), using nonresponder imputation for the ACR response rates and last observation carried forward for the HAQ-DI scores.

A total of 313 patients (151 ada, 162 pbo) enrolled in Study G and 285 entered the OLE. BL data were similar between randomization groups. ACR20/50/70 responses and the mean change in HAQ scores at Week 24 were 57/39/23 and −0.4, respectively, for ada patients vs. 15/6/1 and −0.1 for pbo patients, and at Week 48 were 61/46/31 and −0.4 for patients from the ada randomization arm. At Week 24, the ACR responses and mean change in HAQ scores of ada-treated patients with BL TJC<5 or SJC<5 were comparable to those of the overall ada cohort in Study G (Table 10). In ada-treated patients with SJC<5, the Week 24 ACR responses (p<0.05) and mean change in HAQ scores (p<0.01) were superior to those of patients treated with pbo (Table 10). ACR responses and mean change in HAQ scores in ada-treated patients with TJC<5 or SJC<5 were maintained at Week 48 (Table 10).

TABLE 10

Clinical responses in PsA patients with Oligoarthritis in Study G

|  |  | TJC < 5 | | SJC < 5 | |
| --- | --- | --- | --- | --- | --- |
|  |  | Ada n = 10 | Pbo n = 5 | Ada n = 24 | Pbo n = 17 |
| ACR20/50/70 | Wk 24 | 60/20/0 | 20/0/0 | 58*/42/*29* | 18/6/0 |
| ACR20/50/70 | Wk 48 | 50/40/20 | N/A | 63/54/50 | N/A |
| HAQ baseline |  | 0.6 | 0.6 | 0.9 | 1.0 |
| Mean Δ HAQ | Wk 24 | −0.3 | 0 | −0.5** | 0 |
| Mean Δ HAQ | Wk 48 | −0.2 | N/A | −0.5 | N/A |

*p < 0.05,
**p < 0.01 ada vs. placebo;
N/A., not available because pbo patients received ada after Week 24; Week 48 results are for ada randomization arm patients only vs. baseline.
p values not determined for Week 48.

In conclusion, while the numbers of patients with oligoarthritis is small, the results indicate improvements in arthritis and physical function that are comparable to those of the overall PsA trial population. Thus, adalimumab was effective at treating this specific subpopulation of PsA patients.

Example 5

Adalimumab is Efficacious in Treating Joint Disease in Early and Established Psoriatic Arthritis Patients (pts) completing Study G were eligible to enroll in an open label extension (OLE) trial. The objective of this study was to determine the 24- and 48-week efficacy of adalimumab (ada) for arthritis and disability in Study G patients classified according to disease duration at baseline (BL).

Study G is described above. Upon completion of Study G, ada and placebo (pbo) patients were eligible to receive ada 40 mg every other week (eow) in the OLE trial; a dosage increase to 40 mg weekly was allowed on or after Week 36 for patients with <20% improvement in TJC and <20% improvement in SJC. The present post-hoc analysis categorized patients according to PsA duration as follows: <2, 2 to <5, 5 to <10, and ≥10 years at baseline. Analyses were conducted on the intention to treat population (ITT population), using non-responder imputation (NRI) for the ACR scores and last observation carried forward (LOCF) for other clinical scores.

This post-hoc subanalysis examined patients according to the duration of PsA at baseline: <2, 2-5, 5-10, and ≥10 years. For patients randomized to adalimumab, analysis was for the intention-to treat population to Week 48. While patients were randomized to placebo, analysis was for the intention-to treat population to Week 24 and for patients who received open-label adalimumab, from Weeks 24 to 48. Table 3 shows baseline psoriasis scores of adalimumab-treated patients grouped by psoriatic severity.

When data were missing, and for post-escalation results of patients who escalated to weekly adalimumab dosing on or after Week 36, ACR and PASI responses were called nonresponder (non-responder imputation), and all other clinical scores were carried forward from the last previous observation. P values were calculated only for Week 24 results, and not for open-label extension results (i.e., Week 48)

Baseline data were similar between randomization groups of patients enrolled in Study G. ACR20/50/70 responses at Week 24 were 57/39/23 for ada vs. 15/6/1 for pbo, and at Week 48 were 61/46/31 for patients from the ada randomization arm. Among patients in the ada treatment arm, baseline PsA disease duration was <2 years for 26 patients, 2-5 yrs for 29 patients, 5-10 yrs for 35 patients and ≥10 yrs for 61 patients (Table 11). Within each ada disease-duration group, the ACR20/50/70 response rates, and mean changes in tender joint counts (TJC), swollen joint counts (SJC), HAQ scores, CRP concentrations and DAS28 scores at Week 24 were better than in the corresponding groups of placebo patients (see Table 11). No significant differences were observed in comparisons of these Week 24 measures across the four disease-duration groups.

TABLE 11

Arthritis-related outcomes at Week 24 among ada-treated patients by PsA disease duration

| | PsA duration, years (N) | | | |
|---|---|---|---|---|
| | <2 (26) | 2-5 (29) | 5-10 (35) | ≥10 (61) |
| ACR 20/50/70 | 46*/38/23† | 66/52/28 | 54/34*/23† | 59/36/20† |
| Baseline HAQ | 0.8 | 0.9 | 1.0 | 1.0 |
| Mean Δ HAQ | −0.3* | −0.5 | −0.3† | −0.4 |
| Baseline DAS28 | 4.7 | 4.6 | 4.8 | 4.9 |
| Mean Δ DAS28 | −1.5 | −1.7 | −1.5 | −1.8 |

*p < 0.05,
†p < 0.01,
†not significant; all other results p < 0.001; ada vs. pbo (pbo data not shown)

Table 12 shows mean changes in tender and swollen joint counts (TJC, SJC) and CRP concentrations were better than in the corresponding groups of placebo patients (data not shown).

TABLE 12

Baseline Clinical Characteristics of Adalimumab-Treated Patients by Disease Duration

| | Overall (N = 151) | <2 years (n = 26) | 2-5 years (n = 29) | 5-10 years (n = 35) | ≥10 years (n = 61) |
|---|---|---|---|---|---|
| HAQ (0-3) | 1.0 ± 0.6 | 0.8 ± 0.6 | 0.9 ± 0.6 | 1.0 ± 0.6 | 1.0 ± 0.7 |
| DAS28 | 4.8 ± 1.1 | 4.7 ± 1.1 | 4.6 ± 0.9 | 4.8 ± 1.2 | 4.9 ± 1.1 |
| Tender Joint Count (0-78) | 23.9 ± 17.3 | 26.3 ± 14.7 | 18.2 ± 15.1 | 25.3 ± 19.5 | 24.9 ± 17.9 |
| Swollen Joint Count (0-76) | 14.3 ± 12.2 | 15.8 ± 14.9 | 13.4 ± 11.4 | 14.7 ± 12.4 | 14.0 ± 11.3 |
| C-Reactive Protein (mg/dL) | 1.4 ± 2.1 | 1.0 ± 1.2 | 1.7 ± 1.8 | 1.1 ± 1.1 | 1.6 ± 2.8 |
| | n = 69 | n = 13 | n = 10 | N = 18 | n = 28 |
| PASI (0-72) | 7.4 ± 6.1 | 7.2 ± 5.6 | 10.0 ± 11.3 | 6.9 ± 4.3 | 7.0 ± 4.6 |

Values are mean ± SD.

ACR20, 50, and 70 responses rates established with adalimumab at Week 24 were maintained to Week 48 as shown in Table 13. Similar ACR responses occurred in placebo patients upon receiving 24 weeks of open-label adalimumab.

TABLE 13

ACR Responses at Weeks 24 and 48

|  | Double Blind (Week 24) | | Open-label (Week 48) | |
|---|---|---|---|---|
|  | Placebo (n = 162) | Adalimumab (n = 151) | Placebo/ Adalimumab (n = 147) | Adalimumab (n = 151) |
| % Patients with ACR 20 | 15 | 57* | 54 | 61 |
| % Patients with ACR 50 | 6 | 39* | 37 | 46 |
| % Patients with ACR 70 | 1 | 23* | 21 | 31 |

*$p < 0.001$, adalimumab vs. placebo. Non-responder imputation

ACR20, 50, and 70 response rates with adalimumab were significantly better than placebo at Week 24 (Table 14) regardless of PsA disease duration.

TABLE 14

| | Disease Duration | | | |
|---|---|---|---|---|
| | <2 years (n = 26) | 2-5 years (n = 29) | 5-10 years (n = 35) | =10 years (n = 61) |
| % Patients with ACR 20 | 46± | 66* | 54* | 59* |
| % Patients with ACR 50 | 38* | 52* | 34± | 36* |
| % Patients with ACR 70 | 23† | 28* | 23† | 20† |

*$p = 0.001$,
†$p < 0.01$,
±$p < 0.05$ vs. placebo (placebo data not shown for disease duration categories) Non-responder imputation.

In all disease duration categories of patients from the adalimumab arm of Study G, ACR response rates were maintained to Week 48 (see Table 15).

TABLE 15

ACR Response rates in Adalimumab Treated Patients at Week 48 by Baseline Duration

| | Disease Duration | | | |
|---|---|---|---|---|
| | <2 years (n = 26) | 2-5 years (n = 29) | 5-10 years (n = 35) | =10 years (n = 61) |
| % Patients with ACR 20 | 50 | 66 | 51 | 57 |
| % Patients with ACR 50 | 46 | 59 | 37 | 39 |
| % Patients with ACR 70 | 38 | 38 | 31 | 21 |

Variations in ACR responses rates across disease duration groups may explained by patient numbers and CRP-related differences (Table 12 and Table 16).

TABLE 16

Mean Change in CRP at Weeks 24 and 48 by Disease Duration

| | Disease Duration | | | |
|---|---|---|---|---|
| | <2 years (n = 26) | 2-5 years (n = 29) | 5-10 years (n = 35) | =10 years (n = 61) |
| Mean Change From Baseline at Week 24 | −0.2 | −1.1† | −0.4 | −1.2* |
| Mean Change From Baseline at Week 48 | −0.5 | −1.2 | −.04 | −1.1 |

*$p = 0.001$,
†$p = 0.002$ vs. placebo (not shown), LOCF, LOCF for patients who discontinued or whose dosages were increased.

Similar results were obtained as measured by PASI. PASI 50, 75, and 90 response rates with adalimumab were significantly better than placebo at Week 24 (Table 17) regardless of PsA disease duration.

TABLE 17

PASI Response rates in Adalimumab Treated Patients at Week 24 by Baseline Duration

| | Disease Duration | | | |
|---|---|---|---|---|
| | <2 years (n = 13) | 2-5 years (n = 10) | 5-10 years (n = 18) | =10 years (n = 28) |
| % Patients with PASI 50 | 69± | 80* | 78* | 75* |
| % Patients with PASI 75 | 46† | 60† | 72* | 57* |
| % Patients with PASI 90 | 38± | 40± | 39* | 46* |

In all disease duration categories of patients from the adalimumab arm of Study G, PASI response rates were maintained to Week 48 (Table 18).

TABLE 18

PASI Response rates in Adalimumab Treated Patients at Week 48 by Baseline Duration

| | Disease Duration | | | |
|---|---|---|---|---|
| | <2 years (n = 13) | 2-5 years (n = 10) | 5-10 years (n = 18) | =10 years (n = 28) |
| % Patients with PASI 50 | 54 | 50 | 78 | 71 |
| % Patients with PASI 75 | 54 | 40 | 72 | 57 |
| % Patients with PASI 90 | 38 | 40 | 50 | 50 |

HAQ scores also improved significantly more with adalimumab than placebo in most disease duration categories at Week 24 (placebo data not shown) as shown in Table 19. In all disease duration categories, Week 24 improvements in HAQ were maintained to Week 48

TABLE 19

Mean Change in HAQ at Weeks 24 and 48 by Disease Duration

| | Disease Duration | | | |
|---|---|---|---|---|
| | <2 years (n = 26) | 2-5 years (n = 29) | 5-10 years (n = 35) | =10 years (n = 61) |
| Mean Change from Baseline at Week 24 | −0.3† | −0.5* | −0.3 | −0.4* |
| Mean Change from Baseline at Week 48 | −0.3 | −0.5 | −0.3 | −0.4 |

*p = 0.001,
†p < 0.05, vs. placebo (placebo data not shown for disease duration categories.) LOCF.

Table 16 shows that mean CRP concentrations were decreased from baseline in all disease duration subgroups following 24 weeks of adalimumab treatment. Mean CRP reductions were also maintained to Week 48.

Adalimumab-treated patients also achieved significant reductions in their DAS28 scores after 24 weeks of adalimumab treatment compared to placebo, and maintained these improvements to Week 48 regardless of duration of PsA at baseline as shown in Table 20.

TABLE 20

Mean Change in DAS28 Scores at Weeks 24 and 48 by Disease Duration

| | Disease Duration | | | |
|---|---|---|---|---|
| | <2 years (n = 26) | 2-5 years (n = 29) | 5-10 years (n = 35) | =10 years (n = 61) |
| Mean Change from Baseline at Week 24 | −1.5* | −1.7* | −1.5* | −1.8* |
| Mean Change from Baseline at Week 48 | −1.8 | −1.8 | −1.6 | −2.0 |

Figure 2:
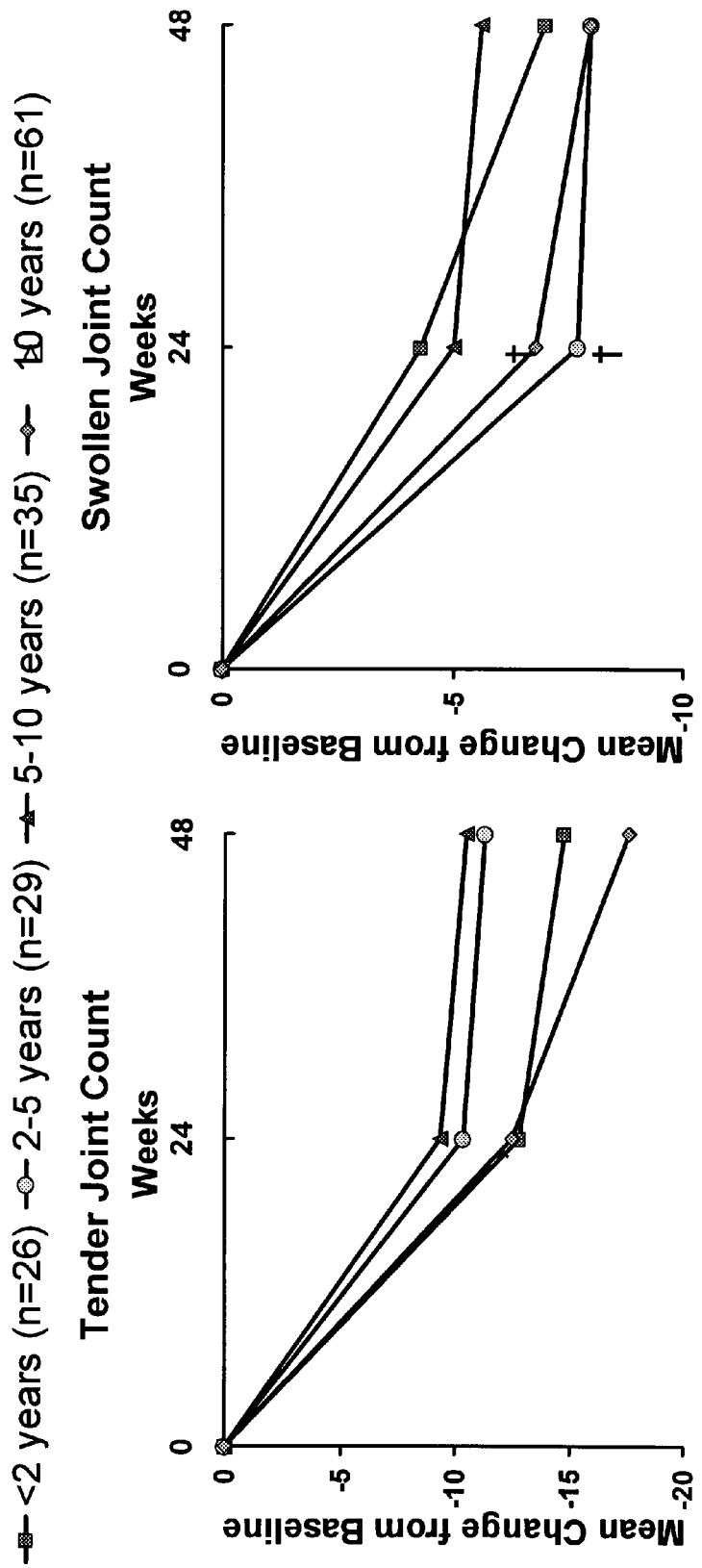
FIG. 2 shows mean changes in TJC and SJC over 48 weeks by disease duration for patients in the study of example 6. $P \leq 0.001$, † $p < 0.01$ vs. placebo (placebo data not shown for disease duration subgroups). Last observation carried forward.

The mean tender and swollen joint counts also declined in all disease duration subgroups treated for 24 weeks with adalimumab and these improvements were maintained to Week 48 as demonstrated in FIG. 2.

Among patients treated with ada for 48 weeks, ACR responses were maintained in each disease-duration group, and the mean changes in TJC, SJC, HAQ, CRP, and DAS28 at Week 48 were all equal to or greater than the mean changes observed at 24 weeks. Ada was generally safe and well-tolerated during the blinded phase of Study G and the first 24 weeks of the OLE trial.

In conclusion, patients with early and late PsA responded well to ada. Furthermore, disease duration did not have any major impact on the therapeutic efficacy of ada for arthritis or physical function in PsA. Thus, adalimumab was effective irrespective of the disease duration of the subject.

Example 6

Complete Resolution of Arthritis- and Dermatologic Related Functional Loss with Adalimumab in Patients with Psoriatic Arthritis Psoriatic arthritis (PsA) is a condition associated with significant disability and functional loss related to both skin and joint components of disease. Between 11% and 15% of patients with PsA suffer from long term disability. The psoriatic component of PsA is associated with significant functional loss, including physical complaints with significant psychosocial impact. Previous studies in patients with PsA have shown that administration of adalimumab provides benefits in improving both joint and psoriatic components of disease.

The object of this study was to assess whether adalimumab at a dose of 40 mg every other week (eow) provided complete resolution of loss of physical function in patients with PsA versus those on placebo.

The methods of the study have been described previously in Example 1, including the Study G phase III randomized-controlled trial, wherein physical function was assessed during 24 weeks of treatment. The inclusion criteria is described above.

Physical function assessment was determined using the Disability Index of Heath Assessment Questionnaire (HAQ DI), which includes functional loss and physical function. HAQ DI scores range from 0 to 3, where a lower score indicates less functional loss. The Dermatology Life Quality Index (DLQI) was also used. The DLQI examines changes in dermatologic-related functional limitations, and was used with a subset of patients with BSA>3%. DLQI scores range from 0 to 30, where a lower score indicates less impairment.

Statistical analysis was performed between group percentages of patients with complete resolution of functional loss (HAQ DI or DLQI equal to 0) at weeks 12 and 24. 313 patients were given treatment, 151 received adalimumab at a dose of 40 mg every other week, and 162 received placebo. Baseline characteristics were similar between these two treatment groups, and consistent with moderate to severely active PsA. The mean baseline HAQ DI was 1.0 in both groups, and the mean DLQI total score was 8.6 (SD=6.61) in the adalimumab group and 10.3 (SD=7.49) in the placebo group.

At weeks 12 and 24, significantly more patients in the adalimumab group had no functional loss (HAQ DI=0) versus those treated with placebo. At week 12, 34% of adalimumab group patients had an HAQ DI=0, whereas only 14% of the placebo group had such a score. At week 24, 34% of adalimumab group patients had an HAQ DI=0, whereas only 14% of the placebo group had such a score.

In a subset of patients with BSA≥3%, at week 12 significantly more patients in the adalimumab group had no dermatologic-related functional limitations (DLQI=0) versus those treated with placebo (40% ada vs. 5% placebo). By week 24, 40% more patients treated with adalimumab 40 mg eow experienced complete resolution of dermatologic-related functional limitations than patients treated with placebo (45% ada vs. 5% placebo).

In sum, between 30-40% of moderate to severely active PsA patients experienced complete resolution of general or dermatologic-related functional loss when treated with adalimumab 40 mg eow—compared with only 5% with placebo. Adalimumab reversed debilitating disease effects on physical function early in therapy and provided sustained benefit with continued treatment.

Example 7

Effectiveness of Adalimumab in Psoriatic Arthritis Patients with Oligoarticular Arthritis TNF concentrations are elevated in skin lesions and joints in patients with PsA. Previous studies have shown that anti-TNF therapy with Adalimumab is efficacious against the arthritis and the skin disease of PsA. The majority of patients in these previous studies also had active, polyarticular arthritis.

The purpose of this study was to determine whether ACR response rates in the Study G study differed between patients with oligoarticular arthritis and patients with involvement of ≥5 joints. The inclusion and exclusion criteria for patients in the phase III Study G study is described above. Efficacy was measured using the ACR response and the primary endpoint was ACR20 at week 12. Data was assessed using intent-to-treat (ITT) analysis with non-responder imputation. Baseline disease characteristics are described below in Table 21:

TABLE 21

Baseline Disease Characteristics

| Characteristic* | Placebo EOW N = 162 | Adalimumab 40 mg EOW N = 151 |
|---|---|---|
| Swollen Joint Count (0-76) | 14.3 ± 11.1 | 14.3 ± 12.2 |
| Tender Joint Count (0-78) | 25.8 ± 18.0 | 23.9 ± 17.3 |
| C-Reactive Protein (mg/dl) | 1.4 ± 1.7 | 1.4 ± 2.1 |
| HAQ (0-3) | 1.0 ± 0.7 | 1.0 ± 0.6 |
|  | n = 69† | n = 70† |
| PASI (0-72) | 8.3 ± 7.3 | 7.4 ± 6.1 |
| (Range) | (0.4-40.9) | (0.2-38.0) |
| PGA ("Clear" or "Almost Clear") | 1 (1.4%) | 1 (1.4%) |

*Mean values ± SD, except percentages
†Patients with BSA ≥3%; N + 69 for PASI scores of adalimumab-treated patients The percentage of polyarthritis patients with oligoarthritis (TJC<5 or SJC<5) was as follows:
Placebo (n=162)
 9.3% (n=15) had SJC<5 only
 1.9% (n=3) had TJC<5 only
 1.2% (n=2) had both
Adalimumab (n=151)
 10.6% (n=16) had SJC<5 only
 1.3% (n=2) had TJC<5 only
 5.3% (n=8) had both At week 12, the ACR20 response rate for the whole cohort was higher for adalimumab than placebo (58% vs. 14%; p<0.001) and at week 24 this difference was maintained for all levels of ACR responses (ACR 20/50/70 adalimumab, 57/39/23; placebo 15/6/1). In patients with TJC<5 or SJC<5 at baseline, the ACR response rates for patients receiving adalimumab were comparable to those of the overall adalimumab cohort, and higher than those of patients with TJC<5 or SJC<5 treated with placebo. Percentages of patients having ACR 20/50/70 responses at week 12 for patients with TJC<5, included the following: 0%/0%/0% placebo (n=5) vs. 70%*/30%/10% adalimumab (n=10) (*p<0.05 vs. placebo, non-responder imputation). Percentages of patients having ACR 20/50/70 responses at week 24 for patients with TJC<5, included the following: 20%/0%/0% placebo (n=5) vs. 63%*/38%*/21% adalimumab (n=10) (non-responder imputation). Percentages of patients having ACR 20/50/70 responses at week 12 for patients with SJC<5, included the following: 18%/0%/0% placebo (n=17) vs. 70%*/30%/10% adalimumab (n=24) (*p<0.01 vs. placebo, non-responder imputation). Percentages of patients having ACR 20/50/70 responses at week 24 for patients with SJC<5, included the following: 18%/6%/0% placebo (n=17) vs. 58%†/42%†/29%† adalimumab (n=24) († p<0.05 vs. placebo, non-responder imputation).

The baseline HAQ scores for patients with TJC<5 at baseline were 0.6 for both the placebo and adalimumab groups respectively. The baseline HAQ scores for patients with SJC<5 at baseline were 1.0 and 0.9 for the placebo and adalimumab groups respectively. There was an overall improvement in the HAQ scores in patients receiving adalimumab.

Mean changes in HAQ scores at week 12 and week 24 for patients with TJC<5 included week 12: −0.1 placebo (n=5) and −0.3 adalimumab (n=10), and at week 24: 0.0 placebo (n=5) and −0.3 adalimumab (n=10). Mean changes in HAQ scores at week 12 and week 24 for patients with SJC<5 included week 12: −0.1 placebo (n=17) and −0.4 adalimumab (n=24), and at week 24: 0.0 placebo (n=17) and −0.5*adalimumab (n=24) (*p<0.01 vs. placebo, non-responder imputation).

In sum, this study showed that in the subset of patients with oligoarticular disease, efficacy appeared to be comparable to that seen in the overall study population, which was dominated by patients with active polyarticular disease. Adalimumab was effective at treating patients with oligoarticular arthritis.

Example 8

Enhanced Efficacy Following Dose Escalation in Patients with Moderate to Severe Psoriatic Arthritis Who have Subtherapeutic Response to Adalimumab Eow Dosing This study was based in part on Study G, a double-blind, placebo-controlled, 24-week (wk) Phase III study of adalimumab 40 mg eow in patients (pts) with active PsA (=3 swollen and =3 tender joints). Study G, as described above and in Mease et al. ((2005) *Arthritis Rheum* 52: 3279-3289, incorporated herein by reference), demonstrated clinically meaningful and statistically significant improvement in skin and joint outcomes at Wk 24 (ACR20 of 57%, PASI75 of 59% in adalimumab patients vs. ACR20 of 15%, PASI75 of 1% in placebo patients). Patients completing Study G and a smaller 12-wk, Phase III PsA study (Study X), were eligible to enroll in an open-label extension study (OLES). This example describes the efficacy and safety in patients who started adalimumab 40 mg weekly in the OLES.

Efficacy and safety data were collected from the earlier randomized, placebo-controlled, double blind trials, i.e., Studies G and X. The design of Study X was as follows. After an initial screening period, 100 patients were randomized. 51 patients received 40 mg of Adalimumab(ada) every other week, for a 12 week period, and 49 patients received placebo every other week for a 12 week period. The study was conducted in a double blind manner. Statistical analysis was conducted at week 12.

In Study G, patients were randomized 1-to-1 to receive placebo or ada 40 mg eow, administered subcutaneously. Patients completing the Phase III studies (Study G and Study X), were eligible to continue in an open-label extension study (described in this example) in which all patients received active therapy (ada 40 mg eow). Placebo patients were switched to adalimumab 40 mg eow when they enrolled in the OLES, and adalimumab patients continued on their previous regimen.

Inclusion criteria for patients included in this study included: =3 swollen and =3 tender joints; inadequate response to DMARD or NSAID therapy; a history of psoriasis; and a minimum age of 18. Patients with prior anti-TNF therapy were excluded.

Efficacy measures included: ACR response criteria (co-primary endpoint: ACR20 response at Week 12); tender and swollen joint counts; health assessment questionnaire disability index (HAQ); and psoriasis area and severity index (PASI) in patients enrolled from Study G with significant psoriasis at study entry (=3% BSA). After 12 wks in the OLES, those patients with less than 20% improvement in both swollen and tender joint counts compared to Wk 0 of the Phase III study were allowed to increase their adalimumab dose to 40 mg wkly. Skin and joint outcomes, along with safety, were assessed up to 36 wks after dose escalation.

Results

Week 12 of this study was the first time point at which patients with subtherapeutic response to adalimumab were eligible for dosage escalation. Weekly dosing was allowed after week 12 only in those patients with a =20% improvement in tender joint count and swollen joint count relative to respective baseline values from Study G or the smaller study. The observed responses at week 12 are shown in Table 22. As can be seen in Table 22, at week 12 of this OLES study, 47% of adalimumab-treated and 58% of placebo/adalimumab-treated patients who enrolled from Study G had achieved ACR20 responses. A majority of the skin-evaluable patients enrolled from Study G had achieved PASI 50 responses by week 12 as well. ACR20 responses at week 12 of the OLES study for patients enrolled from Study X were similar to those of patients enrolled from Study G.

TABLE 22

Overall Joint and Skin Responses Prior to Dosage Escalation for Patients Enrolling from Study G: Observed Responses at Week 12 of OLES

|  | After 36 weeks of adalimumab 40 mg eow (adalimumab arm) | After 12 weeks adalimumab 40 mg eow (placebo→adalimumab arm) |
|---|---|---|
|  | (n = 136) | (n = 143) |
| ACR20 (%) | 58 | 47 |
| ACR50 (%) | 39 | 31 |
| ACR70 (%) | 30 | 14 |
| Skin-evaluable patients (≥3% BSA) | | |
|  | (n = 56) | (n = 61) |
| PASI 50 (%) | 73 | 56 |
| PASI 75 (%) | 62 | 42 |
| PASI 90 (%) | 42 | 27 |

Observed analysis.

The number of patients whose dosages were increased to weekly dosing in the OLES study are shown below in Table 23.

TABLE 23

|  | Received placebo in Study G or Study X | Received adalimumab eow in Study G | Received adalimumab eow in Study X |
|---|---|---|---|
| Week 12 | 26 | 14 | 6 |
| Week 24 | 2 | 1 | 1 |
| Week 36 | 2 | 1 | 0 |

*Week 12, 24, and 36 are relative to start of open-label treatment

Baseline demographics and disease severity characteristics were similar between patients whose dosages were and were not increased with the exception of the number of tender joints at baseline. The baseline demographics and disease characteristics of the patients in this study can be seen in Table 24.

TABLE 24

Baseline Demographics and Disease Characteristics

| Characteristic* | Patients whose dosages were increased (n = 53) | Patients whose dosages were not increased (n = 342) |
|---|---|---|
| Age (years) | 48.8 ± 8.4 | 49.1 ± 12.1 |
| % Male | 49 | 56 |
| % Caucasian | 94 | 96 |
| Body weight (kg) | 90.7 ± 23.3 | 86.3 ± 18.8 |
| Rheumatoid Factor Negative (%) | 93 | 89 |
| Duration of Psoriatic Arthritis (years) | 8.6 ± 8.3 | 9.1 ± 8.3 |
| Duration of Psoriasis (years) | 17.0 ± 13.5 | 16.9 ± 12.1 |
| No. of previous DMARDs | 1.5 ± 1.1 | 1.6 ± 1.2 |
| % MTX Use | 43 | 50 |
| Baseline PASI | 8.9 ± 9.3† | 8.1 ± 6.9† |
| Swollen Joint Count | 17 ± 12 | 14 ± 12 |
| Tender Joint Count | 31 ± 20 | 22 ± 18‡ |
| C-Reactive Protein (mg/dL) | 1.6 ± 1.7 | 1.3 ± 1.9 |
| HAQ | 1.1 ± 0.7 | 0.9 ± 0.6 |

*Mean values ± SD except percentages.
†N = 22 and N = 106 in patients whose dosages were and were not increased, respectively.
‡p < 0.01 vs. patients whose dosages were increased.

Figure 3:
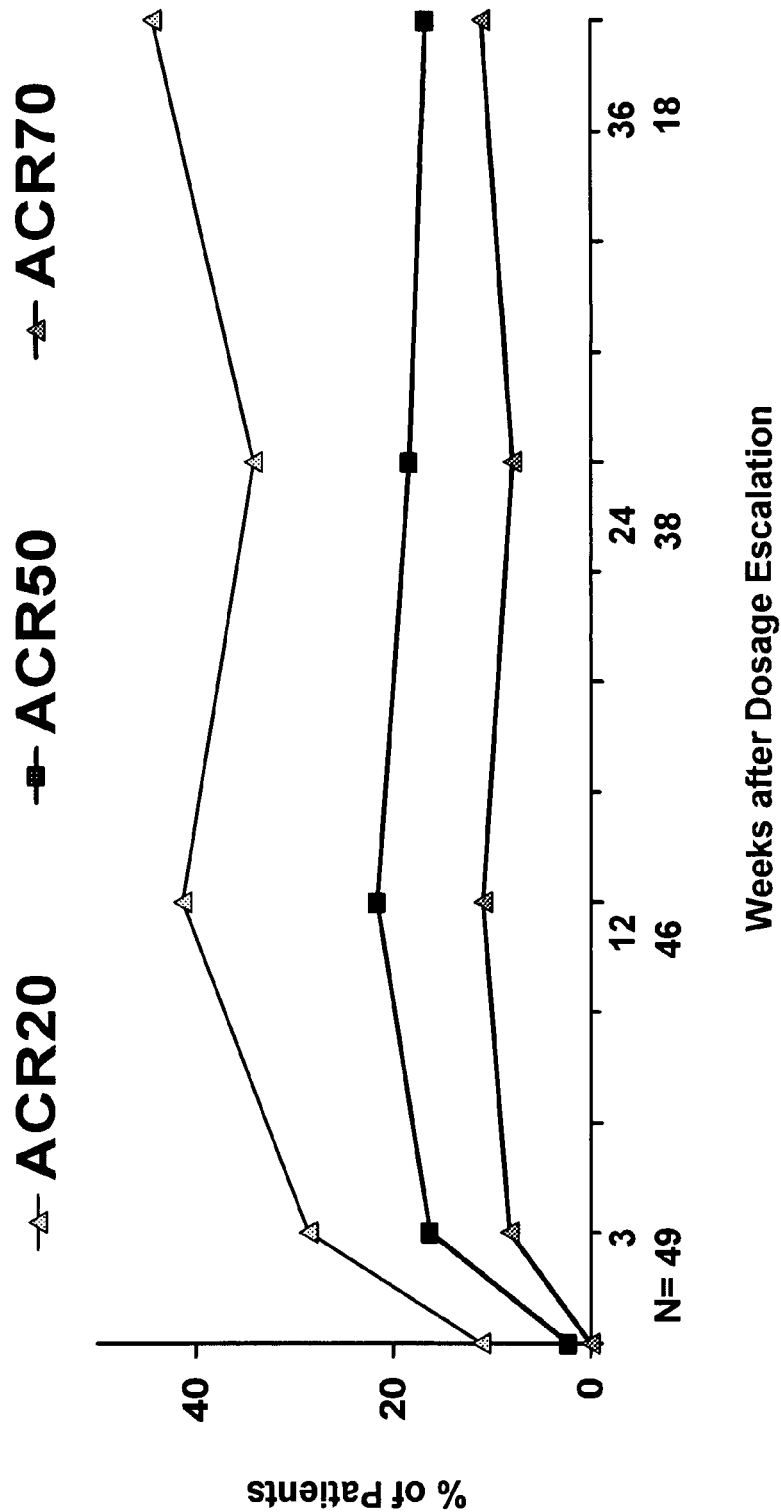
FIG. 3 shows the ACR responses up to 36 weeks after dosage escalation.

ACR response rates in patients whose dosages were increased to weekly dosing had rapid onset and were maintained to 36 weeks after dosage escalation. ACR20 responses exceeded 0% for patients who increased their dosages because dosage escalation was based on swollen joint count and tender joint count improvement relative to baseline values of Study G or Study X, while ACR evaluations were relative to the first dose of adalimumab. FIG. 3 shows the ACR responses after dosage escalation over time.

Figure 4:
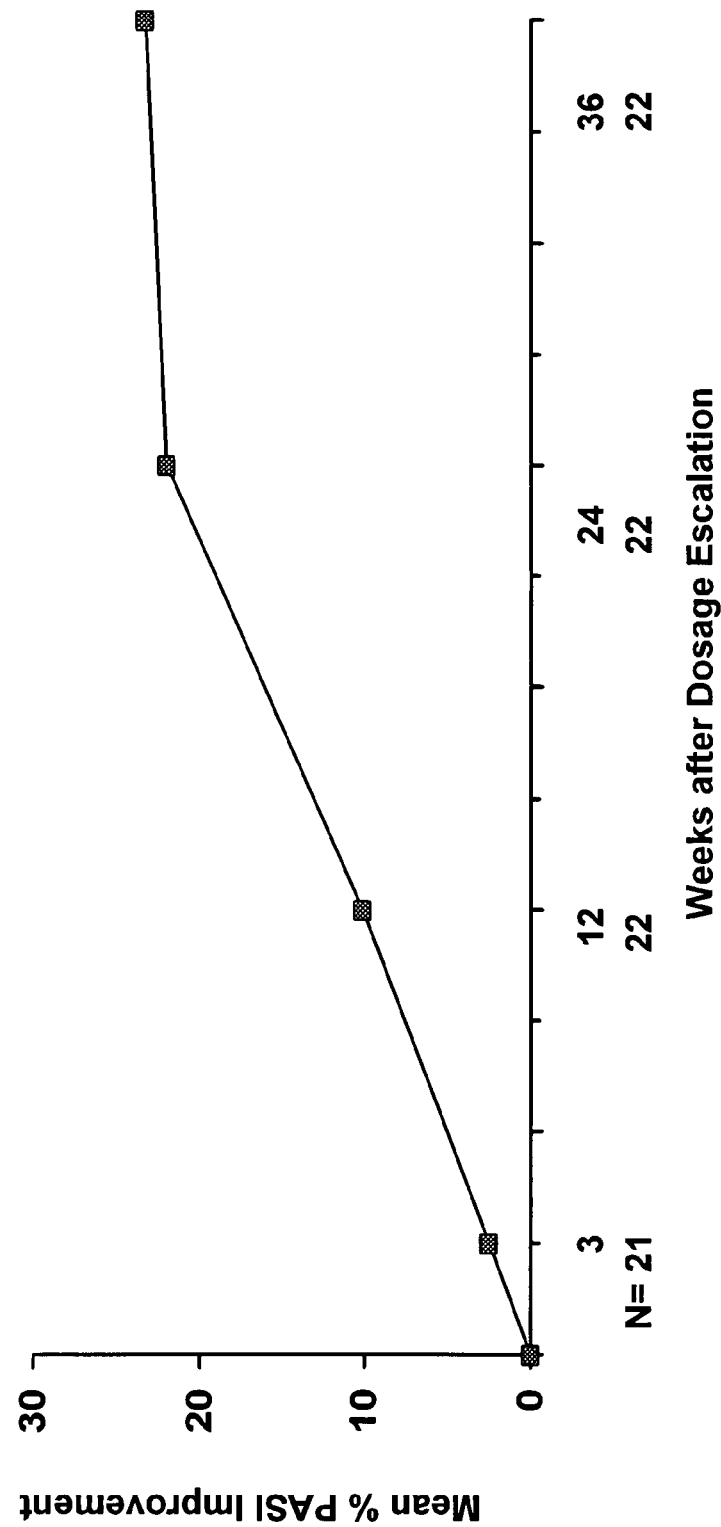
FIG. 4 shows the mean percentage PASI improvement in patients whose dosages were increased, up to 36 weeks after dosage escalation. Mean % improvement in PASI by last observation was carried forward.

FIG. 4 is a graphical representation of the PASI improvement in patients whose dosages were increased. As can be seen in this figure, the mean percentage PASI improvement was 23% at 36 weeks after dosage escalation.

The PASI and PGA "Clear"/"Almost Clear" response rates at selected time points after dosage escalation are shown below in Table 25.

TABLE 25

|  | Week 12 (n = 20) | Week 24 (n = 16) | Week 36 (n = 7) |
|---|---|---|---|
| PASI 50 (%) | 60 | 69 | 71 |
| PASI 75 (%) | 35 | 69 | 71 |
| PASI 90 (%) | 25 | 38 | 71 |
| PASI 100 (%) | 10 | 19 | 43 |
| PGA "Clear"/"Almost Clear" (%) | 32 | 45 | 45 |

Observed values. Weeks 12, 24, and 36 are relative to start of dosage escalation.
N = 22 for percentages of patients with PGA "Clear"/"Almost Clear" at weeks 12-36.

Of the total 382 patients, 53 (14%) started adalimumab 40 mg weekly in the OLES. Among them, 45% were concomitantly taking methotrexate, compared to 50% in patients not undergoing dose escalation. Skin and joint outcomes observed prior to and 12 wks after dose escalation are shown below (Table 26):

TABLE 26

|  | Prior to dose escalation | 12 wks after dose escalation |
|---|---|---|
| ACR 20/50/70 (% responders) | 11/2/0 | 41/22/11 |
| PASI 50/75/90 (% responders) | 55/18/14 | 60/35/25 |
| PGA Clear/Almost Clear (%) | 10 | 32 |

Joint and skin improvements were sustained up to 36 wks after dose escalation.

Four patients experienced a serious adverse event (AE), including 1 serious infectious AE, after dose escalation. One patient discontinued from the study due to an AE. The four serious adverse events experienced by patients undergoing dosage escalation included: diverticulitis, appendicitis, salmonella infection, and pancreatitis. These serious adverse events were considered by the investigators to be probably unrelated to the adalimumab treatment. Table 27 shows the common adverse events that occurred =5% in those patients whose dosages were increased.

TABLE 27

|  | On or after increase in adalimumab dosage from eow to weekly<br>N = 53<br>N (%) |
|---|---|
| Any AE (adverse event) | 31 (58.5) |
| Any SAE (serious adverse event) | 4 (7.5) |
| Upper Respiratory Tract Infection NOS | 1 (1.9) |
| Nasopharyngitis | 1 (1.9) |
| Headache NOS | 2 (3.8) |
| Cough | 0 (0.0) |
| Injection site reaction NOS | 0 (0.0) |
| Liver Function Test NOS abnormal | 1 (1.9) |
| Psoriatic arthropathy aggravated | 2 (3.8) |
| Contusion | 1 (1.9) |
| Pharyngolaryngeal Pain | 1 (1.9) |

*NOS = not otherwise specified

In sum, approximately 85% of PsA patients treated with adalimumab eow had a sufficiently satisfactory clinical response and did not require dose escalation. In patients whose dosages were increased from adalimumab eow to weekly, adalimumab was efficacious against skin and joint disease. Adalimumab was also well tolerated in the subpopulation of patients whose dosages were escalated.

Example 9

Adalimumab is Efficacious in Treating the Skin Disease of Patients with PsA Who have Mild to Severe Baseline Skin Involvement: Subanalysis by Severity of Psoriasis The purpose of this study was to examine skin outcomes in patient subgroups with mild to moderate and moderate to severe psoriasis at baseline. Study G was a double-blind, placebo-controlled Phase III study of adalimumab in patients with active PsA (≥3 swollen and ≥tender joints) as described above. Patients were stratified by methotrexate use (yes/no) and degree of psoriasis (<3% and ≥3% BSA involvement (skin evaluable)) and randomized to adalimumab 40 mg eow or placebo for 24 weeks. PASI and PGA were measured for patients with ≥3% BSA. Patients were subgrouped by baseline PGA (a static composite of plaque evaluation, scaling and erythema) as mild to moderate or moderate to severe. Skin efficacy outcomes were analyzed post-hoc on an ITT, NRI basis for each subgroup.

Efficacy measures included: ACR response criteria (co-primary endpoint: ACR20 response at Week 12); PASI in patients with significant psoriasis at study entry (≥3% BSA); and PGA of psoriasis. The post-hoc subanalysis examined patients according to the severity of psoriasis at baseline: PGA of mild to moderate vs. PGA of moderate to severe. Weekly adalimumab dosing was allowed on or after Week 36 in patients with <20% improvement in tender joint count and swollen joint count.

313 patients (151 adalimumab, 162 placebo) enrolled in Study G, with similar baseline data between groups. As described in Table 1 above, baseline demographics and disease characteristics were comparable in patients with mild to moderate and with moderate to severe psoriasis at baseline with the exception of the percentages of male patients (47% placebo-treated and 53% adalimumab-treated male patients in the mild to moderate psoriasis subgroup, and 62% placebo-treated and 63% adalimumab-treated male patients in the moderate to severe psoriasis subgroup).

PASI was evaluated for 138 patients (69 adalimumab, 69 placebo). As can be seen in Table 28, baseline PASI and DLQI scores were comparable among the placebo and adalimumab-treated subgroups of patients.

TABLE 28

|  | Placebo | | Adalimumab 40 mg eow | |
|---|---|---|---|---|
| Characteristics | Mild to Moderate Psoriasis | Moderate to Severe Psoriasis | Mild to Moderate Psoriasis | Moderate to Severe Psoriasis |
| Mean PASI ± SD (0-72) | n = 30<br>4.0 ± 2.4 | n = 39<br>11.6 ± 8.0 | n = 30<br>4.4 ± 2.8 | n = 39<br>9.8 ± 6.8 |
| Mean DLQI ± SD | n = 30<br>9.9 ± 7.9 | n = 38<br>10.5 ± 7.3 | n = 29<br>5.6 ± 4.3 | n = 37<br>11.0 ± 7.1 |

Overall, ACR20/50/70 and PASI 50/75/90 responses at Week 24 were 57/39/23 and 75/59/42 for adalimumab versus 15/6/1 and 12/1/0 for placebo. The overall PASI 50/75/90/100 responses at Week 24 were 75/59/42/29 adalimumab (n=69) and 12/1/0/0 placebo (n=69).

Table 29 shows the PASI responses at Weeks 12 and 24 by disease severity, including mild to moderate and moderate to severe. At Week 24, PASI 50/75/90/100 in mild to moderate psoriasis patients were 77/60/40/33 (adalimumab) and 7/0/0/0 (placebo) (p<0.001); in moderate to severe psoriasis patients, PASI 50/75/90 were 74/59/44 (adalimumab) and 15/3/0 (placebo) (p<0.001).

TABLE 29

PASI Responses at Weeks 12 and Weeks 24 by Disease Severity

|  | Week 12 | | Week 24 | |
|---|---|---|---|---|
|  | Mild-moderate (n = 30) | Moderate-severe (n = 39) | Mild-moderate (n = 30) | Moderate-severe (n = 39) |
| PASI 50 (%) | 77* | 69* | 77* | 74* |
| PASI 75 (%) | 50* | 49* | 60* | 59* |

TABLE 29-continued

PASI Responses at Weeks 12 and Weeks 24 by Disease Severity

|  | Week 12 | | Week 24 | |
| --- | --- | --- | --- | --- |
|  | Mild-moderate (n = 30) | Moderate-severe (n = 39) | Mild-moderate (n = 30) | Moderate-severe (n = 39) |
| PASI 90 (%) | 27 | 33* | 40* | 44* |
| PASI 100 (%) | 13 | 8 | 33* | 26* |

*p ≤ 0.001,
†p = 0.005 vs. placebo (placebo data not shown) Non-responder imputation.

Overall PASI responses, and responses for each subgroup at week 24, are shown below in Table 30:

TABLE 30

Overall PASI responses and PASI responses by PGA score at Week 24

|  | Overall | | Mild-moderate by baseline PGA | | Moderate-severe by baseline PGA | |
| --- | --- | --- | --- | --- | --- | --- |
|  | Adalimumab (n = 69) | Placebo (n = 69) | Adalimumab (n = 39) | Placebo (n = 39) | Adalimumab (n = 30) | Placebo (n = 30) |
| PASI 50 (%) | 75* | 12 | 77* | 7 | 74* | 15 |
| PASI 75 (%) | 59* | 1 | 60* | 0 | 59* | 3 |
| PASI 90 (%) | 42* | 0 | 40 | 0 | 44* | 0 |

*P < 0.001 adalimumab vs. placebo

In each disease severity group, at Week 24, a PGA score of "Clear" or "Almost Clear" was significantly more frequent with adalimumab-treated than placebo-treated patients. The percentage of patients with PGA "Clear" or "Almost Clear" at Week 24 included 23% placebo (n=30) vs. 73%*adalimumab (n=30) for mild to moderate subgroup and 0% placebo (n=33) vs. 55%*adalimumab (n=40) for moderate to severe (*p<0.001 vs. placebo, non-responder imputation).

At Week 24, patients treated with adalimumab also achieved an improvement in their quality of life, as measured by DLQI. The mean change in DLQI from baseline to Week 24 in patients in the Mild to Moderate subgroup was −0.4 placebo (n=30) vs. −3.2 adalimumab (n=29), and for the Moderate to Severe subgroup the mean change was −1.0 placebo (n=36) vs. −8.2*adalimumab (n=37) (*p<0.001 vs. placebo, LOCF). Furthermore, at week 24, in each disease severity group, there were substantial percentages of adalimumab-treated patients who achieved a DLQI of 0. The percentage of patients with a DLQI equal to 0 at Week 24 for the mild to moderate subpopulation was 7% placebo (n=30) vs. 40% adalimumab (n=30) and for the moderate to severe subpopulation 3% placebo (n=37) vs. 40% adalimumab (n=40).

Rates of individual adverse events and serious adverse events were comparable between adalimumab and placebo. Table 31 shows the common adverse events that occurred =5% at Week 24.

TABLE 31

Common Adverse Events

|  | Placebo eow N = 162 N (%) | Adalimumab 40 mg eow N = 151 N (%) |
| --- | --- | --- |
| Any AE (adverse event) | 130 (8.20) | 122 (80.8) |
| Any SAE (serious adverse event) | 7 (4.3) | 5 (3.3) |
| Upper Respiratory Tract Infection NOS | 24 (14.8) | 19 (12.6) |
| Nasopharyngitis | 15 (9.3) | 15 (9.9) |
| Headache NOS | 14 (8.6) | 9 (6.0) |
| Injection site reaction NOS | 5 (3.2) | 10 (6.6) |
| Hypertension NOS | 5 (3.1) | 8 (5.3) |
| PsA aggravated | 11 (6.8) | 5 (3.3) |

TABLE 31-continued

Common Adverse Events

|  | Placebo eow N = 162 N (%) | Adalimumab 40 mg eow N = 151 N (%) |
| --- | --- | --- |
| Psoriasis aggravated | 10 (6.2) | 3 (2.0) |
| Arthralgia | 9 (5.6) | 3 (2.0) |
| Diarrhea NOS | 9 (5.6) | 3 (2.0) |

*NOS = not otherwise specified

In sum, adalimumab was efficacious against PsA skin disease and improved dermatology-specific quality of life in patients whose psoriasis at baseline, as measured by PGA, ranged from mild to moderate, or moderate to severe. Furthermore, adalimumab had an acceptable safety profile and was well-tolerated during 24 weeks of treatment in Study G.

Example 10

PASI 100 is Associated with Better Dermatology-Specific Patient Reported Outcomes Compared with PASI 75-99 in Adalimumab-Treated Patients with Psoriatic Arthritis Subanalysis of PsA Study G The following describes a sub-analysis of Study G, which was the largest randomized, double-blind, placebo-controlled trial to date of a TNF antagonist in psoriatic arthritis (PsA). Patients who participated in the study predominantly had long-standing, polyarticular disease, and approximately half used methotrexate (MTX) during the trial. The overall conclusion of the study was that 24 weeks of treatment with adalimumab provided significant improvements in skin disease, arthritis, and quality of life for patients with moderate to severe PsA who had failed NSAID therapy The object of the following study was to determine whether patients who achieved a PASI 100 response in Study G, a Phase III study of adalimumab in patients with psoriatic arthritis (PsA), had superior dermatology-specific patient reported outcomes compared with patients who achieved PASI 75-99 responses For the present analysis, DLQI scores were compared among patients classified post hoc by their level of skin response at Week 24 (PASI<50, 50-74, 75-99, or 100). Analyses were restricted to observed data from patients with =3% BSA involvement at baseline. Efficacy outcome measures for the present analyses included: Psoriasis Area and Severity index (PASI); Dermatology Life Quality Index (DLQI)—lower score indicates better health status; and American College of Rheumatology response rate (for arthritis).

DLQI scores were determined for patients grouped post-hoc by the category of level PASI response from baseline to Week 24: PASI<50; PASI 50-74; PASI 75-99; and PASI 100. Analyses were restricted to observed data from patients with =3% BSA involvement at baseline, and DLQI and PASI scores recorded at baseline and Week 24

A total of 313 patients received treatment with adalimumab or placebo in Study G (Tables 1 and 32). In the placebo arm and the adalimumab arm, 59 patients each had >3% BSA involvement with psoriasis, completed 24 weeks of blinded therapy, and had PASI and DLQI scores available from baseline and Week 24 (Table 33). Baseline demographics and disease characteristics were comparable for these 59 placebo and 59 adalimumab patients.

TABLE 32

Baseline Demographics and Disease Severity Characteristics

| Characteristics* | Placebo (N = 162) | Adalimumab 40 mg eow (N = 151) |
|---|---|---|
| Age, years | 49.2 ± 11.1 | 48.6 ± 12.5 |
| Males, % | 55 | 56 |
| Caucasian, % | 94 | 97 |
| Body weight, kg | 85.5 ± 16.5 | 86.0 ± 20.6 |
| Psoriasis duration, years | 17.1 ± 12.6 | 17.2 ± 12.0 |
| Psoriatic arthritis duration, years | 9.2 ± 8.7 | 9.8 ± 8.3 |
| Rheumatoid factor negative, % | 90 | 89 |
| Patients taking MTX at baseline†, % | 50 | 51 |
| BSA ≥ 3% skin involvement, n | 70 | 70 |
| PASI score‡§ | 8.3 ± 7.2 | 7.4 ± 6.0 |
| DLQI‡∥ | 10.3 ± 7.5 | 8.6 ± 7.4 |

*Mean values ± SD, except for percentages or BSA ≥3% skin involvement;
†Mean MTX dosage of 17.1 mg/wk;
‡Patients with ≥3% BSA skin involvement;
§n = 69 for both placebo and adalimumab groups;
∥n = 68 for placebo, n = 66 for adalimumab

TABLE 33

Baseline Characteristics by PASI Response in Adalimumab-Treated Patients

| Characteristics* | PASI < 50 (N = 10) | PASI 50-74 (N = 8) | PASI 75-99 (N = 22) | PASI 100 (N = 19) |
|---|---|---|---|---|
| Age, years | 51.2 ± 12.0 | 49.0 ± 14.2 | 48.7 ± 16.6 | 49.3 ± 13.4 |
| Males, % | 60 | 38 | 59 | 58 |
| Caucasian, % | 100 | 100 | 96 | 95 |
| Body weight, kg | 88.7 ± 21.5 | 96.8 ± 36.6 | 93.6 ± 23.3 | 81.9 ± 17.4 |
| Psoriasis duration, years | 21.0 ± 16.4 | 21.9 ± 13.6 | 14.0 ± 8.2 | 17.9 ± 13.2 |
| Psoriatic arthritis duration, years | 10.8 ± 11.3 | 10.2 ± 11.5 | 8.5 ± 6.8 | 11.3 ± 9.4 |
| Rheumatoid factor negative, % | 90 | 88 | 86 | 95 |
| Patients taking MTX at baseline†, % | 30 | 25 | 55 | 47 |
| PASI score | 6.1 ± 5.7 | 10.0 ± 6.5 | 7.3 ± 4.5 | 6.2 ± 3.4 |
| DLQI | 9.4 ± 4.7 | 10.5 ± 7.9 | 9.5 ± 6.7 | 6.8 ± 6.7 |
| Any previous DMARD use, % | 80 | 63 | 96 | 84 |
| Swollen joint count | 19.9 ± 13.8 | 14.6 ± 11.0 | 15.0 ± 14.3 | 10.9 ± 8.9 |
| Tender joint count | 28.2 ± 19.7 | 22.5 ± 12.4 | 26.2 ± 22.7 | 18.5 ± 17.0 |
| CRP (mg/L) | 1.4 ± 1.4 | 1.5 ± 1.4 | 1.8 ± 3.4 | 1.3 ± 1.5 |
| HAQ DI | 1.3 ± 0.7 | 1.0 ± 0.7 | 1.3 ± 0.6 | 0.8 ± 0.7 |

Patients with >3% BSA involvement with psoriasis who completed 24 weeks of blinded therapy and had PASI and DLQI scores available from baseline and Week 24.
*Mean values ± SD, except for percentages;
†Mean MTX dosage of 17.1 mg/wk for all patients.

At Week 24, PASI 75 responses were observed in 69% of patients treated with adalimumab (including 32% PASI 100) compared with 2% with placebo (Table 34).

TABLE 34

PASI Response Rates at Week 24

|  | Adalimumab (n = 59) | Placebo (n = 59) |
| --- | --- | --- |
| PASI < 50 (%) | 17 | 85 |
| PASI 50-74 (%) | 14 | 14 |
| PASI 75-99 (%) | 37 | 2 |
| PASI 100 (%) | 32 | 0 |

Restricted to patients in Study G who had PASI and DLQI data at baseline and Week 24. Observed values.

Arthritis improvement was greatest in patients with PASI 100 responses at Week 24 (Table 35).

TABLE 35

ACR Response Rates for Adalimumab-Treated Patients by Level of PASI Response at Week 24

|  | ACR20 | ACR50 | ACR70 |
| --- | --- | --- | --- |
| PASI < 50 (%) (n = 10) | 50 | 20 | 10 |
| PASI 50-74 (%) (n = 8) | 50 | 13 | 0 |
| PASI 75-99 (%) (n = 22) | 50 | 41 | 32 |
| PASI 100 (%) (n = 19) | 74 | 58 | 37 |

Restricted to patients in Study G who had PASI and DLQI data at baseline and Week 24. Observed values.

At Week 24, the mean HAQ DI score was lowest in adalimumab-treated patients with PASI 100 responses (Table 36).

TABLE 36

Mean HAQ DI Scores for Adalimumab-treated Patients by PASI Response Rates at Week 24

|  | Mean HAQ DI Scores | Mean HAQ DI at Baseline | Mean Change in HAQ DI at Week 24* |
| --- | --- | --- | --- |
| PASI < 50 (%) (n = 10) | 0.8 | 1.3 | −0.5 |
| PASI 50-74 (%) (n = 8) | 0.6 | 1.0 | −0.4 |
| PASI 75-99 (%) (n = 22) | 0.7 | 1.3 | −0.6 |
| PASI 100 (%) (n = 19) | 0.3 | 0.8 | −0.4 |

Observed values.

*Minimum Clinically Important Difference = −0.30 for PSA (Mease, PJ, et al. Ann Rheum Dis. 2004; 63: Suppl 1: 391-2); and −0.22 for rheumatoid arthritis (Goldsmith C., et al., J Rheumatol. 1993; 20: 561-5).

At Week 24, the mean DLQI scores were lowest and the most improved in adalimumab-treated patients with PASI 75-99 and PASI 100 responses (Table 37)

TABLE 37

Mean DLQI Scores for Adalimumab-treated Patients by PASI Response Rates at Week 24

|  | Mean DLQI Scores | Mean DLQI at Baseline | Mean Change in DLQI at Week 24* |
| --- | --- | --- | --- |
| PASI < 50 (%) (n = 10) | 5.6 | 9.4 | −3.8 |
| PASI 50-74 (%) (n = 8) | 7.1 | 10.5 | −3.4 |
| PASI 75-99 (%) (n = 22) | 1.3 | 9.5 | −8.2 |
| PASI 100 (%) (n = 19) | 0.2 | 6.8 | −6.6 |

*Minimum Important Difference = −5.0; Shikar R., et al., Health Qual Life Outcomes. 2006; 4: 71. Observed values.

At Week 24, a DLQI score of zero or 1 was achieved by 95% of patients with PASI 100 response, compared with 68% of PASI 75-99 responders (Table 38).

TABLE 38

DLQI Scores for Adalimumab-treated Patients by PASI Response Rates at Week 24

|  | DLQI = 0 | DLQI = 1 | DLQI = 2 | DLQI = 3 |
| --- | --- | --- | --- | --- |
| PASI < 50 (%) (n = 10) | 18 | 0 | 0 | 82 |
| PASI 50-74 (%) (n = 8) | 30 | 10 | 30 | 30 |
| PASI 75-99 (%) (n = 22) | 36 | 32 | 14 | 18 |
| PASI 100 (%) (n = 19) | 75 | 20 | 0 | 5 |

At Week 24, the DLQI score was >1 in only 5% of patients with a PASI 100 response, compared with 32%, 60%, and 82% of patients with PASI 75-99, 50-74, and <50 responses (Table 38). Table 39 shows the DLQI questions that accounted for a score >0 in Adalimumab treated patients at week 24.

TABLE 39

DLQI Questions Accounting for Score > 0 in Adalimumab-Treated Patients at Week 24

| DLQI Question Topic | PASI 100 Responders with DLQI Score of >0, n (%) | PASI 75-99 Responders with DLQI Score of >0, n (%) |
|---|---|---|
| 1. Skin itchy, sore, painful, or stinging? | 4 (21) | 10 (46) |
| 2. Degree to which embarrassed or self-conscious because of skin? | 0 | 2 (9) |
| 3. Degree to which skin interfered with daily activities, e.g., shopping or looking after your home or garden. | 0 | 1 (4) |
| 4. Degree to which skin influenced the clothing choice? | 0 | 2 (9) |
| 5. Degree to which skin affected social or leisure activities? | 0 | 2 (9) |
| 6. Degree to which skin made playing sports difficult? | 0 | 2 (9) |
| 7. Degree to which skin is a problem at work or studying? | 0 | 2 (9) |
| 8. Degree to which skin brings problems with partner or close friends or relatives? | 0 | 1 (4) |
| 9. Degree to which skin caused any sexual difficulties? | 0 | 0 |
| 10. Degree to which treatment for skin has been problem, e.g., making home messy, or by taking up time? | 0 | 4 (18) |

In sum, the results showed that at Week 24, PASI 75-99/100 response rates were 2%/0% for the placebo group and 34%/31% for the adalimumab group. Adalimumab-treated patients with PASI<50 (n=11), 50-74 (n=10), 75-99 (n=22), or 100 (n=20) had mean DLQI scores (lower score indicates better health status) of 5.9, 5.8, 1.3, and 0.4, respectively; among those with baseline and Week 24 DLQI scores, mean reductions in DLQI from baseline were 3.8, 3.4, 8.2, and 6.6, respectively (MID [minimum important difference] for DLQI estimated at 5.0). At Week 24, 18%/30%/36%/75% of patients with PASI<50/50-74/75-99/100 had a DLQI score of 0, respectively; 0%/10%/32%/20% had a DLQI score of 1, respectively; 0%/30%/14%/0% had a DLQI score of 2, respectively; and 82%/30%/18%/5% had a DLQI score of =3, respectively.

In conclusion, adalimumab treatment of patients with PsA provided sustained and clinically meaningful improvement. Results from this post-hoc subanalysis suggest that achievement of PASI 100 represents a clinically meaningful incremental benefit above the achievement of PASI 75-99. In post-hoc analyses of Study G, outcomes of arthritis, physical function, and dermatology-related quality of life were better at Week 24 in patients with PASI 100 responses compared with PASI 75-99 responders. At Week 24, a DLQI score of zero or 1 was achieved by 95% of patients with PASI 100 response, compared with 68% of PASI 75-99 responders. A DLQI>1 was rare in patients with a PASI 100 response (5%).

Example 11

Safety and Efficacy of Adalimumab in the Treatment of Patients with Psoriatic Arthritis Who Had Failed Disease-Modifying Antirheumatic Drug Therapy The object of the following study was to demonstrate the safety and efficacy of adalimumab for the treatment of moderately to severely active psoriatic arthritis (PsA) in a subpopulation of patients with an inadequate response to disease-modifying antirheumatic drugs (DMARDs).

Study Design

A double-blind, Phase III, randomized placebo-controlled, multicenter study was conducted to demonstrate the safety and efficacy of adalimumab in the treatment of moderately to severely active PsA in patients who had had an inadequate response to DMARD therapy. Following a screening period of up to 14 days, patients were stratified by DMARD use at baseline (yes/no), and then randomized in a 1:1 ratio to receive a subcutaneous injection of adalimumab 40 mg every other week (eow) or placebo for 12 weeks. Patients were randomized in blocks of 4 using an interactive voice response system. Patients who completed the blinded phase could elect to receive open-label therapy with adalimumab 40 mg eow, the first 12 weeks of which are reported here. Study drug was provided in pre-filled syringes containing a 0.8-ml solution of adalimumab (50 mg/ml) or matching placebo (Abbott Laboratories, Abbott Park, Ill.). Study visits occurred at baseline and Weeks 2, 4, 8, 12, 14, 18, and 24 for safety and efficacy assessments.

The primary efficacy measure was a 20% improvement in American College of Rheumatology (ACR20) core criteria at Week 12. Secondary efficacy measures included the modified Psoriatic Arthritis Response Criteria (PsARC) and assessments of disability, psoriatic lesions, and quality of life. For missing data, nonresponder imputation was used for ACR and PsARC scores and last observation carried forward for other measures.

The study was conducted at 16 sites in Canada and the United States. The protocol was approved at each site by an independent ethics committee or institutional review board and was conducted in accordance with the International Conference on Harmonization Good Clinical Practice standards; Food and Drug Administration regulations governing clinical study conduct; ethical principles originating from the Declaration of Helsinki (1989 revision); and all applicable local laws and customs. All participants provided written informed consent after the nature and purpose of the study had been explained and before any study procedure was initiated.

Patients

Eligible patients were male or female, at least 18 years of age, and in generally good health based on medical history, physical examination, laboratory profile, chest radiograph, and a 12-lead electrocardiogram. At study entry, patients were required to have had =3 swollen joints and =3 tender or painful joints, and either an active cutaneous lesion of chronic plaque psoriasis or a documented history of chronic plaque psoriasis diagnosed by the investigator or a dermatologist. All patients enrolled in the study were receiving concomitant DMARD therapy or had a history of DMARD therapy with an inadequate response, as defined by the investigator. Oral corticosteroids were allowed during the trial if the dosage did not exceed the equivalent of prednisone 10 mg/day and had been stable during the 4 weeks preceding the baseline visit. Concomitant treatment with MTX or other DMARDs, with the exception of cyclosporine and tacrolimus (oral or topical) received within 4 weeks of the baseline visit, was allowed if the patient had received a minimum of 3 months of therapy and the dosage had been stable during the 4 weeks preceding the baseline visit. The maximum allowable MTX dosage was 30 mg/week. A purified protein derivative skin test was required for all participants. For patients with evidence of a previous tuberculosis infection, a documented history of treatment for latent tuberculosis was required, or such treatment had to have been initiated before the first dose of study drug.

Patients were excluded if they had a history of: previous anti-TNF therapy; intravenous infusions or intra-articular injections of corticosteroids within 4 weeks of baseline; topical psoriasis therapies (e.g., keratolytics, coal tar, anthralin) within 2 weeks of baseline (although medicated shampoos and low-potency topical steroid use on the palms, soles of the feet, axilla, and groin area were allowed); ultraviolet A (UVA) phototherapy, including psoralen and UVA, or use of a tanning booth within 2 weeks of the baseline visit; or oral retinoids within 4 weeks of the baseline visit; alefacept or siplizumab within 12 weeks, or any other biologic or investigational therapy within 6 weeks of the baseline visit. They were also excluded based on current use or likely need for antiretroviral therapy.

Patients with persistent or severe infections or a history of active tuberculosis, or who had an active nonpsoriatic skin disease that could interfere with the assessment of target lesions were also excluded. Additional exclusion criteria were a significant history of cardiac, renal, neurologic, psychiatric, endocrinologic, metabolic, or hepatic disease; neurologic symptoms suggestive of central nervous systemic demyelinating disease; and a history of malignancy other than carcinoma in situ of the cervix or adequately treated non-metastasic squamous or basal cell skin carcinoma.

Measures of Efficacy and Safety

The primary efficacy variable was the ACR20 response rate at Week 12 (Felson et al. *Arthritis Rheum* 1995; 38:727-35). The total number of assessed joints was 78 for the tender joint count (TJC) and 76 for the swollen joint count (SJC) (Mease P J, et al. *Arthritis Rheum* 2005; 52:3279-89). Joints or regions examined were those routinely examined in RA plus the first carpal metacarpal phalangeal joints (n=2) and the distal interphalangeal joints of the toes (n=8). Hips were excluded from the SJC. Patients were evaluated for dactylitis of the hands and feet (total score 0-60, with each digit rated 0 [absent] to 3 [severe]), and enthesitis of the proximal insertion of the Achilles tendon and plantar fascia (total score 0-4, with each insertion rated 0 [enthesitis absent] or 1 [enthesitis present]). Other efficacy measures included patient's assessment of pain during the previous week, patient's global assessment of disease activity during the previous 24 hours, and physician's global assessment of disease activity (current PsA activity), each using a visual analog scale (VAS) of 0-100 mm (Felson et al., supra). Secondary efficacy measures of arthritis and QOL included the ACR50 and ACR70 response rates, the modified Psoriatic Arthritis Response Criteria (PsARC) (Clegg D O, et al. *Arthritis Rheum* 1996; 39:2013-20; Mease P J, et al. *Arthritis Rheum* 2004; 50:2264-72); the disability index of the Health Assessment Questionnaire (HAQ DI) score (Fries J F, et al, *J Rheumatol* 1982; 9:789-93); the Short Form 36 Health Survey (SF-36) and its Physical and Mental Component Summary (PCS and MCS) scores (Fries et al, supra); and the 13-item fatigue scale of the Functional assessment of Chronic Illness Therapy (FACIT-F) measure (Cella D, et al., *Oncology* 1997; 11:232-5). Psoriasis-related assessments were the target lesion assessment, the physician's global assessment for psoriasis and the Dermatology Life Quality Index (DLQI) (Finlay A Y, et al., *Clinical Exp Dermatol* 1994:19:210-6). The Target Lesion assessment evaluated target lesions for erythema, induration and scaling, each on a scale of 0 (best) to 5 (worst), with a total plaque score of 0-15. Psoriasis-related assessments were conducted only for patients with a lesion that, at baseline, was =2 cm in diameter and had a plaque score =6.

Post-hoc analyses of ACR response rates at Week 12 were performed for treatment group subsets defined according to the following parameters: MTX use at baseline (yes/no), DMARD use at baseline (yes/no), non-steroidal anti-inflammatory drug use at baseline (yes/no), corticosteroid use at baseline (yes/no), baseline RF-positive or negative, baseline C-reactive protein concentration (CRP)≥1 mg/L or <1, and male or female.

The safety of adalimumab was assessed by measuring vital signs at every study visit, performing routine hematologic and clinical chemistry blood tests and urinalyses throughout the study, and recording adverse events throughout the study. Serological tests for rheumatoid factor and antinuclear antibodies were performed only at baseline visits.

Statistical Analyses

To provide =90% power to detect a difference in responses at a =0.05 for a projected Week 12 ACR20 rate of 60% for the adalimumab group and 25% for the placebo group, =50 patients per group were needed. For efficacy and safety analyses, the intention-to-treat population was defined as all patients who received at least 1 dose of study medication. After Week 12, the ITT population for the placebo arm was defined as those patients who received at least one dose of open-label adalimumab. All statistical tests were 2-sided, and comparisons were performed with a =0.05 unless stated otherwise.

The percentages of patients who achieved an ACR20 in each group at Week 12 were compared by using the Cochran-Mantel-Haenszel test, with baseline DMARD use as the stratification factor. ACR20 response rates at time points other than Week 12 and ACR50 and ACR70 rates at all time points were analyzed using Fisher's Exact test and combining baseline DMARD-use categories. PsARC responses and comparisons of the numbers of patients in the physician's global assessment of psoriasis disease activity categories "Clear" and "Minimal" with the numbers in other categories were analyzed using the Cochran-Mantel-Haenszel test, with baseline DMARD use as the stratification factor. The mean changes from baseline in the HAQ DI, Target Lesion response, DLQI, FACIT-F and SF-36 scores, as well as patient's assessment of pain, patient's global assessment of disease activity, and physician's global assessment of disease activity, were compared (adalimumab vs. placebo) using a two-way analysis of variance model that included factors for baseline DMARD use and treatment.

For missing data, nonresponder imputation (i.e., missing responses were counted in the nonresponder category) was used for analysis of ACR and PsARC responses, and last observation carried forward was used for all other efficacy measures. Statistical significance was not determined for comparisons involving results after Week 12.

Adverse events (AEs) were summarized by incidence and severity. The Fisher's exact test was used to compare the incidences of reported AEs in each group.

Results 102 patients were enrolled in the study, 100 of whom received study drug (51 adalimumab, 49 placebo). Two patients randomized to placebo never received study drug: one because of withdrawn consent, and the other because evidence from the initial evaluation indicated that the patient was not in generally good health. Overall, 96 patients (50 adalimumab, 46 placebo) completed the 12-week, double-blind, placebo-controlled portion of the study. The one patient from the adalimumab arm who did not complete the blinded period was allowed to enter the open-label extension. Of the 97 patients enrolled in the extension study, 92 completed 12 weeks of open-label adalimumab treatment. Three patients withdrew due to an adverse event, and two patients withdrew for other reasons. Overall, the baseline demographics, medication usage, and disease severity characteristics were similar between treatment groups. The mean CCRP concentration and the percentage of patients with a negative rheumatoid factor (RF) test were statistically significantly greater in the placebo group (Table 41). At baseline, 62 patients (32 adalimumab, 30 placebo) had evaluable target lesions and were therefore eligible for psoriasis evaluations (Table 41).

Efficacy: Efficacy at Week 12

ACR Response Rates and Core ACR Assessments.

At Week 12, 39% of adalimumab patients achieved an ACR20 response, compared with 16% of placebo patients (Δ=23% [95% CI, 5%-41%], p=0.012). Statistically significantly more adalimumab than placebo patients also achieved ACR50 (25% vs. 4%, p=0.001) and ACR70 (14% vs. 1%, p=0.013) responses at Week 12 (Table 40).

TABLE 40

|  | Week 12 | | Week 24 | |
| --- | --- | --- | --- | --- |
|  | Placebo (n = 49) | Adalimumab (n = 51) | Placebo/adalimumab (n = 46) | Adalimumab (n = 51) |
| ACR20 | 16 | 39* | 57 | 65 |
| ACR50 | 2 | 25† | 37 | 43 |
| ACR70 | 0 | 14* | 22 | 27 |

Reductions in the ACR components of pain, patient's and physician's global assessments of disease activity, and physical function (HAQ DI) were all statistically significantly greater at Week 12 for adalimumab vs. placebo patients (Table 41). Table 41 shows that baseline disease characteristics were similar between both groups except for a higher CRP value in the placebo arm.

TABLE 41

| Baseline demographic and clinical characteristics | | |
| --- | --- | --- |
| Characteristic | Placebo (n = 49) | Adalimumab 40 mg eow (n = 51) |
| Age (years) | 47.7 ± 11.3 | 50.4 ± 11.0 |
| Male, n (%) | 25 (51.0) | 29 (56.9) |
| White, n (%) | 46 (93.9) | 50 (98.0) |
| Weight (kg) | 88.5 (21.1) | 91.5 (22.5) |
| Rheumatoid factor negative* | 48 (98.0) | 41 (80.4) |
| Duration of psoriasis (years) | 13.8 ± 10.7 | 18.0 ± 13.2 |
| Duration of psoriatic arthritis (years) | 7.2 ± 7.0 | 7.5 ± 7.0 |
| Moll and Wright subtype, n (%) | | |
| Symmetric polyarthritis | 41 (83.7) | 42 (82.4) |
| Asymmetric oligoarthritis | 7 (14.3) | 5 (9.8) |
| Distal interphalangeal arthropathy | 0 | 3 (5.9) |
| Spondylitis | 1 (2.0) | 1 (2.0) |
| Arthritis mutilans | 0 | 0 |
| Dactylitis (overall severity) | 2.5 ± 4.3 | 2.9 ± 5.1 |
| Enthesitis (total sites) | 1.0 ± 1.3 | 0.9 ± 1.2 |
| Medications | | |
| Use of previous DMARDs, n (%) | 49 (100) | 51 (100) |
| Use of DMARDs at baseline, n (%) | 33 (67.3) | 33 (64.7) |
| Mean number of previous DMARDs, n | 2.1 ± 1.3 | 1.7 ± 0.9 |
| Use of previous methotrexate, n (%) | 39 (79.6) | 41 (80.4) |
| Use of methotrexate at baseline, n (%) | 23 (46.9) | 24 (47.1) |
| Use of previous NSAIDs, n (%) | 48 (98.0) | 46 (90.2) |
| Use of NSAIDs at baseline, n (%) | 42 (85.7) | 37 (72.6) |
| Use of previous oral corticosteroids, n (%) | 15 (30.6) | 10 (19.6) |
| Use of oral corticosteroids at baseline, n (%) | 9 (18.4) | 4 (7.8) |
| Core ACR Assessments | | |
| Swollen joint count (0-76) | 18.4 ± 12.1 | 18.2 ± 10.9 |
| Tender joint count (0-78) | 29.3 ± 18.1 | 25.3 ± 18.3 |
| Patient's assessment of pain (0-100 mm VAS) | 49.1 ± 23.5 | 43.3 ± 23.4 |
| Patient's global assessment of disease activity (0-100 mm VAS) | 46.3 ± 24.6 | 42.9 ± 22.4 |
| Physician's global assessment of disease activity (0-100 mm VAS) | 57.1 ± 16.2 | 52.5 ± 17.1 |
| HAQ DI (0-3) | 1.0 ± 0.7 | 0.9 ± 0.5 |
| C-reactive protein (mg/dL)† | 1.6 ± 1.7 | 1.0 ± 1.0 |
| Median (range) | 0.9 (0.0-7.0) | 0.7 (0.0-4.5) |
| Quality of Life Assessments | | |
| SF-36 Physical Component Summary score (0-100) | 32.7 ± 11.3 | 34.9 ± 9.2 |
| FACIT-F score (0-52) | 31.1 ± 12.3 | 34.5 ± 10.9 |
| Target Lesion Assessments | n = 30 | n = 32 |
| Target lesion, n (%) | 30 (61.2) | 32 (62.7) |
| Target lesion score (0-15) | 8.1 ± 2.3 | 7.9 ± 1.8 |
| Dermatology Life Quality Index score (0-30) | 6.2 ± 5.8 | 7.6 ± 6.3 |
| Physician's global assessment for psoriasis ("Clear" or "Almost Clear"), n (%) | 0 | 1 (3.1) |

Values are mean ± SD unless otherwise noted.
*p = 0.01 based on a Fisher's Exact test.
†p = 0.05 based on analysis of variance with baseline DMARD use and treatment as factors. P-values not calculated for medication-related categories; elsewhere, p > 0.05 unless otherwise indicated.
ACR = American College of Rheumatology;
DMARDs = disease-modifying antirheumatic drugs;
eow = every other week;
FACIT-F = 13-item fatigue scale of the Functional Assessment of Chronic Illness Therapy measure;
HAQ DI = Health Assessment Questionnaire Disability Index;
NSAIDs = non-steroidal anti-inflammatory drugs;
SF-36 = Short Form 36 Health Survey;
VAS = visual analog scale.

Patients in the adalimumab group had a numerically greater mean reduction in CRP concentration at Week 12, compared with placebo patients (−0.5 vs. 0.0, p=0.051). The mean reductions in SJC and TJC were numerically greater in the adalimumab group (−5.7 for SJC and −9.7 for TJC) compared with the placebo group (−1.9 for SJC and −6.2 for TJC), but the differences were not statistically significant (Table 42).

TABLE 42

Changes from baseline in secondary efficacy measurements

| | Week 12 | | | Week 24 | |
|---|---|---|---|---|---|
| Assessment | Placebo (n = 49) | Adalimumab (n = 51) | P-value* | Placebo/ Adalimumab (n = 46) | Adalimumab (n = 51) |
| Core ACR Assessments | | | | | |
| Swollen joint count (0-76) | −1.9 ± 11.5 | −5.7 ± 13.7 | 0.140 | −9.4 ± 13.9 | −9.1 ± 11.3 |
| Tender joint count (0-78) | −6.2 ± 10.3 | −9.7 ± 17.3 | 0.231 | −19.3 ± 14.5 | −15.7 ± 17.0 |
| Patient's assessment of pain (0-100 mm VAS) | 0.2 ± 23.1 | −15.4 ± 25.6 | 0.002 | −24.8 ± 24.4 | −19.6 ± 25.4 |
| Patient's global assessment of disease activity (0-100 mm VAS) | −0.4 ± 24.9 | −14.8 ± 24.5 | 0.004 | −19.8 ± 25.9 | −20.6 ± 24.0 |
| Physician's global assessment of disease activity (0-100 mm VAS) | −9.7 ± 18.2 | −21.4 ± 22.4 | 0.005 | −32.3 ± 20.9 | −33.5 ± 19.5 |
| HAQ DI (0-3) | −0.1 ± 0.3 | −0.3 ± 0.5 | 0.010 | −0.4 ± 0.4 | −0.3 ± 0.5 |
| C-reactive protein (mg/dL) | 0.0 ± 1.4 | −0.5 ± 1.2 | 0.051 | −1.3 ± 1.5 | −0.5 ± 0.8 |
| Additional PsA Assessment | | | | | |
| PsARC, n (%)[†] | 12 (24) | 26 (51) | 0.007 | 32 (70) | 38 (74) |
| Psoriasis Assessments | | | | | |
| Target lesion score (0-15) | n = 30 −0.3 ± 3.1 | n = 32 −3.7 ± 3.3 | <0.001 | n = 29 −4.9 ± 3.4 | n = 32 −4.5 ± 3.3 |
| Physician's global assessment for psoriasis ("Clear"/"Minimal"), n (%)[†] | n = 30 2 (6.7) | n = 32 13 (40.6) | 0.002 | n = 29 14 (48.3) | n = 32 18 (56.3) |
| Dermatology Life Quality Index score (0-30) | n = 28 −1.7 ± 5.3 | n = 32 −3.4 ± 4.5 | 0.171 | n = 26 −3.9 ± 6.4 | n = 32 −3.5 ± 5.1 |
| Quality of Life Assessments | | | | | |
| SF-36 PCS (0-100) | n = 45 2.8 ± 7.1 | n = 49 5.7 ± 8.5 | 0.082 | n = 40 11.7 ± 9.1 | n = 50 8.6 ± 7.4 |
| SF-36 MCS (0-100) | n = 45 −0.6 ± 7.82 | n = 49 1.1 ± 7.40 | 0.242 | n = 40 0.3 ± 9.7 | n = 50 1.9 ± 8.2 |
| FACIT-F score (0-52) | n = 46 2.3 ± 6.7 | n = 49 2.6 ± 7.1 | 0.783 | n = 41 5.6 ± 9.2 | n = 50 2.9 ± 8.0 |

Figure 5:
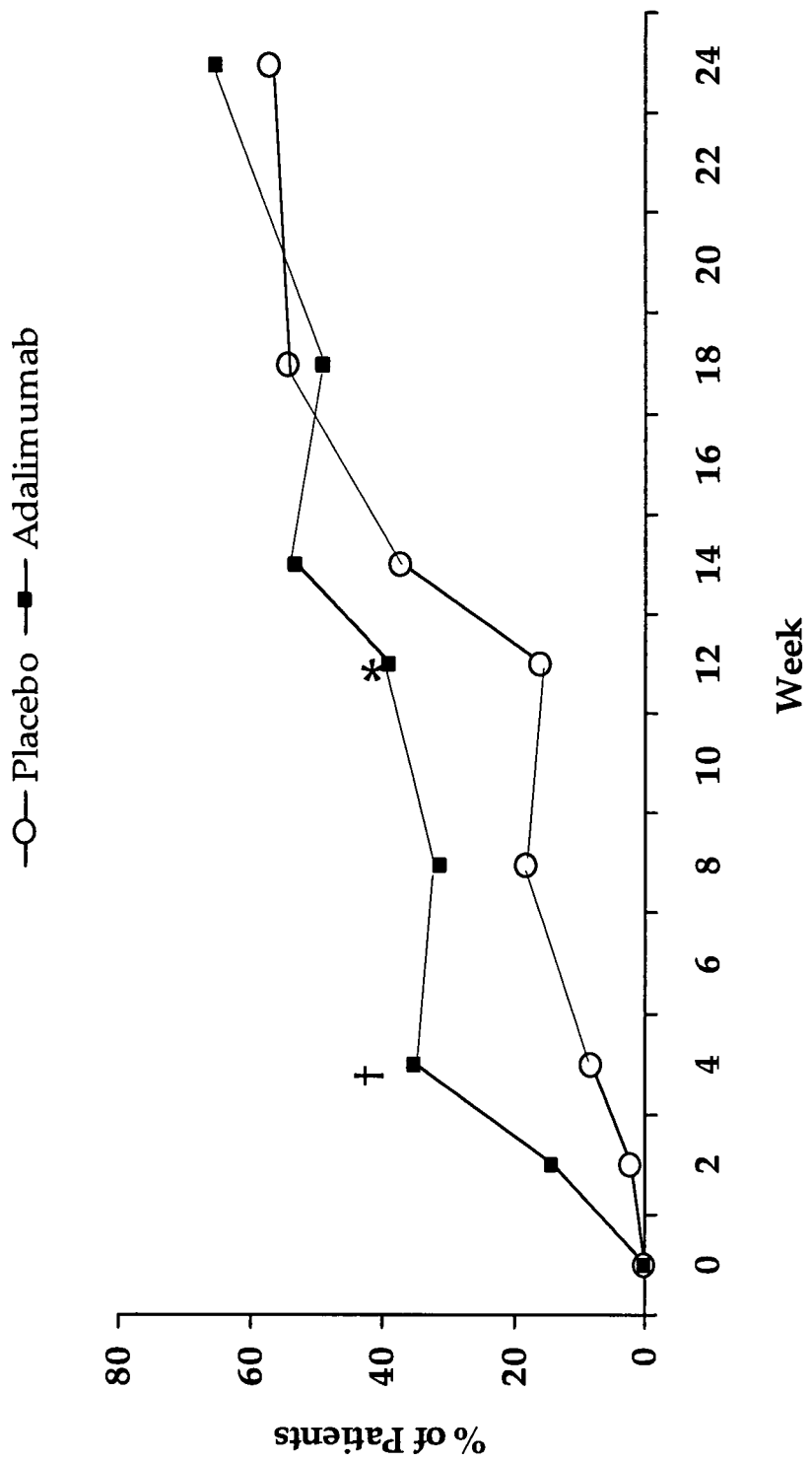
FIG. 5 shows a graphic depiction of the ACR20 over 24 weeks between placebo and adalimumab treated patients.
Figure 6:
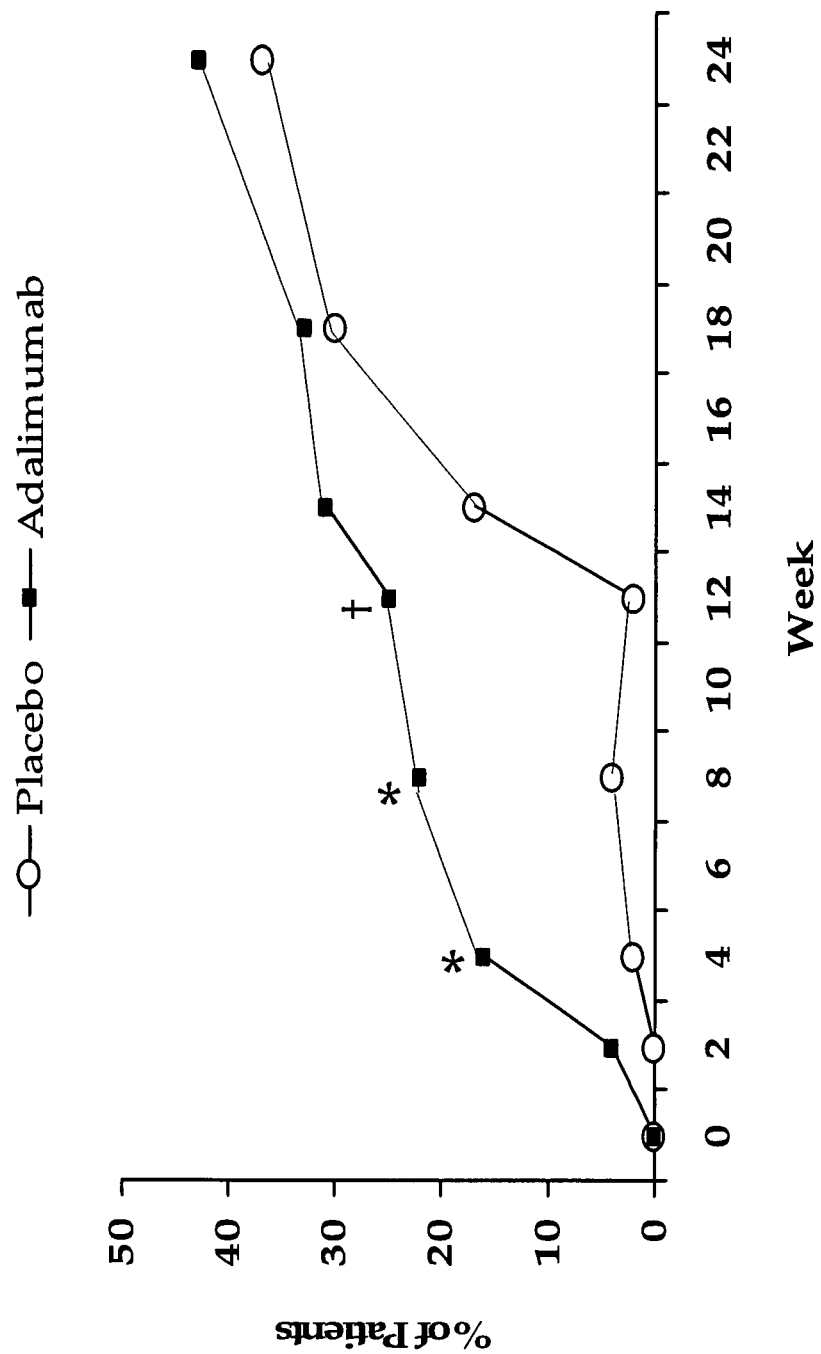
FIG. 6 shows a graphic depiction of the ACR50 over 24 weeks between placebo and adalimumab treated patients.
Figure 7:
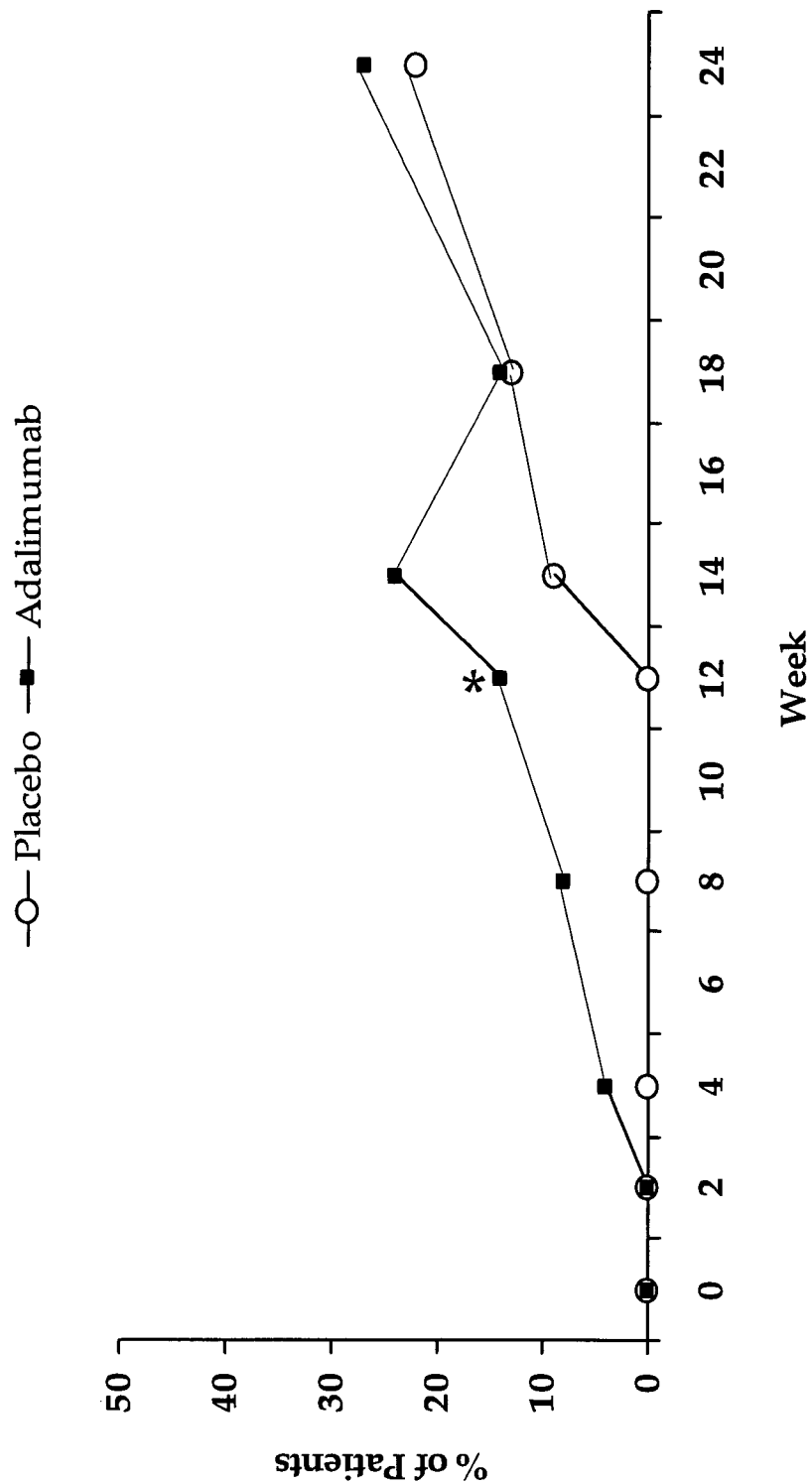
FIG. 7 shows a graphic depiction of the ACR70 over 24 weeks between placebo and adalimumab treated patients.

The ACR20 response rate was greater for adalimumab than placebo by Week 2 (FIG. 5), with the difference becoming statistically significant by Week 4 (p=0.001). Statistically significant differences were first observed at Week 4 for ACR50 (p≤0.05) (FIG. 6) and Week 12 for ACR70 (p≤0.05) (FIG. 7). For adalimumab patients, the Week 12 ACR20/50/70 response rates were similar for those who at baseline were vs. were not receiving MTX, were vs. were not receiving a DMARD, were vs. were not receiving an NSAID, and were vs. were not receiving oral corticosteroids. In addition, they were similar for patients who were RF positive vs. negative, or had a baseline serum CRP concentration ≥1 vs. <1 mg/dL. The Week 12 ACR20 for adalimumab was greater for the 29 men (52%) than for the 22 women (23%).

PsARC, Dactylitis, and Enthesitis Assessments.

The efficacy of adalimumab in treating the signs and symptoms of PsA-associated musculoskeletal disease was assessed via several additional measures (Table 42). At Week 12, the PsARC response rate for the adalimumab group (51%) was statistically significantly greater than for the placebo group (24%) (p=0.007). At Week 12, adalimumab led to numerically greater mean reductions, compared with placebo, in the dactylitis score (mean change of −2.4 for adalimumab vs. −1.4 for placebo, p>0.05) and the enthesitis score (−0.5 vs. −0.2, p>0.05).

Psoriasis Assessments.

At Week 12, the mean Target Lesion score had decreased from baseline by 3.7 units for adalimumab patients vs. 0.3 units for placebo patients (p≤0.001) (Table 42). At Week 12, the physician's global assessment for psoriasis was "Clear" or "Minimal" for significantly more adalimumab patients (40.6%, 13/32) than placebo patients (6.7%, 2/30) (p=0.002) (Table 42).

Quality of Life Assessments.

At Week 12, significant mean improvements from baseline in the Physical Functioning (p=0.027), Bodily Pain (p=0.007), General Health (p=0.017), and Mental Health (p=0.009) domains of the SF-36 were observed for adalimumab vs. placebo (data not shown). Numerically greater mean improvements were also observed for adalimumab, compared with placebo, in the Vitality domain (p=0.070), and the Role—Physical, Social Functioning, and Role—Emotional domains (all p>0.10) of the SF-36. At Week 12, numerically greater mean improvements were observed for adalimumab vs. placebo in the SF-36 PCS (5.7 vs. 2.8, p=0.082) and, to a lesser degree, the MCS (1.1 vs. −0.6, p=0.242) scores (Table 42). During the first 12 weeks of therapy, the FACIT-F scores of the two treatment groups improved by similar degrees, each <4, the unit improvement needed to be clinically meaningful (Table 42) (Cella et al, supra). The adalimumab group exhibited a numerically greater improvement in the DLQI from baseline to Week 12 vs. placebo, with mean changes from baseline of −3.4 vs. −1.7 (p=0.171) (Table 42).

Efficacy at Week 24

Arthritis Assessments During the Open-Label Period.

After 24 weeks of therapy (12 weeks double-blind plus 12 weeks open-label), the ACR20/50/70 response rates for the 51 adalimumab patients were 65%, 43%, and 27% (n=51), indicating that their arthritis continued to improve beyond Week 12. For the 46 patients who had initially received placebo and started adalimumab at Week 12, rapid improvement occurred during open-label therapy, with ACR20/50/70 rates of 57%, 37%, and 22% observed at Week 24 (Table 40 and FIG. 5). During open-label treatment, scores for the components of the ACR core criteria—SJC, TJC, patient's assessment of pain, and patient's and physician's assessments of disease activity—continued to improve for adalimumab patients and showed a markedly increased rate of improvement for placebo patients, with similar total improvements observed for the two groups at Week 24 (Table 42). PsARC responses were observed at Week 24 in 70% of patients in the placebo/adalimumab group and 74% in the adalimumab arm (Table 42). The mean changes in the HAQ DI scores from baseline to Weeks 12 and 24 were −0.1 and −0.4 for the placebo/adalimumab group, and −0.3 and −0.3 for patients in the adalimumab arm (Table 42). By Week 24, mean CRP concentrations had decreased from baseline by 1.3 mg/dL for patients in the placebo/adalimumab group and 0.5 mg/dL for patients in the adalimumab arm (Table 42).

Psoriasis Assessments During the Open-Label Period.

From Weeks 12-24, the percentages of patients who achieved physician's global assessments of "Clear" or "Minimal" increased by 43% (from 6.7% to 50.0%), for placebo patients treated with open-label adalimumab and by 16% (from 40.6% to 56.3%) for patients in the adalimumab arm (Table 42). From Weeks 12-24, Target Lesion scores decreased by 4.4 and 0.8 for patients from the placebo and adalimumab arms, respectively, resulting in total improvements from baseline of 4.7 and 4.5 (Table 42).

Quality of Life Assessments During the Open-Label Period.

After Week 12, the SF-36 PCS score began to improve markedly for adalimumab patients from the placebo arm, and continued to improve for patients from the adalimumab arm, resulting in mean increases from baseline to Week 24 of 11.7 and 8.6, respectively (Table 42). By Week 24, a small mean improvement was observed in the SF-36 MCS score for patients from each arm (Table 42). For patients from the placebo and adalimumab arms, the mean improvements in the FACIT-F scores from baseline to Week 24 were 5.6 and 2.9, respectively, and, the mean changes in the DLQI were −3.9 and −3.5 (Table 42).

Adverse Events

Adverse Events Through Week 12.

The incidence of AEs reported during the 12 weeks of double-blind therapy was statistically significantly lower for adalimumab (52.9%) vs. placebo (79.6%) (p=0.006) (Table 43). The incidences of AEs attributed to study drug during the first 12 weeks were 27.5% for adalimumab and 28.6% for placebo. The incidences of AEs reported during the first 12 weeks by =5% of patients in either group were similar, with the exception of "psoriasis aggravated" and "psoriatic arthropathy aggravated," which were reported statistically significantly more frequently by placebo-treated patients (Table 43).

TABLE 43

Adverse Events

|  | Double-Blind Weeks 0-12 | | Open-Label Weeks 12-24 |
| --- | --- | --- | --- |
|  | Placebo (n = 49) | Adalimumab 40 mg eow (n = 51) | Adalimumab 40 mg eow (n = 97) |
| Any AE | 39 (79.6)* | 27 (52.9) | 53 (54.6) |
| Any serious AE | 2 (4.1) | 1 (2.0) | 3 (3.1) |
| Any AE leading to discontinuation of study drug | 2 (4.1) | 1 (2.0) | 6 (6.2) |
| Any infectious AE | 16 (32.7) | 9 (17.6) | 29 (29.9) |
| Any serious infectious AE | 1 (2.0) | 0 | 0 |
| AEs reported by = 5% of patients in either double-blind group* | | | |
| Upper respiratory tract infection NOS | 4 (8.2) | 7 (13.7) | 6 (6.2) |
| Injection-site pain | 6 (12.2) | 6 (11.8) | 0 |
| Psoriasis aggravated | 8 (16.3)† | 2 (3.9) | 4 (4.1) |
| Diarrhea NOS | 3 (6.1) | 1 (2.0) | 2 (2.1) |
| Back pain | 3 (6.1) | 1 (2.0) | 2 (2.1) |
| Psoriatic arthropathy aggravated | 7 (14.3)† | 1 (2.0) | 1 (1.0) |
| Headache NOS | 3 (6.1) | 0 | 3 (3.1) |

Values indicate number of patients (%).
*Includes each type of AE that occurred in ≥5% of placebo group or >5% of adalimumab group during blinded treatment. During the open-label period, two additional types of AE were reported in ≥5% of the 97 patients, cough (n = 6, 6.2%) and nasopharyigitis (n = 5, 5.2%).
†p ≤ 0.05 vs. adalimumab based on Fisher's exact test.
AE = adverse event;
eow = every other week;
NOS = not otherwise specified. %

During the first 12 weeks, most AEs were mild or moderate, and there were three serious AEs and three AEs that lead to study discontinuation (Table 43). Two serious AEs occurred in placebo patients, both of whom required hospitalization, one for intravenous antibiotic treatment of a sublingual abscess, and the other for excision of a benign periganglioma neoplasm. The only adalimumab patient who experienced a serious AE during the first 12 weeks was hospitalized for treatment of diverticulitis and discontinued study medication. This patient was allowed to continue in the open-label phase. Two placebo patients discontinued study medication, one because of psoriatic arthropathy aggravated, and the other because of injection-site reaction. All three patients recovered from their SAEs. The incidence of infectious AEs to Week 12 was greater in the placebo group (32.7% vs. 17.6%). The only serious infectious AE occurred in a placebo patient. Changes in laboratory values and vital signs were not clinically significant. One placebo-arm patient had elevations of aspartate aminotransferase (AST) and alanine transaminase (ALT) concentrations >3 times the upper limit of normal (ULN) that resolved spontaneously prior to open-label adalimumab. During the first 12 weeks, there were no cases of tuberculosis/granulomatous infections, demyelination, drug-induced lupus, congestive heart failure, and malignancies, and there were no deaths.

Adverse Events Weeks 12-24.

During the open-label period of study, the rates of AEs (54.6%), serious AEs (3.1%), and AEs leading to discontinuation of adalimumab (6.2%) were consistent with those observed during the double-blind period (Table 43). The 3 SAEs comprised one case of renal failure associated with rhabdomyolysis and two cases of non-cutaneous cancer (see below). During the open-label period, there were no serious infectious AE,s and the overall rate of infectious AEs (29.9%) was similar to that observed for all patients (placebo plus adalimumab) during the blinded period (25.0%) (Table 43). During the open-label period, two additional types of AEs were reported in =5% of all patients: cough (n=6, 6.2%) and nasopharyngitis (n=5, 5.2%). One patient from the adalimumab arm had an ALT elevation >3 times ULN in the open-label extension that resolved following discontinuation of study drug. From Weeks 12-24, there were no cases of tuberculosis/granulomatous infections, demyelination, drug-induced lupus, or congestive heart failure. During this period, cancers were reported in three patients from the placebo arm, with one case each of non-Hodgkin's lymphoma (NHL), squamous cell carcinoma of the skin, and adenocarcinoma of the prostate, diagnosed 3 days, 3 days, and 83 days, respectively, after administration of the first dose of adalimumab. In retrospect, the NHL was visible on a radiograph obtained before the patient had received adalimumab. No patients died from Weeks 12-24.

To summarize the results, a total of 100 patients received study drug (51 adalimumab, 49 placebo). At Week 12, an ACR20 response was achieved by 39% of adalimumab patients vs. 16% of placebo patients (p=0.012), and a PsARC response was achieved by 51% with adalimumab vs. 24% with placebo (p=0.007). At Week 12, measures of skin lesions and disability were statistically significantly improved with adalimumab. After Week 12, open-label adalimumab provided continued improvement for adalimumab patients, and initiated rapid improvement for placebo patients, with ACR20 response rates of 65% and 57%, respectively, observed at Week 24. Adverse events occurred in 53% of adalimumab patients during the double-blind period vs. 80% of placebo patients (p=0.006).

This study was a 12-week, randomized, double-blind, placebo-controlled trial with a 12-week open-label extension that evaluated adalimumab therapy in 100 adult patients with moderate to severe PsA who had failed DMARD therapy. The results demonstrated that adalimumab was efficacious in reducing the signs, symptoms, and functional disability of PsA, as well as the severity of the associated psoriasis. Adalimumab was observed to be generally safe and well-tolerated over 24 weeks of use.

The present study was the second Phase III trial to demonstrate adalimumab's safety and efficacy in patients with moderately to severely active PsA. The first such trial was Study G, which assessed treatment in 313 patients who had failed to respond adequately to NSAID therapy (Mease et al, 2005). Both trials studied patients with long-standing disease in a two-arm protocol comparing adalimumab 40 mg eow with placebo. In each study, approximately half of patients received concomitant MTX at baseline. Concomitant use of other DMARDs was permitted only in the present study. In Study G, the ACR20 response rates following 12 and 24 weeks of blinded treatment with adalimumab were 58% and 57%, respectively (Mease et al, 2005). In the present study, ACR20 rates were 39% following 12 weeks of blinded adalimumab; 65% for these patients following 12 more weeks of adalimumab, given open-label; and 57% for patients from the placebo arm following 12 weeks of open-label treatment with adalimumab. ACR50 and ACR70 rates in the present trial at 24 weeks, and in Study G at 12 and 24 weeks, were also similar. Both studies showed statistically significant improvements in the PsARC response with blinded adalimumab treatment. Thus, the present study and Study G both demonstrate the efficacy of adalimumab in treating the arthritis component of PsA.

The present study and Study G both demonstrate that adalimumab was efficacious in improving psoriasis and physical function. In the present study, 12 weeks of adalimumab led to statistically significant improvements in the physician's global assessment of psoriasis and in the Target Lesion score, with each being maintained through the open-label period to Week 24. In Study G, the Weeks 12 and 24 PASI50/75/90 rates were statistically significantly greater for blinded adalimumab vs. placebo, as was the improvement in the physician's global assessment at Week 24 (Mease et al, 2005). In the present study, the mean changes in the HAQ DI observed for adalimumab-arm patients at Weeks 12 and 24 (−0.3 and −0.3), and for placebo-arm patients following 12 weeks of open-label adalimumab (−0.4), were similar to the −0.4 mean change in the HAQ DI observed in Study G following 12 and 24 weeks of blinded adalimumab treatment (Mease et al, 2005). These changes in HAQ DI equal or exceed the minimum clinically important differences (MCID) reported for PsA (0.3) (Mease et al, *Ann Rheum Dis* 2004a; 63(Suppl 1):391-2.) and RA (0.22) (Goldsmith C H, et al., *Rheumatology* 1993; 20:561-5.).

In both the present study and Study G, there was evidence of a therapeutic effect following the first injection of adalimumab. However, during the first 12 weeks of the present study, response to adalimumab developed more slowly than expected, compared with: 1) the greater response rates of these patients at Week 24; 2) the greater response rates observed for placebo-arm patients at Week 24; or 3) the greater response rates for Study G patients following 12 weeks of blinded adalimumab (Mease et al, 2005, supra). The reasons for the delayed response to adalimumab are uncertain. Most baseline parameters were similar for the adalimumab and placebo patients in the present study. The two parameters of disease activity with significant between-group differences at baseline, the percentage of RF-negative patients and the mean CRP concentration, were both lower in the adalimumab arm, but subset analyses failed to reveal efficacy differences that could explain the Week 12 adalimumab results. Comparisons based on whether concomitant medications were used at baseline in the present study were also unrevealing. A higher ACR20 response rate with adalimumab was observed for men vs. women in the present study, but the relevance of this observation is unclear because the patient numbers were small and the sexes were similarly represented in each treatment arm. Moreover, in the much larger study population of Study G, men and women had equal Week 12 ACR20 response rates: 58% (Mease et al, 2005). Thus, the delayed response observed in the adalimumab arm of the present study was not observed elsewhere, and was probably a result of random effects unique to that small treatment group.

Adalimumab was generally safe and well-tolerated during the blinded and open-label periods of the present trial, as demonstrated by the incidence and severity of AEs, the incidence of serious AEs, the frequency of treatment discontinuations, and the results of laboratory monitoring.

During the 12 weeks of blinded treatment, infections occurred in adalimumab patients approximately half as frequently as they did in placebo patients, but the difference was not statistically significant. Upper respiratory tract infections accounted for most of the infections reported during blinded adalimumab treatment, consistent with previous studies. (Keystone E C, et al., *Arthritis Rheum* 2004; 50:1400-11; van de Putte L B A, et al. *Ann Rheum Dis* 2004; 63:508-16; Weinblatt M E, et al. *Arthritis Rheum* 2003; 48:35-45. *Erratum in: Arthritis Rheum* 2003; 48:855. Arthritis Rheum 2004; 22:144). There were no cases of tuberculosis/granulomatous infections, demyelination, drug-induced systemic lupus erythematosus, or congestive heart failure during the 24-week observation period reported here. No cancers were observed in adalimumab-arm patients over 24 weeks. Of the three cancers reported in placebo-arm patients during the open-label period, one was retrospectively apparent prior to treatment with adalimumab and another was diagnosed 3 days after the first adalimumab injection. The safety profile of adalimumab in the present study was consistent with that reported in previous clinical studies of adalimumab in patients with PsA (Mease et al, 2005) and rheumatoid arthritis (Keystone et al, 2004; van de Putte et al, 2004; Weinblatt et al, 2003; Schiff M H, et al., *Ann Rheum Dis* 2006; 65:889-94.), and with that of other TNF antagonists in PsA. (Mease et al, 2004; Antoni C, et al., *Ann Rheum Dis* 2005; 64: 1150-7 (b))

In summary, the present study evaluated PsA patients who had moderately to severely disease and inadequate response to DMARD therapy. It was the second Phase III trial to assess the efficacy and safety of adalimumab therapy for long-standing PsA. Despite the relatively small size of this study, adalimumab was demonstrated to have been well-tolerated, to have significantly reduced the signs and symptoms of arthritis, and to have significantly improved psoriasis and disability. In patients who had moderately to severely active PsA and an inadequate response to DMARD therapy, adalimumab was well-tolerated and significantly reduced the signs, symptoms, and disability of PsA during 12 weeks of blinded and 12 weeks of open-label therapy. Adalimumab also improved psoriasis in these patients.

Example 12

Adalimumab Radiographic Efficacy in Patients with Psoriatic Arthritis According to Demographics, Baseline Clinical Status, Methotrexate Use, and Clinical Response: Subanalysis of Study G Study G is the largest randomized, double-blind, placebo-controlled trial of a TNF antagonist in psoriatic arthritis (PsA) to date. Study J demonstrated that 24 weeks of treatment with adalimumab improved arthritis, skin disease, and quality of life, and prevented radiographic joint destruction in patients with PsA. Study J patients predominantly had long-standing, polyarticular disease, and approximately half used methotrexate (MTX) during the trial. It is not known whether the radiographic efficacy of adalimumab in the overall Study G population was restricted to any patient subsets.

This post-hoc analysis of Study G, a randomized trial of patients (pts) with psoriatic arthritis (PsA), determined whether adalimumab (ADA) had radiographic efficacy in patient subgroups defined by selected baseline (BL) parameters or by clinical response of arthritis to therapy.

Changes from BL in the modified version of the total Sharp score (mTSS) were determined for pts grouped post-hoc by demographic parameters (age, sex, race, weight), measurements of BL clinical status (Serum C-reactive protein (CRP), RF, tender joint count (TJC), swollen joint count (SJC), Health Assessment Questionnarie (HAQ), methotrexate (MTX) use at BL, and 20% improvement in American College of Rheumatology (ACR20) core criteria response at Wk 24. Within each subgroup, the Wk 24 mean change in mTSS was compared for ADA vs. PBO. Analyses were restricted to pts who had evaluable radiographs at BL and Wk 24.

The present study analyzed data from patients who had evaluable radiographs at baseline and Week 24. Numbers of joints evaluated were 78 for tender joint count (TJC) and 76 for swollen joint count (SJC). Serum C-reactive protein (CRP) was assessed with a high-sensitivity assay; upper limit of normal =0.287 mg/dL. Baseline mTSS and Week 24 clinical and radiographic outcomes were determined for patients grouped post hoc by: Demographic parameters (age, sex, race, and weight); Baseline clinical characteristics (PsA disease duration, RF, TJC, SJC, HAQ DI, CRP); MTX use at baseline; and ACR response at Week 24 (included only patients with observed ACR scores at Week 24). Mean change in mTSS at Week 24 was compared within each subgroup for adalimumab vs. placebo.

313 patients received treatment with adalimumab or placebo in Study G. Baseline demographics and disease characteristics were similar for both treatment groups (see Table 1 above). Overall ACR 20/50/70 results at Week 24 were 15/6/1 for placebo (N=162) and 57/39/23 for adalimumab (N=151) (Mease et al. *Arthritis Rheum.* 2005; 52:3279-3289). Radiographs were available at baseline and Week 24 for 152 placebo and 144 adalimumab patients.

Of 313 pts enrolled in Study G, 296 had evaluable radiographs at BL and Wk 24. By Week 24, adalimumab had significantly reduced the overall amount of radiographic progression vs. placebo. Specifically, the mean change in mTSS from baseline to Week 24 was 1.0 for placebo (n=152), and −0.2 for ADA (n=144) (p<0.001 vs. placebo for the ADA group). For all demographic subgroups with an adequate number of patients, the mean ΔmTSS at Week 24 with adalimumab was ≤0 and was significantly lower with than with placebo (Table 44).

TABLE 44

Mean Change in mTSS at Week 24 for Demographic Subgroups

| | <40 years | | =40 years to <60 years | | =60 years | |
|---|---|---|---|---|---|---|
| | Placebo (n = 29) | ADA (n = 36) | Placebo (n = 100) | ADA (n = 84) | Placebo (n = 23) | ADA (n = 24) |
| Mean Change in mTSS | 0.6 | −0.3* | 1.1 | −0.1† | 1.2 | −0.1± |

TABLE 44-continued

| | | | | | | |
|---|---|---|---|---|---|---|
| Mean Baseline mTSS | 8.4 | 11.4 | 23.3 | 18.7 | 20.0 | 51.2 |

*p = 0.009,
†p < 0.001,
‡p = 0.014, vs. placebo

| | Male | | Female | |
|---|---|---|---|---|
| | Placebo (n = 84) | ADA (n = 81) | Placebo (n = 68) | ADA (n = 63) |
| Mean Change in mTSS | 0.6 | −0.3* | 1.6 | 0.0† |
| Mean Baseline mTSS | 14.3 | 16.5 | 26.9 | 29.8 |

*p < 0.001,
†p = 0.001, both vs. placebo

| | Caucasian | | Non-Caucasian | |
|---|---|---|---|---|
| | Placebo (n = 143) | ADA (n = 140) | Placebo (n = 9) | ADA (n = 4) |
| Mean Change in mTSS | 0.9 | −0.2* | 2.8 | 0.3 |
| Mean Baseline mTSS | 19.8 | 22.6 | 23.3 | 11.9 |

*p < 0.001 vs. placebo

| | <86 kg | | =86 kg | |
|---|---|---|---|---|
| | Placebo (n = 76) | ADA (n = 76) | Placebo (n = 75) | ADA (n = 68) |
| Mean Change in mTSS | 1.0 | −0.1* | 2.7 | 0.3* |
| Mean Baseline mTSS | 21.2 | 29.8 | 18.9 | 13.9 |

*p < 0.001 vs. placebo

At Week 24, the mean ΔmTSS with adalimumab was ≤0 and was significantly smaller than placebo for patients who did or did not use MTX at baseline, and for each subgroup defined by clinical status at baseline (Table 45). For patients with a baseline CRP≥2.0 mg/dL, the mean mTSS at baseline was relatively high (~44, overall); at Week 24, the difference between the mean ΔmTSS with placebo vs. adalimumab, 3.1, was greater than for any other subgroup (Table 45).

TABLE 45

Mean Change in mTSS at Week 24 by Baseline MTX Use or Clinical Status

| | Baseline MTX Use | | | |
|---|---|---|---|---|
| | MTX(+) | | MTX(−) | |
| | Placebo (n = 78) | ADA (n = 74) | Placebo (n = 74) | ADA (n = 70) |
| Mean Change in mTSS | 1.2 | −0.2* | 0.9 | −0.2† |
| Mean Baseline mTSS | 25.0 | 21.7 | 14.6 | 22.9 |

*p < 0.001,
†p = 0.001, both vs. placebo

TABLE 45-continued

| | PsA Disease Duration | | | |
|---|---|---|---|---|
| | <5 years | | =5 years | |
| | Placebo (n = 57) | ADA (n = 53) | Placebo (n = 95) | ADA (n = 91) |
| Mean Change in mTSS | 1.4 | −0.2* | 0.8 | −0.1* |
| Mean Baseline mTSS | 15.7 | 10.9 | 22.5 | 28.9 |

*p < 0.001 vs. placebo

| | Rheumatoid Factor | | | |
|---|---|---|---|---|
| | (+) RF | | (−) RF | |
| | Placebo (n = 14) | ADA (n = 15) | Placebo (n = 137) | ADA (n = 129) |
| Mean Change in mTSS | 1.0 | −0.1* | 1.0 | −0.2† |
| Mean Baseline mTSS | 20.9 | 41.4 | 19.0 | 20.1 |

*p = 0.018,
†p < 0.001 both vs. placebo

| | Tender Joint Count | | | |
|---|---|---|---|---|
| | TJC < 20 | | TJC = 20 | |
| | Placebo (n = 68) | ADA (n = 73) | Placebo (n = 84) | ADA (n = 71) |
| Mean Change in mTSS | 0.6 | 0* | 1.4 | −0.3† |
| Mean Baseline mTSS | 15.7 | 21.1 | 23.4 | 23.6 |

*p = 0.006,
†p < 0.001 both vs. placebo

| | Swollen Joint Count | | | |
|---|---|---|---|---|
| | SJC < 20 | | SJC = 20 | |
| | Placebo (n = 118) | ADA (n = 118) | Placebo (n = 34) | ADA (n = 26) |
| Mean Change in mTSS | 0.6 | −0.2* | 2.5 | −0.1† |
| Mean Baseline mTSS | 15.6 | 19.3 | 35.0 | 35.8 |

*p < 0.001,
†p = 0.016, both vs. placebo

TABLE 45-continued

HAQ DI Score

|  | HAQ < 1.5 | | HAQ = 1.5 | |
| --- | --- | --- | --- | --- |
|  | Placebo (n = 107) | ADA (n = 107) | Placebo (n = 45) | ADA (n = 37) |
| Mean Change in mTSS | 0.6 | −0.1* | 2.1 | −0.4* |

TABLE 46

Mean changes in mTSS by patient subgroup

| | PBO | | | ADA | | |
| --- | --- | --- | --- | --- | --- | --- |
| Pt subgroup | N | BL mTSS (Mean) | Week 24 ΔmTSS (Mean ± SD) | N | BL mTSS (Mean) | Week 24 ΔmTSS (Mean ± SD) | p value* |
| CRP < 2.0 | 110 | 10.7 | 0.4 ± 1.25 | 117 | 17.5 | −0.1 ± 1.25 | <0.001 |
| CRP ≥ 2.0 | 42 | 44.3 | 2.6 ± 5.03 | 27 | 43.0 | −0.5 ± 1.87 | <0.001 |
| SJC < 20 | 118 | 15.6 | 0.6 ± 1.74 | 118 | 19.3 | −0.2 ± 1.23 | <0.001 |
| SJC ≥ 20 | 34 | 35.0 | 2.5 ± 5.25 | 26 | 35.8 | −0.1 ± 1.98 | 0.016 |
| HAQ < 1.5 | 107 | 13.6 | 0.6 ± 1.85 | 107 | 17.8 | −0.1 ± 1.15 | <0.001 |
| HAQ ≥ 1.5 | 45 | 35.1 | 2.1 ± 4.58 | 37 | 35.3 | −0.4 ± 1.92 | <0.001 |

*By analysis of variance, with treatment group, BL MTX use, and extent of psoriasis as factors, and ranked BL mTSS as covariate.

TABLE 45-continued

| Mean Baseline mTSS | 13.6 | 17.8 | 35.1 | 35.3 |
| --- | --- | --- | --- | --- |

*p < 0.001 vs. placebo

C-Reactive Protein

|  | CRP < 2.0 mg/dL | | CRP = 2.0 mg/dL | |
| --- | --- | --- | --- | --- |
|  | Placebo (n = 110) | ADA (n = 117) | Placebo (n = 42) | ADA (n = 27) |
| Mean Change in mTSS | 0.64 | −0.1* | 2.6 | −0.5* |
| Mean Baseline mTSS | 10.7 | 17.5 | 44.3 | 43.0 |

*p < 0.001 vs. placebo. Upper limit of normal for CRP = 0.287 mg/dL

Figure 8:
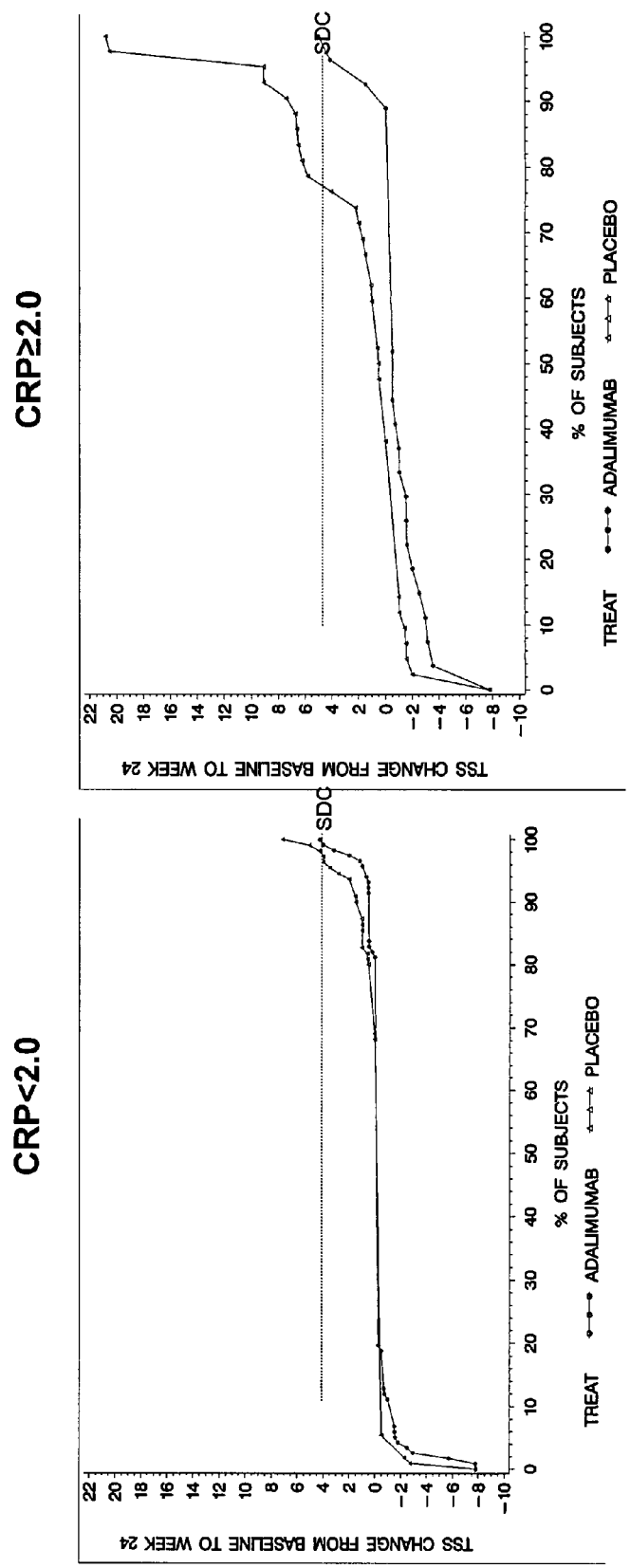
FIG. 8 shows the mean probability plots of week 24 change in mTSS for baseline CRP subgroups.

For each CRP subgroup, the probability plot for adalimumab patients was lower than for placebo patients (FIG. 8). The smallest detectable change (SDC) of 1.88 was exceeded by 9.1% (placebo) vs. 3.4% (adalimumab) of patients with baseline CRP<2.0 mg/dL, and 31.0% vs. 7.4% of patients with baseline CRP≥2.0 mg/dL. More severe radiographic progression (e.g., ΔmTSS>4.0) occurred predominantly in placebo patients with baseline CRP≥2.0 mg/dL, and was nearly absent with adalimumab (FIG. 8). Mean radiographic progression with placebo treatment was greatest in the Week 24 ACR nonresponders (ACR<20) (FIG. 8). With adalimumab treatment, the mean ΔmTSS at Week 24 was =0 for ACR nonresponders and ACR20 responders (FIG. 8).

Overall, the mean changes in mTSS at Wk 24 were 1.0 vs. −0.2 for pts treated with PBO vs. ADA (p<0.001). In the post-hoc analysis, statistically significantly smaller changes in the mTSS from BL to Wk 24 were observed with ADA, compared with PBO, in all subgroups with sufficient pt numbers. The largest differences in progression between ADA and PBO were observed in subgroups with BL CRP≥2.0, SJC≥20 or HAQ≥1.5 (3.1, 2.6, and 2.5, respectively) (Table 46). The mean changes in mTSS from BL to Wk 24 were −0.2 (ADA) vs. 1.2 (PBO) (p<0.001) for pts using MTX at BL (51% of 296 pts, mean dosage 17.1 mg/wk), and −0.2 (ADA) vs. 0.9 (PBO) (p=0.001) for patients not using MTX at baseline. For pts who had a <ACR20 response at Wk 24, the mean changes in mTSS at Wk 24 were 0.0 (ADA, n=51) vs. 1.2 (PBO, n=121) (p=0.001), and for patients who achieved an ACR20 response at Wk 24, they were −0.3 (ADA, n=86) vs. 0.2 (PBO, n=25) (p=0.003).

In this post hoc analysis of Study G, the Week 24 mean change in mTSS with adalimumab was ≤0, and was significantly smaller than with placebo, for all adequately large patient subgroups, including those defined by weight, SJC, and CRP.

For pts with PsA in Study G, ADA had radiographic efficacy at Wk 24 in every assessable subgroup. Efficacy was observed whether or not pts used MTX at BL or had an ACR20 response at Wk 24. Pts with a BL CRP≥2.0 had particularly severe radiographic progression, suggesting that CRP may be a marker for aggressive joint destruction in PsA, and that ADA inhibits radiographic progression in such pts. Adalimumab inhibited the mean radiographic progression at Week 24 compared with placebo, whether or not patients were ACR20 responders Example 13

Adalimumab (HUMIRA®) is Effective and Safe in Treating Psoriatic Arthritis (PsA) in Real-Life Clinical Practice: Preliminary Results of Study P Psoriatic arthritis (PsA), a seronegative spondylarthropathy, is often progressive and disabling. PsA has been reported in more than 30% of psoriasis patients (Peters et al. *Am J Health Syst Pharm* 2000; 57:645-62) and a great percentage of these patients have progressive, destructive arthritis leading to a significantly poorer quality of life (de Arruda L H F, de Moraes A P F. *Br J Dermatol* 2001; 144 (Suppl. 58):33-6). Traditional treatment approaches in PsA include nonsteroidal anti-inflammatory drugs, corticosteroids and disease-modifying antirheumatic drugs (DMARDs). Frequently used DMARDs include sulfasalazine, methotrexate, cyclosporine, and leflunomide. Clinical trials with adalimumab in patients with PsA have shown significant results in improvement of joint and skin disease, quality of life, and function (Mease et al. *Arthritis Rheum* 2005; 52:3279-89)

Efficacy and safety of anti-TNFs in patients (pts) with active PsA have been confirmed in clinical trials and supported by post-marketing data. Study P, a prospective, open-label trial, examined the efficacy and safety of adalimumab (ADA) in a large number of pts with active PsA, in real-life clinical practices, including pts with various comorbidites, pts who had been treated unsuccessfully with other TNF antagonists, and/or pts who were receiving various concomitant DMARDs.

Methods included the following: unsatisfactory response or intolerance to at least one prior DMARD was required for enrollment in STEREO. The patient enrollment was in accordance with the current national guidelines for treatment of PsA with TNF inhibitors. Patients with active PsA received adalimumab 40 mg every other week (eow) subcutaneously (sc) in addition to their existing, but insufficient, PsA therapy. Active PsA was defined by ≥3 tender and ≥3 swollen joints despite standard PsA therapy.

Key efficacy outcomes measured included: ACR20/50/70; Tender Joint Count 78 (TJC 78) and Swollen Joint Count 76 (SJC 76); Change in Disease Activity Score 28 (DAS28); Health Assessment Questionnaire (HAQ); Physician's Global Assessment for Psoriasis (PGA); and Dermatology life quality index (DLQI). Efficacy data and adverse events (AE) were collected at Weeks 2, 6, and 12 during the 12-week period and at Week 20 for those patients who optionally continued the study after Week 12

Thus, adult patients with active PsA, who had insufficient responses to at least 1 prior DMARD, received ADA 40 mg sc every other week (wk) for 12 weeks in the Study P trial. Treatment was optionally extended to Week 20 when ADA was not generally available by Week 12. Efficacy evaluations on joints and skin and routine safety evaluations were conducted at Weeks 2, 6, and 12, and optionally at Week 20. Adverse events (AE) were collected throughout the treatment period.

As of April 2006, 253 patients (52% male), of the total 441 from 85 sites in 9 European countries enrolled in Study P, had completed Week 12. Mean baseline characteristics of these patients included: age, 49 yrs; psoriasis duration, 20 yrs; and PsA duration, 11 yrs. Dactylitis was present in 30% of patients, and enthesitis of achilles-tendon and/or plantar-facia in 32% of patients.

Baseline Characteristics

At baseline, patients with prior exposure to etanercept (ETN) and/or infliximab (IFX) had a slightly higher disease activity than prior biologic-naïve patients (Table 47). Patients with prior biologic therapy were somewhat more limited in their physical function, as measured by disability index Health Assessment Questionnaire (HAQ) (Table 47).

TABLE 47

|  | No prior Biologics (N = 185) | Prior Biologics (ETN, IFX) (N = 47) | All Patients (N = 253) |
| --- | --- | --- | --- |
| Age (mean, years) | 49 ± 11 | 47 ± 12 | 49 ± 12 |
| Male, % | 53 | 45 | 52 |
| Body Weight (kg) | 83 ± 19 | 82 ± 18 | 83 ± 19 |

TABLE 47-continued

|  | No prior Biologics (N = 185) | Prior Biologics (ETN, IFX) (N = 47) | All Patients (N = 253) |
| --- | --- | --- | --- |
| Duration of PsA (years) | 11 ± 9 | 12 ± 8 | 11 ± 9 |
| Duration of Psoriasis (years) | 20 ± 13 | 20 ± 14 | 20 ± 14 |
| Dactylitis (% of patients) | 30 | 26 | 30 |
| Enthesitis (% of patients) | 32 | 34 | 32 |
| TJC (0-78) | 17.6 ± 12.7 | 16.4 ± 12.0 | 17.6 ± 12.5 |
| SJC (0-76) | 9.7 ± 6.4 | 7.0 ± 3.7 | 9.3 ± 6.2 |
| DAS28 | 4.7 ± 1.1 | 4.9 ± 1.2 | 4.8 ± 1.2 |
| HAQ | 1.2 ± 0.6 | 1.4 ± 0.6 | 1.2 ± 0.6 |
| PGA ("Clear"/"Almost Clear"), % | 36 | 39 | 35 |
| DLQI | 6.1 ± 6.2 | 7.4 ± 6.8 | 6.4 ± 6.4 |

Mean values ± SD except percentages at screening (Week 0).
Data records for 21 patients with prior therapies will be completed at trial end.
ETN = etanercept;
IFX = infliximab.
Observed values.

Key efficacy outcomes are summarized in Table 48.20% of patients had failed prior etanercept and/or infliximab therapy but responded well to ADA. ADA was well-tolerated, with 19 serious adverse events (SAE) reported for all 441 patients exposed to ADA. SAEs possibly related to ADA, as defined by the investigator, included abdominal pain, anemia, dental abscess, urosepsis, fever with reduced general condition, allergic reaction, and severe hip pain. No new safety events on adalimumab were observed.

TABLE 48

Efficacy of Adalimumab Up to Week 12

| Efficacy Criteria | Screening | Week 2 | Week 6 | Week 12 |
| --- | --- | --- | --- | --- |
| ACR20 (%) | — | 38 | 60 | 72 |
| ACR50 (%) | — | 14 | 35 | 49 |
| ACR70 (%) | — | 2 | 13 | 27 |
| TJC (0-78) | 17.6 | 11.6 | 8.7 | 7.3 |
| SJC (0-76) | 9.3 | 5.2 | 3.2 | 2.3 |
| HAQ | 1.20 | 0.96 | 0.91 | 0.86 |
| DAS28 | 4.8 | 3.4 | 2.9 | 2.6 |
| PGA ("Clear"/"Almost Clear", %) | 35 | 39 | 53 | 65 |
| DLQI (0-30)† | 6.4 | NA± | NA± | 2.8 |

Mean values except percentages.
*PGA = physician's global assessment of psoriasis (7-point scale),
†DLQI = Dermatology Life Quality Index (questionnaire),
±NA = not available.
Completer analysis, observed values, n = 253.

Adalimumab treatment was effective as assessed by ACR response rates up to Week 12 in patients with moderately to severely active PsA (Table 49).

TABLE 49

ACR Responses Up to Week 12

|  | Week 2 | Week 6 | Week 12 |
| --- | --- | --- | --- |
| ACR20 (% Patients) | 38 | 60 | 72 |
| ACR50 (% Patients) | 14 | 35 | 49 |
| ACR70 (% Patients) | 2 | 13 | 27 |

Adalimumab had a similar effect on ACR response rates in patients who were biologic-naïve compared to those treated with prior biologic therapy at Week 12 (Table 50).

TABLE 50

ACR Responses in Biologic Naïve Patients and Patients with Prior Biologics at Week 12

|  | Biologic Naïve (n = 185) | Prior Biologics (n = 47) |
|---|---|---|
| ACR20 | 71 | 69 |
| ACR50 | 51 | 42 |
| ACR70 | 28 | 20 |

Observed Values

Adalimumab was effective in decreasing the number of tender and swollen joint counts up to Week 12 (Table 51).

TABLE 51

Mean Change from Baseline in Tender and Swollen Joint Counts through Week 12

|  | TJC | SJC |
|---|---|---|
| Week 0 | 17.6 | 9.3 |
| Week 2 | 11.6 | 5.2 |
| Week 6 | 8.7 | 3.2 |
| Week 12 | 7.3 | 2.3 |

Total patient population includes with and without prior biologic treatment (n = 253).
Observed values.

Disease activity scores in the total patient population with exposure to adalimumab continued to decrease compared to baseline through Week 12, as measured by the mean change from baseline in DAS28 (Table 52).

TABLE 52

Mean Change from Baseline in DAS28 Scores through Week 12

|  | Mean Change from Baseline |
|---|---|
| Week 2 | −1.4 |
| Week 6 | −1.9 |
| Week 12 | −2.2 |

Total patient population includes with and without prior biologic treatment (n = 253).
Observed values.

Disease activity scores in prior-biologic patients with exposure to adalimumab continued to decrease compared to baseline through Week 12, as measured by the mean change from baseline in DAS28 (Table 53).

TABLE 53

Mean Change from Baseline in DAS28 Scores through Week 12 by Prior Exposure too Biologic Anti-TNFs

|  | Biologic Naïve (n = 185) | Prior Biologics (n = 47) |
|---|---|---|
| Week 2 | −1.4 | −1.2 |
| Week 6 | −1.9 | −1.6 |
| Week 12 | −2.2 | −2.1 |

Observed Values

Health assessment in the total patient population with exposure to adalimumab continued to decrease compared to baseline through Week 12, as measured by the mean change from baseline in HAQ (Table 54).

TABLE 54

Mean Change from Baseline in HAQ Scores through Week 12

|  | Mean Change from Baseline |
|---|---|
| Week 2 | −0.24 |
| Week 6 | −0.29 |
| Week 12 | −0.34 |

Total patient population includes with and without prior biologic treatment; N = 153.
MCID was-0.3 (Mease PJ, et al., Ann Rheum Dis. 2004, 63 (Suppl 1): 391-392.
Observed values.

Disease activity scores in prior-biologic patients with exposure to adalimumab continued to decrease compared to baseline through Week 12, as measured by the mean change from baseline in DAS28 (Table 55).

TABLE 55

Mean Change from Baseline in HAQ Scores through Week 12 by Prior Exposure to Biologic Anti-TNFs

|  | Biologic Naïve (n = 185) | Prior Biologics (n = 47) |
|---|---|---|
| Week 2 | −0.24 | −0.30 |
| Week 6 | −0.29 | −0.28 |
| Week 12 | −0.34 | −0.36 |

Observed Values.
MCID was-0.3 (Mease PJ, et al., Ann Rheum Dis. 2004; 63 (Suppl 1): 391-392.

At Week 12, the percentage of adalimumab-treated patients with a PGA score of "Clear"/"Almost Clear" was greater in both biologic-naïve and prior-biologic patient groups than at screening (Table 56).

TABLE 56

PGA "Clear"/"Almost Clear" At Screening and Week 12

|  | Biologic Naïve (n = 185) | Prior Biologics (n = 47) |
|---|---|---|
| Screening | 36 | 39 |
| Week 12 | 66 | 63 |

Observed Values.

At Week 12, patients treated with adalimumab achieved an improvement in quality of life, as measured by mean DLQI scores (Table 57).

TABLE 57

Mean DLQI Scores at Week 12

|  | Mean DLQI Scores (n = 253) |
|---|---|
| Screening | 6.4 |
| Week 12 | 2.8 |

Observed Values.
Total patient population includes with and without prior biologic treatment.

The overall results showed that adalimumab was overall well-tolerated during the 12-week exposure. Out of 441 patients exposed to adalimumab, 19 (4%) serious adverse events (SAE) were reported. SAEs possibly related to adalimumab, as defined by the investigator, included abdominal pain, anaemia, dental abscess, urosepsis, fever with reduced general condition, allergic reaction, severe hip pain, and hypersomnia. The spectrum of adverse events was similar to those reported in pivotal studies with adalimumab and in studies with other biologics. Rates of withdrawal because of adverse events were similar among patients naïve to biologics and those exposed to prior biologics. No new safety concerns following adalimumab therapy were observed. The percentage of patients who prematurely dropped out before reaching Week 12 for various reasons was low (8%)

In conclusion, ADA provided clinically significant joint and skin improvements. Study P data confirm results observed in earlier ADA pivotal trials. The benefit-risk ratio of ADA-treated pts with PsA in real-life clinical practice is positive. In patients with long-standing PsA and an insufficient response to prior biologic therapies in real-life clinical practice, the addition of adalimumab let to clinically important skin and joint improvements at Week 12 in all key efficacy parameters. Adalimumab was well-tolerated in patients who were treated with or without prior biologics, particularly ETN and IFX. Withdrawal rates because of lack of efficacy or intolerance within 12 weeks were low.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A method of treating a subject having oligoarthritis with a tender joint count (TJC)<5 or a swollen joint count (SJC)<5, in association with psoriatic arthritis, the method comprising administering to the subject about 40 mg of adalimumab once subcutaneously every other week, wherein at least an ACR20 response is achieved following a treatment period of at least about 12 weeks and the at least an ACR20 response is maintained following a treatment period of at least about 48 weeks, thereby treating the subject having psoriatic arthritis with oligoarthritis in association with psoriatic arthritis.

2. The method of claim 1, wherein at least an ACR50 response achieved by the subject following a treatment period of about 12 weeks and the at least an ACR50 response is maintained following a treatment period of at least about 48 weeks.

3. The method of claim 1, wherein said treatment period is about 48 weeks.

4. The method of claim 2, wherein said treatment period is about 48 weeks.

5. The method of claim 1, wherein at least an ACR70 response is achieved by the subject following a treatment period of about 12 weeks and the at least an ACR 70 response is maintained following a treatment period of at least about 48 weeks.

6. The method of claim 5, wherein said treatment period is about 48 weeks.

* * * * *

SEQUENCE LISTING

```
<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Lys Val Ser Tyr Leu Ser Thr Ala Ser Ser Leu Asp Tyr Trp Gly
            100                 105                 110
Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15
Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10
```

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

```
Asp Tyr Ala Met His
 1               5
```

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

```
Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Tyr
                 85                  90                  95

Ala Phe Gly Gln Gly Thr Lys Val Glu Ile Lys
            100                 105
```

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

```
Gln Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Asp Trp Val
         35                  40                  45

Ser Ala Ile Thr Trp Asn Ser Gly His Ile Asp Tyr Ala Asp Ser Val
 50                  55                  60

Glu Gly Arg Phe Ala Val Ser Arg Asp Asn Ala Lys Asn Ala Leu Tyr
 65                  70                  75                  80

Leu Gln Met Asn Ser Leu Arg Pro Glu Asp Thr Ala Val Tyr Tyr Cys
                 85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120
```

```
<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5

<210> SEQ ID NO 17
```

```
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
 1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
 1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
```

```
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: L0E7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
```

```
<213> ORGANISM: Artificial Sequence
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
```

-continued

```
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
 1               5                   10

<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 36
gacatccaga tgacccagtc tccatcctcc ctgtctgcat ctgtagggga cagagtcacc      60
atcacttgtc gggcaagtca gggcatcaga aattactag cctggtatca gcaaaaacca     120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tgagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```